United States Patent
Rome et al.

(10) Patent No.: US 10,166,277 B2
(45) Date of Patent: Jan. 1, 2019

(54) VAULT IMMUNOTHERAPY

(71) Applicant: The Regents of the University of California, Oakland, CA (US)

(72) Inventors: Leonard H. Rome, Los Angeles, CA (US); Valerie A. Kickhoefer, Sherman Oaks, CA (US); Sherven Sharma, Oakland, CA (US); Steven M. Dubinett, Los Angeles, CA (US); Isaac Yang, Los Angeles, CA (US); Linda M. Liau, Los Angeles, CA (US); Kathleen A. Kelly, Pacific Palisades, CA (US); Jian Yang, Los Angeles, CA (US); Upendra K. Kar, Oakland, CA (US); Cheryl Champion, Greensboro, GA (US); Janina Jiang, Los Angeles, CA (US)

(73) Assignees: The Regents of the University of California, Oakland, CA (US); The United States of America represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 15/256,683

(22) Filed: Sep. 5, 2016

(65) Prior Publication Data

US 2016/0367653 A1     Dec. 22, 2016

Related U.S. Application Data

(63) Continuation of application No. 14/411,982, filed as application No. PCT/US2013/049816 on Jul. 9, 2013.

(60) Provisional application No. 61/669,568, filed on Jul. 9, 2012.

(51) Int. Cl.

| *A61K 39/00* | (2006.01) |
|---|---|
| *A61K 38/17* | (2006.01) |
| *A61K 38/19* | (2006.01) |
| *A61K 9/50* | (2006.01) |
| *C07K 14/00* | (2006.01) |
| *C07K 14/77* | (2006.01) |
| *A61K 38/45* | (2006.01) |
| *A61K 47/64* | (2017.01) |
| *A61K 47/69* | (2017.01) |

(52) U.S. Cl.
CPC ........ *A61K 39/0011* (2013.01); *A61K 9/5052* (2013.01); *A61K 38/177* (2013.01); *A61K 38/19* (2013.01); *A61K 38/195* (2013.01); *A61K 38/45* (2013.01); *A61K 47/646* (2017.08); *A61K 47/6925* (2017.08); *C07K 14/00* (2013.01); *C07K 14/77* (2013.01); *C12Y 204/0203* (2013.01); *A61K 2039/55516* (2013.01); *A61K 2039/57* (2013.01); *A61K 2039/572* (2013.01); *A61K 2039/575* (2013.01); *A61K 2039/6031* (2013.01); *A61K 2039/6081* (2013.01); *A61K 2039/64* (2013.01); *A61K 2039/645* (2013.01); *C07K 2319/00* (2013.01); *C07K 2319/01* (2013.01); *C12N 2710/14043* (2013.01)

(58) Field of Classification Search
None
See application file for complete search history.

(56) References Cited

U.S. PATENT DOCUMENTS

| 5,763,164 | A | 6/1998 | Calenoff et al. | |
|---|---|---|---|---|
| 5,844,075 | A | 12/1998 | Kawakami et al. | |
| 6,083,703 | A | 7/2000 | Wang et al. | |
| 8,124,109 | B2* | 2/2012 | Kickhoefer | A61K 39/118 424/193.1 |
| 8,318,182 | B2* | 11/2012 | Kickhoefer | A61K 39/118 424/193.1 |
| 8,834,896 | B2* | 9/2014 | Kickhoefer | A61K 39/118 424/234.1 |
| 8,920,807 | B2* | 12/2014 | Rome | A61K 38/00 424/184.1 |
| 9,169,303 | B2* | 10/2015 | Kickhoefer | A61K 39/118 |
| 9,463,232 | B2* | 10/2016 | Kickhoefer | A61K 39/118 |
| 2009/0304751 | A1 | 12/2009 | Kickhoefer et al. | |

FOREIGN PATENT DOCUMENTS

| WO | 2008151197 A2 | 12/2008 |
|---|---|---|
| WO | 2011053991 A2 | 5/2011 |

OTHER PUBLICATIONS

Ezzell (J. NIH Res. 1995 7:46).*
Spitler (Cancer Biotherapy, 1995, 10:1-3).*
Boon (Adv. Can. Res. 1992 58:177-210).*
Champion, et al., "A Vault Nanoparticle Vaccine Induces Protective Mucosal Immunity", Apr. 30, 2009, p. e5409, vol. 4, No. 4, Publisher: PLoS ONE.
Kar, et al., "Novel CCL21-Vault Nanocapsule Intratumoral Delivery Inhibits Lung Cancer Growth", May 3, 2011, p. e18758, vol. 6, No. 5.
Extended European Search Report (EESR) received in EP 13816123.7, dated Oct. 15, 2015.
Casanas, et al., "Vault particles: a new generation of delivery nanodevices", June 6, 2012, pp. 972-977, vol. 23, Publisher: Current Opinion in Biotechnology
Farris, et al., "CD4 T Cells and Antibody Are Required for Optimal Major Outer Membrane Protein Vaccine-Induced Immunity to Chlamydia muridarum Genital Infection", Jul. 26, 2012, pp. 4374-4383, vol. 78, No. 10, Publisher: Infection and Immunity.
Han, et al., "Targeted vault nanoparticles engineered with an endosomolytic peptide deliver biomolecules to the cytoplasm", Jul. 26, 2011, pp. 6128-6137, vol. 5, No. 8, Publisher: ACS Nano.
International Search Report received in PCT/US2013/049816, dated Oct. 15, 2013.
Kar, et al., "Vault Nanocapsules as Adjuvants Favor Cell-Mediated over Antibody-Mediated Immune Responses following Immunization of Mice", Jul. 11, 2012, p. e38553, vol. 7, No. 7, Publisher: PLoS ONE.

* cited by examiner

*Primary Examiner* — Sheela J. Huff
(74) *Attorney, Agent, or Firm* — Suzannah K. Sundby, Esq.; Canady + Lortz LLP

(57) ABSTRACT

The invention relates to compositions of vault complexes for use as adjuvants for stimulating a cellular immune response to an antigen, for example a tumor antigen, and methods of using the vault complexes in the treatment of diseases, such as cancer.

41 Claims, 15 Drawing Sheets
Specification includes a Sequence Listing.

Figure 9 IP or SC routes of Therapeutic Vaccination with OVA-vaults inhibits 3LL-OVA tumor growth
A
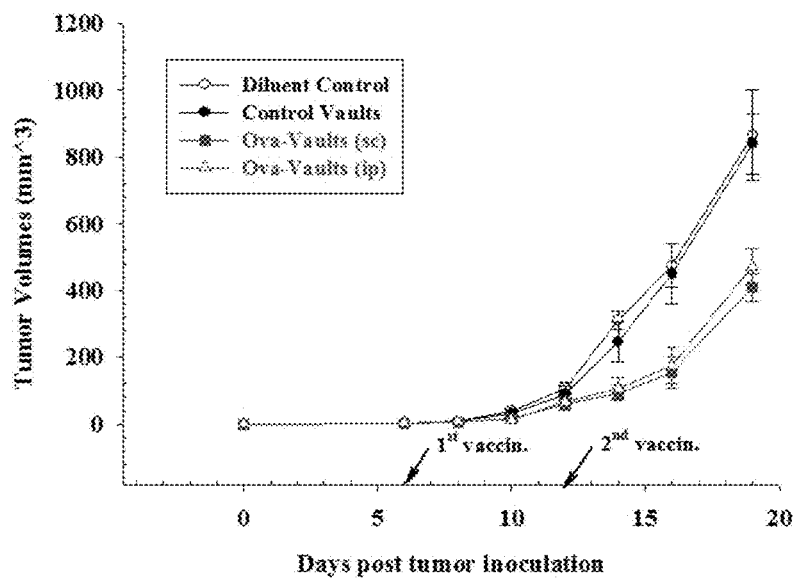
B
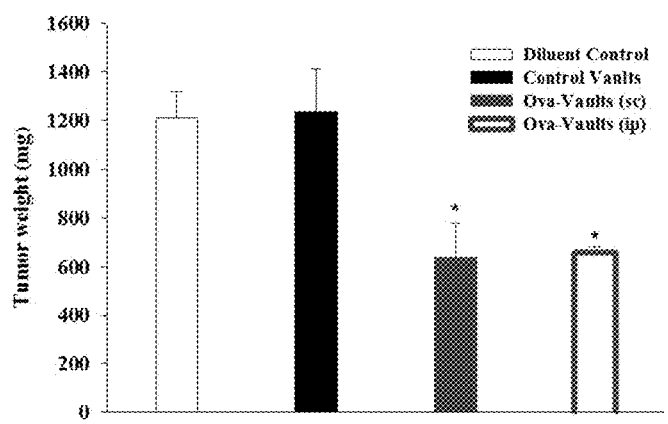

Figure 10 *SC* therapeutic vaccination with OVA-vault on the contralateral flank inhibits 3LL-OVA tumor growth
A
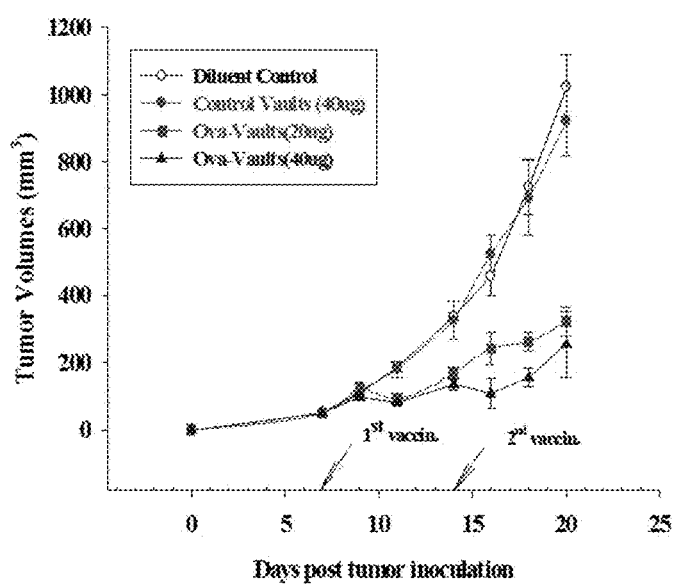
B
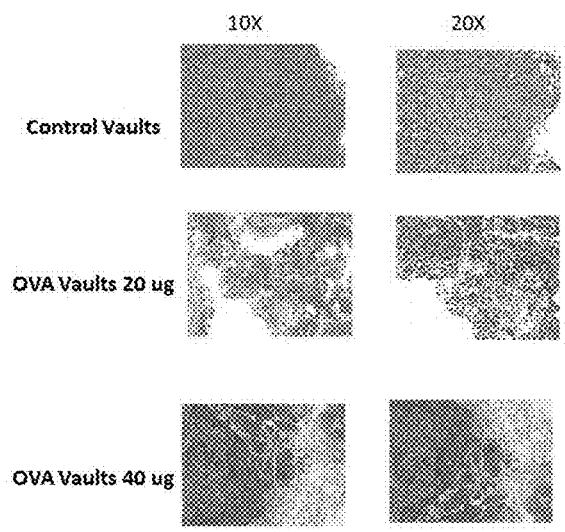

Figure 11 Therapeutic vaccination with OVA-vaults or CCL21 vaults or combination of both vaults leads to tumor rejection and systemic immune responses
Table 2
A
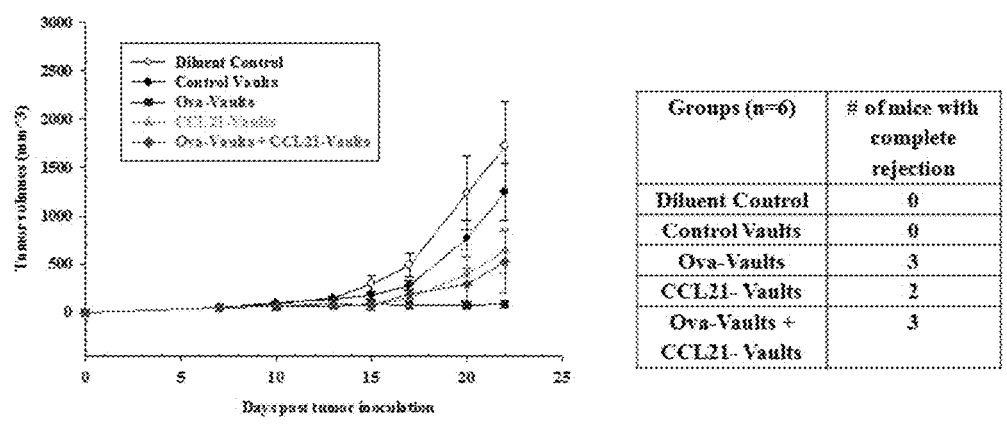
Treatment administered s.c. on contralateral flank of the tumor on days 7, 10 and 14.
B
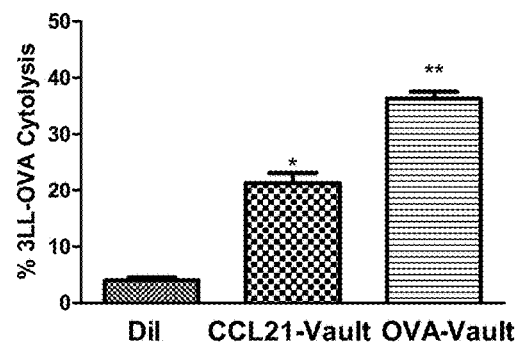

Figure 12  Therapeutic Vaccination with NYESO-vaults inhibits 3LL-NYESO tumor growth
A
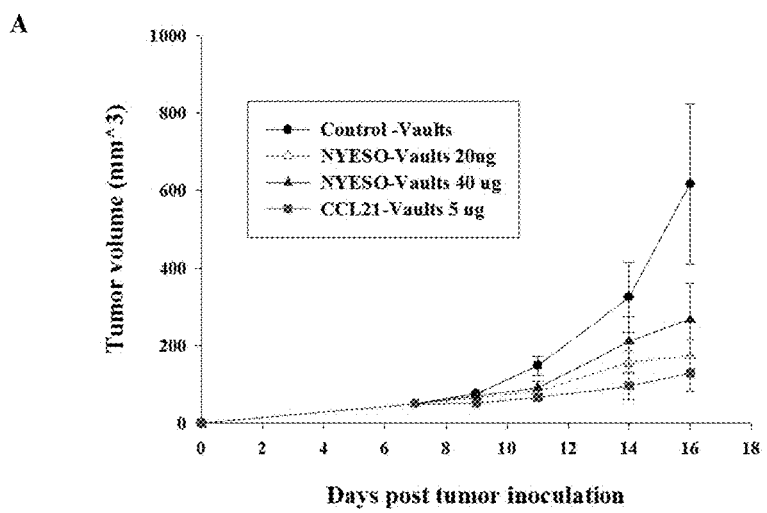
(Day 7,11 & 14 :Vaccination by s.c injection on the contra-lateral flank of tumor)
B
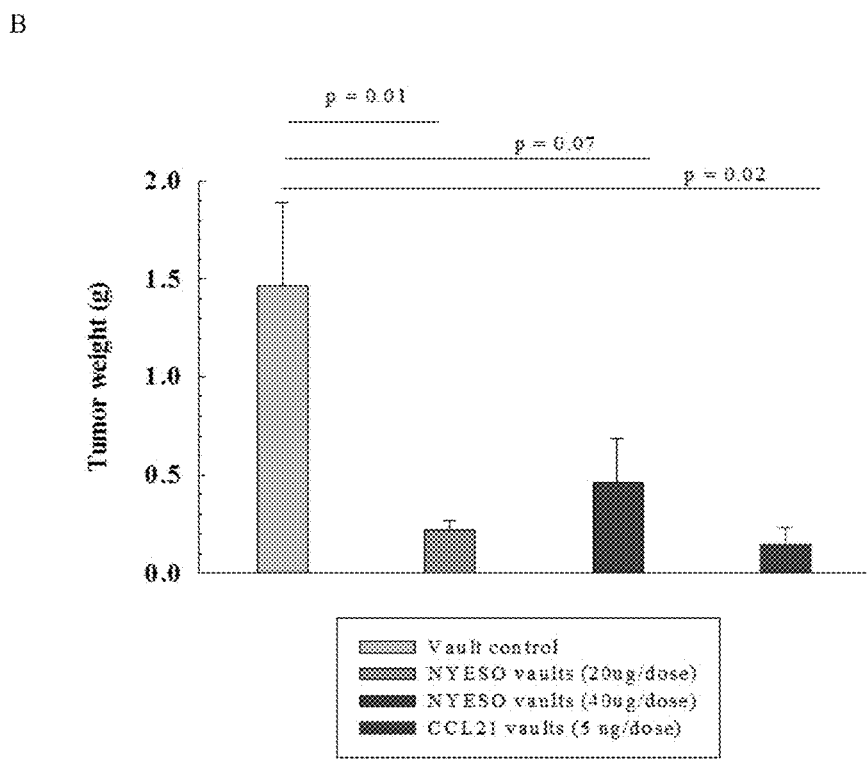

VAULT IMMUNOTHERAPY

STATEMENT REGARDING FEDERALLY SPONSORED RESEARCH OR DEVELOPMENT

This invention was made with Government support under AI079004 awarded by the National Institutes of Health. The Government has certain rights in the invention. This work was supported by the U.S. Department of Veterans Affairs, and the Federal Government has certain rights in the invention.

REFERENCE TO A SEQUENCE LISTING SUBMITTED VIA EFS-WEB

The content of the ASCII text file of the sequence listing named "20160905_034044_141CON1_seq" which is 83.2 kb in size was created on Sep. 5, 2016, and electronically submitted via EFS-Web herewith the application is incorporated herein by reference in its entirety.

BACKGROUND OF THE INVENTION

Field of the Invention

The present invention relates generally to the use of vault compositions as adjuvants for stimulating a cellular immune response to one or more antigens, for example, tumor antigens or cancer biomarkers. Also included in the invention is the use of the compositions for the treatment of diseases, such as cancer.

Introduction

With ongoing disease threats and the promise of emerging immunotherapies, demand for new vaccine technologies is growing. Developing effective and potent vaccines remains one of the most cost-effective strategies for preventing infectious diseases and cancers [1,2]. Vaccines containing killed or inactivated intact microbes elicit strong immune responses but also produce considerable inflammation at the site of vaccination [3-5]. Furthermore, engineered live vaccines, such as non-replicating recombinant viruses have been developed and also induce robust immune responses [6-8]. However, the potential for break-through replication of live vectors and anti-vector immunity further discourage the development of live vector vaccines due to safety concerns [9,10]. To further vaccine development, non-replicating adjuvants are needed which induce robust immunity with minimal inflammation.

The immune-promoting activity of any given vaccination strategy is determined by the presence of the relevant antigenic components in the vaccine formulation, enhanced by the addition of suitable adjuvants capable of activating and promoting an efficient immune response against infectious agents or cancers [1,2]. One approach for tailoring vaccines to elicit certain types of immune responses while avoiding inflammation is to develop subunit vaccines by combining non-living or synthetic antigens with adjuvants [9]. This type of vaccine can deliver defined antigens with reduced inflammatory cytokine production but is dependent on the adjuvant formulation to stimulate cell-mediated immune responses and protection from infectious challenge or prevent tumor growth [11,12]. Most licensed vaccines promote immunity by eliciting humoral immune responses and weak cellular immune responses. Current efforts are directed to producing adjuvants which elicit cell-mediated immunity [13,14].

A major limiting factor in the development of subunit vaccines is engineering immune adjuvants to induce cell-mediated immunity and encourage $CD8^-$ T cell responses through major histocompatibility complex (MHC) class I presentation (MHC-I, cross presentation). Previous work has shown that it is difficult to achieve antigen presentation through MHC-I molecules unless the antigen is specifically targeted to the MHC-I processing machinery [15-17]. A wide range of approaches has been explored including CpG-DNA or toll-like receptor (TLR) ligands, recombinant viral vectors, fusion with bacterial toxins and others [18,19]. Adjuvants can also be designed to elicit specific immunity, such as promoting cellular immunity which is important for protection against many pathogens [20]. Currently none have been successfully developed for use in humans.

Nanoparticle pharmaceutical carriers can be engineered to elicit various types of immunity and are increasingly investigated as adjuvants for vaccines. Different types of nanocarriers, such as polymers (polymeric nanoparticles, micelles, or dendrimers), lipids (liposomes), viruses (viral nanoparticles), and organometallic compounds (carbon nanotubes) have been employed for immunotherapeutic applications [21-23]. We have engineered vaults using a recombinant technique to function as a nanocarrier. Natural vaults are barrel-shaped, hollow, 13 mDa ribonucleoprotein particles that exist in nearly all eukaryotic cells [24,25]. Their precise function is unknown but they have been associated with multidrug resistance, cell signaling, nuclear-cytoplasmic transport and innate immunity [26]. We have shown that recombinant vaults can be produced to contain a bacterial antigen and induce adaptive immune responses and protective immunity following immunization [27]. In addition, vault nanocapsules can also be engineered to promote anti-tumor responses [28]. These studies show that recombinant vault nanocapsules act as adjuvants, are versatile for eliciting various types of immunity and have outstanding potential for compound encapsulation, protection, and delivery.

Description of the Related Art

Vaults are cytoplasmic ubiquitous ribonucleoprotein particles first described in 1986 that are found in all eukaryotic cells (Kedersha et al., J Cell Biol, 103(3):699-709 (1986)). Native vaults are 12.9±1 MDa ovoid spheres with overall dimensions of approximately 40 nm in width and 70 nm in length (Kong et al., Structure, 7(4):371-379 (1999); Kedersha et al., J Cell Biol, 112(2):225-235 (1991)), present in nearly all-eukaryotic organisms with between $10^4$ and $10^7$ particles per cell (Suprenant, Biochemistry, 41(49):14447-14454 (2002)). Despite their cellular abundance, vault function remains elusive although they have been linked to many cellular processes, including the innate immune response, multidrug resistance in cancer cells, multifaceted signaling pathways, and intracellular transport (Berger et al., Cell Mol Life Sci, 66(1):43-61 (2009)).

Vaults are highly stable structures in vitro, and a number of studies indicate that the particles are non-immunogenic (Champion et al., PLoS One, 4(4):e5409 (2009)). Vaults can be engineered and expressed using a baculovirus expression system and heterologous proteins can be encapsulated inside of these recombinant particles using a protein-targeting domain termed INT for vault INTeraction. Several heterologous proteins have been fused to the INT domain (e.g. fluorescent and enzymatic proteins) and these fusion proteins are expressed in the recombinant vaults and retain their native characteristics, thus conferring new properties onto these vaults (Stephen et al., J Biol Chem, 276(26):23217-23220 (2001); Kickhoefer et al., Proc Natl Acad Sci USA, 102(12):4348-4352 (2005)).

Vaults are generally described in U.S. Pat. No. 7,482,319, filed on Mar. 10, 2004; U.S. application Ser. No. 12/252,200, filed on Oct. 15, 2008; International Application No. PCT/US2004/007434, filed on Mar. 10, 2004; U.S. Provisional Application No. 60/453,800, filed on Mar. 20, 2003; U.S. Pat. No. 6,156,879, filed on Jun. 3, 1998; U.S. Pat. No. 6,555,347, filed on Jun. 28, 2000; U.S. Pat. No. 6,110,740, filed on Mar. 26, 1999; International Application No. PCT/US1999/06683, filed on Mar. 26, 1999; U.S. Provisional App. No. 60/079,634, filed on Mar. 27, 1998; and International Application No. PCT/US1998/011348, filed on Jun. 3, 1998. Vault compositions for immunization against chlamydia genital infection are described in U.S. application Ser. No. 12/467,255, filed on May 15, 2009. The entire contents of these applications are incorporated by reference in their entirety for all purposes.

SUMMARY OF THE INVENTION

As shown herein, we have characterized the types of immune responses elicited by engineered vault nanopcapsules compared to another type of nanocarrier, liposomes, using a well-characterized model antigen, ovalbumin (OVA). Ovalbumin is a highly immunogenic antigen and has often been used as a proof of principle for numerous vaccination strategies [29,30]. We show that immunization of mice with OVA encapsulated in vault nanocapsules efficiently stimulates the immune response to elicit robust $CD8^+$, $CD4^+$ memory T cell responses and antibody titers to OVA. Accordingly, as also shown herein, vault nanocapsules can be used as subunit vaccines which can generate both cellular and humoral immunity against antigens for human pathogens and cancer, which we have demonstrated for a number of tumor associated antigens.

In one aspect, the present invention provides a method for stimulating a cellular immune response in a subject, comprising administering to the subject an effective amount of an antigenic peptide or an antigenic fragment or variant thereof incorporated within a vault complex.

In a second aspect, the present invention provides a pharmaceutical composition for preventing or treating a subject for cancer, comprising a tumor antigen or an antigenic fragment or variant thereof incorporated within a vault complex, and optionally at least one pharmaceutically acceptable excipient, sufficient to stimulate a cellular immune response.

In a yet third aspect, the present invention provides a method of preventing or treating cancer in a subject, comprising administering to the subject an effective amount of a tumor antigen or an antigenic fragment or variant thereof incorporated within a vault complex, sufficient to stimulate a cellular immune response. In some embodiments, the administering reduces tumor volume or tumor growth.

In various embodiments of the above aspects, the antigenic peptide is a tumor antigen. In other embodiments, the vault complex comprises two or more vault complexes, in which each vault complex comprises two or more different antigenic peptides or antigenic fragments or variants.

In other embodiments, one or multiple copies of the antigenic peptide can be fused to INT or MVP. If fused to MVP, the antigenic peptide can be fused to the N-terminus of MVP or to the C-terminus of MVP. In some embodiments, the INT comprises the amino acid sequence of SEQ ID NO: 2.

In further embodiments, the vault complex comprises MVP, in which the number of MVP is 1-78. In some embodiments, the number of MVP is 78.

In additional embodiments, the vault complex further comprises VPARP or modified VPARP, or a portion of VPARP, or a modified portion of VPARP.

In particular embodiments, the cellular immune response is induction of $CD8^+$ and $CD4^+$ memory T-cells. In other embodiments, the cellular immune response is production of INFγ.

Further embodiments comprise administering to the subject a vault complex containing a chemokine, in which the chemokine can be CCL21. The administration can be with or without an antigen.

BRIEF DESCRIPTION OF THE DRAWINGS

These and other features, aspects, and advantages of the present invention will become better understood with regard to the following description, and accompanying drawings, where:

FIG. 9: OVA-vault vaccination inhibited tumor growth. C57BL/6 mice bearing 7 day 3LL-OVA established tumors (s.c.) were treated with diluent normal saline (NS), control vaults (20 μg) and OVA-vaults (2-20 μg) by sc or ip injection. Bisecting tumor diameters were measured with calipers. Tumor growth (9A) and tumor weights (9B) were inhibited in the OVA-vault treatments compared to controls. Data; Mean±SEM, *p<0.05 between OVA-vault and controls, n=8 mice/group.

FIG. 10: OVA-vault vaccination on the contralateral flank of tumor inoculation inhibited tumor growth. C57BL/6 mice bearing 7 day 3LL-OVA established tumors (s.c.) were treated with diluent normal saline (NS), control vaults (40 μg) and OVA-vaults (20-40 μg) by sc injection. Bisecting tumor diameters were measured with calipers. Tumor growth was inhibited in the OVA-vault vaccination group compared to controls (10A). H&E of tumor sections showed that the Ova vault vaccination groups have diffuse tumor burden with leukocytic infiltrates compared to control vaults that have solid tumor mass and few infiltrates (10B). Data; Mean±SEM, *p<0.05 between OVA-vault and controls, n=8 mice/group.

FIG. 11: OVA-vault, CCL21 vault, or combined CCL21vault+OVA-vault treatment on the contralateral flank of tumor inoculation inhibited tumor growth and induced systemic immune responses. C57BL/6 mice bearing 7 day 3LL-OVA established tumors (s.c.) were treated with diluent normal saline (NS), control vaults (20 μg), OVA-vaults (20 μg), CCL21 (5 μg), and CCL21 (5 μg)+OVA (20 μg) by sc injection. Tumor growth was inhibited in the treatment groups compared to controls (11A) with 40-50% of treated mice completely rejecting tumors (Table 2). Cytolysis of CFSE labeled 3LL-OVA following incubation with splenocytes from treated mice at effector to target ratio of 1:1 for 4 hours showed enhanced tumor cytolysis compared to controls (11B). Data; Mean±SEM, *p<0.05 between OVA-vault and controls, n=6 mice/group.

FIG. 12: NYESO-vault vaccination inhibited tumor growth. C57BL/6 mice bearing 7 day 3LL-NYESO established tumors (s.c.) were treated with control vaults (20 μg), CCL21-vaults (5 μg) and NYESO vaults (20-40 μg) by sc injection on the contralateral flank. Tumor growth (12A) and tumor weights (12B) were inhibited in the CCL21 vault and NYESO-vault treatments compared to control. Data; Mean±SEM, *p<0.05 between OVA-vault and controls, n=6 mice/group.

DETAILED DESCRIPTION OF THE INVENTION

Figure 1:
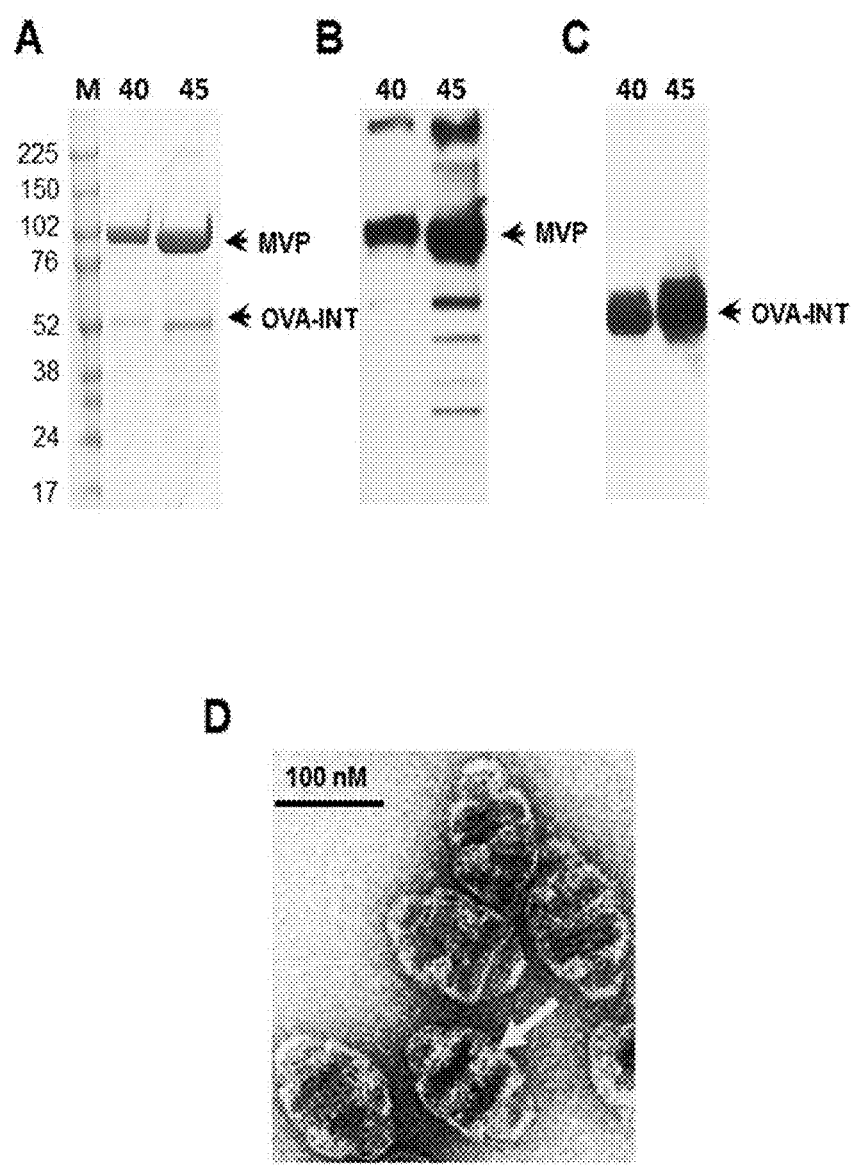
FIG. 1: Analysis of purified recombinant vault particles containing OVA-INT. (A) Representative gel image showing co-purification of the protein species MVP and OVA-INT. Sucrose gradients of 40% to 60% run in SDS-PAGE (4%-15%). Lane: M: protein molecular weight markers, 40: 40% fractions of sucrose gradient and 45% fractions of sucrose gradient. (B) The gradient fractions were probed with either anti-MVP rabbit polyclonal antisera or (C) anti-OVA rabbit polyclonal antisera. (D) Negative stain EM of CP-OVA recombinant vaults Bar, 100 nm.

The descriptions of various aspects of the invention are presented for purposes of illustration, and are not intended to be exhaustive or to limit the invention to the forms disclosed. Persons skilled in the relevant art can appreciate that many modifications and variations are possible in light of the embodiment teachings.

It should be noted that the language used herein has been principally selected for readability and instructional purposes, and it may not have been selected to delineate or circumscribe the inventive subject matter. Accordingly, the disclosure is intended to be illustrative, but not limiting, of the scope of invention.

It must be noted that, as used in the specification, the singular forms "a", "an", and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of embodiments of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the invention herein.

Definitions

Terms used in the claims and specification are defined as set forth below unless otherwise specified.

As used herein, the term "vault" or "vault particle" refers to a large cytoplasmic ribonucleoprotein (RNP) particle found in eukaryotic cells. The vault or vault particle is composed of MVP, VPARP, and/or TEP1 proteins and one or more untranslated vRNA molecules.

As used herein, the term "vault complex" refers to a vault or recombinant vault that encapsulates a small molecule or protein of interest. A vault complex can include all the components of a vault or vault particle or just a subset. A vault complex with just a subset of the components found in vaults or vault particles can also be termed a "vault-like particle". Examples of vault-like particles include: 1) MVP without VPARP, TEP1 and vRNA; 2) MVP and either VPARP or a portion of VPARP, without TEP1 and vRNA; 3) MVP and TEP1 or a portion of TEP1 with or without the one or more than one vRNA, and without VPARP; 4) MVP without VPARP, TEP1 and vRNA, where the MVP is modified to attract a specific substance within the vault-like particle, or modified to attract the vault complex to a specific tissue, cell type or environmental medium, or modified both to attract a specific substance within the vault complex and to attract the vault particle to a specific tissue, cell type or environmental medium; and 5) MVP, and either VPARP or a portion of VPARP, or TEP1 or a portion of TEP1 with or without the one or more than one vRNA, or with both VPARP or a portion of VPARP, and TEP1, with or without the one or more than one vRNA, where one or more than one of the MVP, VPARP or portion of VPARP and TEP1 is modified to attract a specific substance within the vault-like particle, or modified to attract the vault particle to a specific tissue, cell type or environmental medium, or modified both to attract a specific substance within the vault complex and to attract the vault complex to a specific tissue, cell type or environmental medium. As used herein, a vault complex is sometimes referred to as a "vault nanoparticle".

As used herein, the term "vault targeting domain" or "vault interaction domain" is a domain that is responsible for interaction or binding of a heterologous fusion protein with a vault protein, or interaction of a VPARP with a vault protein, such as a MVP. As used herein, the term "INT domain" is a vault interaction domain from a vault poly ADP-ribose polymerase (VPARP) that is responsible for the interaction of VPARP with a major vault protein (MVP). The term "INT domain" refers to a major vault protein (MVP) interaction domain comprising amino acids 1563-1724 of VPARP.

As used herein, the term "MVP" is major vault protein. The term "cp-MVP" is a cysteine-rich peptide major vault protein.

The term "VPARP" refers to a vault poly ADP-ribose polymerase.

As used herein, the term "TEP-1" is a telomerase/vault associated protein 1.

As used herein, the term "vRNA" is an untranslated RNA molecule found in vaults.

As used herein, the term "vector" is a DNA or RNA molecule used as a vehicle to transfer foreign genetic material into a cell. The four major types of vectors are plasmids, bacteriophages and other viruses, cosmids, and artificial chromosomes. Vectors can include an origin of replication, a multi-cloning site, and a selectable marker.

As used herein, a "cell" includes eukaryotic and prokaryotic cells.

As used herein, the terms "organism", "tissue" and "cell" include naturally occurring organisms, tissues and cells, genetically modified organisms, tissues and cells, and pathological tissues and cells, such as tumor cell lines in vitro and tumors in vivo.

As used herein, the term "extracellular environment" is the environment external to the cell.

As used herein, the term "in vivo" refers to processes that occur in a living organism.

A "subject" referred to herein can be any animal, including a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species, or a human.

The term "mammal" as used herein includes both humans and non-humans and include but is not limited to humans, non-human primates, canines, felines, murines, bovines, equines, and porcines.

As used herein, the term "human" refers to "*Homo sapiens.*"

As used herein, the term "sufficient amount" is an amount sufficient to produce a desired effect, e.g., an amount sufficient to stimulate a cellular immune response.

As used herein, the term "therapeutically effective amount" is an amount that is effective to ameliorate a symptom of a disease, such as cancer.

A "prophylactically effective amount" refers to an amount that is effective for prophylaxis.

As used herein, the term "stimulating" refers to activating, increasing, or triggering a molecular, cellular or enzymatic activity or response in a cell or organism, e.g. a cellular immune response.

As used herein, the term "inhibiting" refers to deactivating, decreasing, or shutting down a molecular, cellular or enzymatic activity or response in a cell or organism.

As used herein, the term "administering" includes any suitable route of administration, as will be appreciated by one of ordinary skill in the art with reference to this disclosure, including direct injection into a solid organ, direct injection into a cell mass such as a tumor, inhalation, intraperitoneal injection, intravenous injection, topical application on a mucous membrane, or application to or dispersion within an environmental medium, and a combination of the preceding.

As used herein, the term "treating" or "treatment" refers to the reduction or elimination of symptoms of a disease, e.g., cancer.

As used herein, the term "preventing" or "prevention" refers to the reduction or elimination of the onset of symptoms of a disease, e.g., cancer.

As used herein, the term "regressing" or "regression" refers to the reduction or reversal of symptoms of a disease after its onset, e.g., cancer remission.

As used in this disclosure, the term "modified" and variations of the term, such as "modification," means one or more than one change to the naturally occurring sequence of MVP, VPARP or TEP1 selected from the group consisting of addition of a polypeptide sequence to the C-terminal, addition of a polypeptide sequence to the N-terminal, deletion of between about 1 and 100 amino acid residues from the C-terminal, deletion of between about 1 and 100 amino acid residues from the N-terminal, substitution of one or more than one amino acid residue that does not change the function of the polypeptide, as will be appreciated by one of ordinary skill in the art with reference to this disclosure, such as for example, an alanine to glycine substitution, and a combination of the preceding.

As used herein, the term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

As used in this disclosure, the term "comprise" and variations of the term, such as "comprising" and "comprises," are not intended to exclude other additives, components, integers or steps.

It must be noted that, as used in the specification and the appended claims, the singular forms "a," "an" and "the" include plural referents unless the context clearly dictates otherwise.

Compositions of the Invention

As described in more detail below, the invention includes compositions and methods of using vault complexes. An embodiment of the invention has recombinant vaults having a MVP and an antigen, e.g., a tumor antigen. The vault complex can be used as an adjuvant for stimulating a cellular immune response to the antigen.

Vaults and Vault Complexes

The compositions of the invention comprise a vault complex. A vault complex is a recombinant particle that encapsulates a small molecule (drug, sensor, toxin, etc.), or a protein of interest, e.g., a peptide, or a protein, including an endogenous protein, a heterologous protein, a recombinant protein, or recombinant fusion protein. Vault complexes of the invention can include a tumor antigen.

Vaults, e.g., vault particles are ubiquitous, highly conserved ribonucleoprotein particles found in nearly all eukaryotic tissues and cells, including dendritic cells (DCs), endometrium, and lung, and in phylogeny as diverse as mammals, avians, amphibians, the slime mold *Dictyostelium discoideum*, and the protozoan *Trypanosoma brucei* (Izquierdo et al., Am. J. Pathol., 148(3):877-87 (1996)). Vaults have a hollow, barrel-like structure with two protruding end caps, an invaginated waist, and regular small openings surround the vault cap. These openings are large enough to allow small molecules and ions to enter the interior of the vault. Vaults have a mass of about 12.9±1 MDa (Kedersha et al., J. Cell Biol., 112(2):225-35 (1991)) and overall dimensions of about 42×42×75 nm (Kong et al., Structure, 7(4):371-9 (1999)). The volume of the internal vault cavity is approximately $50 \times 10^3$ nm$^3$, which is large enough to enclose an entire ribosomal protein.

Vaults comprise three different proteins, designated MVP, VPARP and TEP1, and comprise one or more different untranslated RNA molecules, designated vRNAs. The number of vRNA can vary. For example, the rat *Rattus norvegicus* has only one form of vRNA per vault, while humans have three forms of vRNA per vault. The most abundant protein, major vault protein (MVP), is a 95.8 kDa protein in *Rattus norvegicus* and a 99.3 kDa protein in humans which is present in 96 copies per vault and accounts for about 75% of the total protein mass of the vault particle. The two other proteins, the vault poly-ADP ribose polymerase, VPARP, a 193.3 kDa protein in humans, and the telomerase/vault associated protein 1, TEP1, a 292 kDa protein in *Rattus norvegicus* and a 290 kDa protein in humans, are each present in between about 2 and 16 copies per vault.

VPARP, INT Domain, and INT Fusion Proteins

A vault poly ADP-ribose polymerase (VPARP) includes a region of about 350 amino acids that shares 28% identity with the catalytic domain of poly ADP-ribosyl polymerase, PARP, a nuclear protein that catalyzes the formation of ADP-ribose polymers in response to DNA damage. VPARP catalyzes an NAD-dependent poly ADP-ribosylation reaction, and purified vaults have poly ADP-ribosylation activity that targets MVP, as well as VPARP itself. VPARP includes a INT domain (major vault protein (MVP) interaction domain). The INT domain is responsible for the interaction of VPARP with a major vault protein (MVP).

A vault complex of the invention can include a INT domain. The INT domain, also referred to as mINT domain for minimal INT domain, is responsible for interaction of a protein of interest with a vault protein such as a MVP. In some embodiments, the INT domain is expressed as a fusion protein with a protein of interest. Alternatively, a protein of interest can be covalently or non-covalently attached. The INT of the vault complexes of the invention are derived from VPARP sequences. Exemplary VPARP sequences and INT sequences can be found in Table 1. One of skill in the art understands that the INT can have the entire naturally occurring sequence or portions of the sequence or fragments thereof. In other embodiments, the INT has at least 50%, 60%, 70%, 80%, 90%, 95%, 96%, 97%, 98% or 99% sequence identity to any of the VPARP and/or INT sequences disclosed in Table 1.

In one embodiment, the INT is derived from a human VPARP, SEQ ID NO:3, GenBank accession number AAD47250, encoded by the cDNA, SEQ ID NO:5, GenBank accession number AF158255. In some embodiments, the vault targeting domain comprises or consists of the INT domain corresponding to residues 1473-1724 of human VPARP protein sequence (full human VPARP amino acid sequence is SEQ ID NO:3). In other embodiments, the vault targeting domain comprises or consists of the mINT domain comprising residues 1563-1724 (SEQ ID NO: 2) of the human VPARP protein sequence. In certain embodiments, the vault targeting domain is at least 90%, 91%, 92%, 93%, 94%, 95%, 96%, 97%, 98%, or 99% identical to SEQ ID NO: 2 or 3.

In alternative embodiments, as with VPARP, a major vault protein (MVP) interaction domain can be derived from TEP1 sequences. Such interaction domains can be termed, for example INT2, to distinguish them from a VPARP interaction domain. One of skill in the art understands that the INT can have the entire naturally occurring sequence of the vault interaction domain in TEP1 or portions of the sequence or fragments thereof.

MVP

A vault complex of the invention can include an MVP. Exemplary MVP sequences can be found in Table 1. One of skill in the art understands that the MVP can have the entire naturally occurring sequence or portions of the sequence or fragments thereof. In other embodiments, the MVP has at least 50%, 60%, 70%, 80%, 90%, 95%, 96%, 97%, 98% or 99% sequence identity to any of the MVP sequences disclosed in Table 1.

In one embodiment, the MVP is human MVP, SEQ ID NO:6, GenBank accession number CAA56256, encoded by the cDNA, SEQ ID NO:7, GenBank accession number X79882. In other embodiments, the MVP is at least 90%, 91%, 92%, 93%, 94%, 95%, 96%, 97%, 98%, or 99% identical to the MVP sequences described herein.

In one embodiment, there is provided a vault complex comprising, consisting essentially of, or consisting of an MVP modified by adding a peptide to the N-terminal to create a one or more than one of heavy metal binding domains. In a preferred embodiment, the heavy metal binding domains bind a heavy metal selected from the group consisting of cadmium, copper, gold and mercury. In a preferred embodiment, the peptide added to the N-terminal is a cysteine-rich peptide (CP), such as for example, SEQ ID NO:8, the MVP is human MVP, SEQ ID NO:6, and the modification results in CP-MVP, SEQ ID NO:9, encoded by the cDNA, SEQ ID NO:10. These embodiments are particularly useful because vault particles consisting of CP-MVP are stable without the presence of other vault proteins.

Any of the vault complexes described herein can include MVPs or modified MVPs disclosed herein.

TEP1

In some embodiments, a vault complex of the invention can include a TEP1 protein. Exemplary TEP1 sequences can be found in Table 1. One of skill in the art understands that the TEP1 can have the entire naturally occurring sequence or portions of the sequence or fragments thereof. In other embodiments, the TEP1 has at least 50%, 60%, 70%, 80%, 90%, 95%, 96%, 97%, 98% or 99% sequence identity to any of the TEP1 sequences disclosed in Table 1.

The TEP1 can be human TEP1, SEQ ID NO:11, GenBank accession number AAC51107, encoded by the cDNA, SEQ ID NO:12, GenBank accession number U86136. Any of the vault complexes described herein can include TEP1 or modifications thereof.

vRNA

A vault complex of the invention can include a vRNA. Exemplary vRNA sequences can be found in Table 1. One of skill in the art understands that the vRNA can have the entire naturally occurring sequence or portions of the sequence or fragments thereof. In other embodiments, the vRNA has at least 50%, 60%, 70%, 80%, 90%, 95%, 96%, 97%, 98% or 99% sequence identity to any of the vRNA sequences disclosed in Table 1.

In one embodiment, the vRNA can be a human vRNA, SEQ ID NO:13, GenBank accession number AF045143, SEQ ID NO:14, GenBank accession number AF045144, or SEQ ID NO:15, GenBank accession number AF045145, or a combination of the preceding.

As will be appreciated by one of ordinary skill in the art with reference to this disclosure, the actual sequence of any of MVP, VPARP, TEP1 and vRNAs can be from any species suitable for the purposes disclosed in this disclosure, even though reference or examples are made to sequences from specific species. Further, as will be appreciated by one of ordinary skill in the art with reference to this disclosure, there are some intraspecies variations in the sequences of MVP, VPARP, TEP1 and vRNAs that are not relevant to the purposes of the present invention. Therefore, references to MVP, VPARP, TEP1 and vRNAs are intended to include such intraspecies variants.

Isolated Nucleic Acids and Vectors

Suitable expression vectors generally include DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of expression vectors can be systemic, such as by intravenous or intramuscular administration, by administration to target cells ex-planted from the patient followed by reintroduction into the patient, or by any other means that allows for introduction into a desired target cell.

Plasmids expressing a nucleic acid sequence can be transfected into target cells as a complex with cationic lipid carriers (e.g., Oligofectamine) or non-cationic lipid-based carriers (e.g., Transit-TKO™). Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g., EPV and EBV vectors. Constructs for the recombinant expression of a nucleic acid encoding a fusion protein will generally require regulatory elements, e.g., promoters, enhancers, etc., to ensure the expression of the fusion nucleic acid in target cells. Other aspects to consider for vectors and constructs are further described below.

Vectors useful for the delivery of a nucleic acid can include regulatory elements (promoter, enhancer, etc.) sufficient for expression of the nucleic acid in the desired target cell or tissue. The regulatory elements can be chosen to provide either constitutive or regulated/inducible expression. A person skilled in the art would be able to choose the appropriate regulatory/promoter sequence based on the intended use of the transgene.

In a specific embodiment, viral vectors that contain the recombinant gene can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding a fusion protein are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of isolated nucleic acids encoding fusion proteins into a cell. Adenoviruses are especially attractive vehicles for delivering genes to respiratory epithelia or for use in adenovirus-based delivery systems such as delivery to the liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing a nucleic acid molecule featured in the invention, a method for constructing the recombinant AV vector, and a method for delivering the vector into target cells, are described in Xia H et al. (2002), Nat. Biotech. 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Examples of additional expression vectors that can be used in the invention include pFASTBAC expression vectors and *E. coli* pET28a expression vectors.

Generally, recombinant vectors capable of expressing genes for recombinant fusion proteins are delivered into and persist in target cells. The vectors or plasmids can be transfected into target cells by a transfection agent, such as Lipofectamine. Examples of cells useful for expressing the nucleic acids encoding the fusion proteins of the invention include Sf9 cells or insect larvae cells. Recombinant vaults based on expression of the MVP protein alone can be produced in insect cells. Stephen, A. G. et al. (2001). *J. Biol. Chem.* 276:23217:23220; Poderycki, M. J., et al. (2006). *Biochemistry* (Mosc). 45: 12184-12193.

Pharmaceutical Compositions of the Invention

In one embodiment, the invention provides methods using pharmaceutical compositions comprising the vault complexes of the invention. These compositions can comprise, in addition to one or more of the vault complexes, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

In certain embodiments, the pharmaceutical compositions that are injected intra-tumorally comprise an isotonic or other suitable carrier fluid or solution.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In other embodiments, pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In some embodiments, administration of the pharmaceutical compositions may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration. Formulations for parenteral administration may include sterile aqueous solutions which may also contain buffers, diluents and other suitable additives. Formulations may be reconstituted from freeze-dried (lyophilized) preparations. For intravenous use, the total concentration of solutes should be controlled to render the preparation isotonic.

Methods of Use

Vault complexes described herein can be used to deliver a protein of interest (e.g., a tumor antigen) to a cell, a tissue, an environment outside a cell, a tumor, an organism or a subject. In one embodiment, the vault complex comprises a tumor antigen, and the vault complex is introduced to the cell, tissue, or tumor. In some embodiments, the vault complex is introduced into the extracellular environment surrounding the cell. In other embodiments, the vault complex is introduced into an organism or subject. Delivery of the vault complex of the invention can include administering the vault complex to a specific tissue, specific cells, an environmental medium, or to the organism.

The methods of the invention comprise delivering a biomolecule to a cell by contacting the cell with any of the vault complexes described herein. Cells of the invention can include, but are not limited to, any eukaryotic cell, mammalian cell, or human cells, including tumor cells.

Methods of the invention include delivery of the vault complex to a subject. The delivery of a vault complex to a subject in need thereof can be achieved in a number of different ways. In vivo delivery can be performed directly by administering a vault complex to a subject. Alternatively, delivery can be performed indirectly by administering one or more vectors that encode and direct the expression of the vault complex or components of the vault complex. In one embodiment, the vault complex is administered to a mammal, such as a mouse or rat. In another embodiment, the vault complex is administered to a human.

In another embodiment, the methods of delivery of the invention include systemic injection of vaults. In other embodiments, the methods of delivery of the invention include oral ingestion of vaults.

Methods of Treatment

The invention features a method of treating or managing disease, such as cancer, by administering the vault complex of the invention to a subject (e.g., patient). In some embodiments, the method of the invention comprises treating or cancer in a subject in need of such treatment or management, comprising administering to the subject a therapeutically effective amount of the vault complexes described herein.

The data obtained from cell culture assays and animal studies can be used in formulating a range of dosage for use in humans. For any compound used in the methods featured in the invention, the therapeutically effective dose can be estimated initially from cell culture assays. A dose may be formulated in animal models to achieve a circulating plasma concentration range of the vault complex. Such information can be used to more accurately determine useful doses in humans.

The pharmaceutical composition according to the present invention to be given to a subject, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. A composition can be administered alone or in combination with other treatments, either simultaneously or sequentially dependent upon the condition to be treated.

In certain embodiments, the dosage of vault complexes is between about 0.1 and 10,000 micrograms per kilogram of body weight or environmental medium. In another embodiment, the dosage of vault complexes is between about 1 and 1,000 micrograms per kilogram of body weight or environmental medium. In another embodiment, the dosage of vault complexes is between about 10 and 1,000 micrograms per kilogram of body weight or environmental medium. For intravenous injection and intraperitoneal injection, the dosage is preferably administered in a final volume of between about 0.1 and 10 ml. For inhalation the dosage is preferably administered in a final volume of between about 0.01 and 1 ml. As will be appreciated by one of ordinary skill in the art with reference to this disclosure, the dose can be repeated a one or multiple times as needed using the same parameters to effect the purposes disclosed in this disclosure.

For instance, the pharmaceutical composition may be administered once to a subject, or the vault complex may be administered as two, three, or more sub-doses or injections at appropriate intervals. In that case, the vault complexes can be injected in sub-doses in order to achieve the total required dosage.

The vault complexes featured in the invention can be administered in combinations of vault complexes containing different tumor antigens, or in combination with other known agents effective in treatment of cancer. An administering physician can adjust the amount and timing of vault complex administration or injection on the basis of results observed using standard measures of efficacy known in the art or described herein. The skilled artisan will also appreciate that certain factors may influence the dosage and timing required to effectively treat a subject, including but not limited to the severity of the disease or disorder, previous treatments, the general health and/or age of the subject, and other diseases present.

Methods of Preparing Vault Complexes

The methods of the invention include preparing the vault complexes described herein.

In one embodiment, the vault complexes are derived or purified from natural sources, such as mammalian liver or spleen tissue, using methods known to those with skill in the art, such as for example tissue homogenization, differential centrifugation, discontinuous sucrose gradient fractionation and cesium chloride gradient fractionation. In another embodiment, the vault complexes are made using recombinant technology.

In some embodiments, a target of interest, i.e., protein of interest, is selected for packaging in the vault complexes. The target of interest may be selected from the group consisting of an enzyme, a pharmaceutical agent, a plasmid, a polynucleotide, a polypeptide, a sensor and a combination of the preceding. In a preferred embodiment, the target of interest is a recombinant protein, e.g., a cell adhesion modifying substance, e.g., an RGD-containing peptide.

Preferably, if the target of interest is a recombinant protein, the polynucleotide sequences encoding the recombinant protein are used to generate a bacmid DNA, which is used to generate a baculovirus comprising the sequence. The baculovirus is then used to infect insect cells for protein production using an in situ assembly system, such as the baculovirus protein expression system, according to standard techniques, as will be appreciated by one of ordinary skill in the art with reference to this disclosure. Advantageously, the baculovirus protein expression system can be used to produce milligram quantities of vault complexes, and this system can be scaled up to allow production of gram quantities of vault complexes according to the present invention.

In another embodiment, the target of interest is incorporated into the provided vaults. In one embodiment, incorporation is accomplished by incubating the vaults with the target of interest at an appropriate temperature and for an appropriate time, as will be appreciated by one of ordinary skill in the art with reference to this disclosure. The vaults containing the protein of interest are then purified, such as, for example sucrose gradient fractionation, as will be appreciated by one of ordinary skill in the art with reference to this disclosure.

In other embodiments, the vaults comprising the target of interest are administered to an organism, to a specific tissue, to specific cells, or to an environmental medium. Administration is accomplished using any suitable route, as will be appreciated by one of ordinary skill in the art with reference to this disclosure.

In one embodiment, the method comprises preparing the composition of the invention by a) mixing a INT or INT fusion protein generated in insect Sf9 cells with a MVP or MVP fusion protein generated in insect Sf9 cells to generate a mixture; b) incubating the mixture for a sufficient period of time to allow formation of vault complexes, thereby generating the composition. For example, Sf9 cells are infected with pVI-MVP encoding recombinant baculoviruses. Lysates containing recombinant tumor antigen-INT and rat MVP generated in Sf-9 cells can be mixed to allow the formation of a macromolecular vault complex containing the tumor antigen-INT fusion protein.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Preparation of Recombinant Vaults Packaged with Chicken Ovalbumin

Recombinant vaults were produced using a baculovirus expression system in Sf9 insect cells that express a stabilized form of recombinant vaults (CP) and contain a cysteine rich peptide on the N terminus to increase stability [31]. Cryo-electron microscopy imaging of recombinant and tissue derived vaults revealed the localization of the MVP interacting domain, INT [31]. Another form of recombinant vaults (CPZ) contains a 33 amino acid mimic of the Ig binding domain of staphylococcal protein A (Z) in addition to the CP peptide [32]. CPZ vaults were shown to bind antibody and may direct uptake thorough FcRs [27]. These vaults (CP or CPZ) were packaged with chicken ovalbumin by fusion of OVA protein to the vault-targeting protein, INT to form OVA-INT. The OVA-containing vaults were purified and the majority of particles were found in the 40% and 45% sucrose fraction as previously described [33]. Analysis of these fractions by SDS-PAGE and Western blotting (FIG. 1) shows the co-purification of MVP and OVA-INT (FIG. 1A). The identity of the components was confirmed by Western analysis with either an anti-MVP polyclonal antibody (FIG. 1B) or an anti-OVA antibody (FIG. 1C). Purified CP-OVA recombinant vaults were evaluated by negative stain electron microscopy (FIG. 1D). The addition of the OVA-INT protein to CP or CPZ did not alter recombinant vault morphology as compared to empty CP vaults when evaluated by transmission electron microcopy (data not shown) and as shown previously [27]. The presence of additional protein density or lighter staining area (arrow) near the waist of the vault barrel, which based on earlier structural studies, is the expected location of OVA-INT [34]. We used these CP and CPZ-vaults containing OVA-INT in vaccinations, henceforth referred to as CP-OVA and CPZ-OVA.

Figure 2:
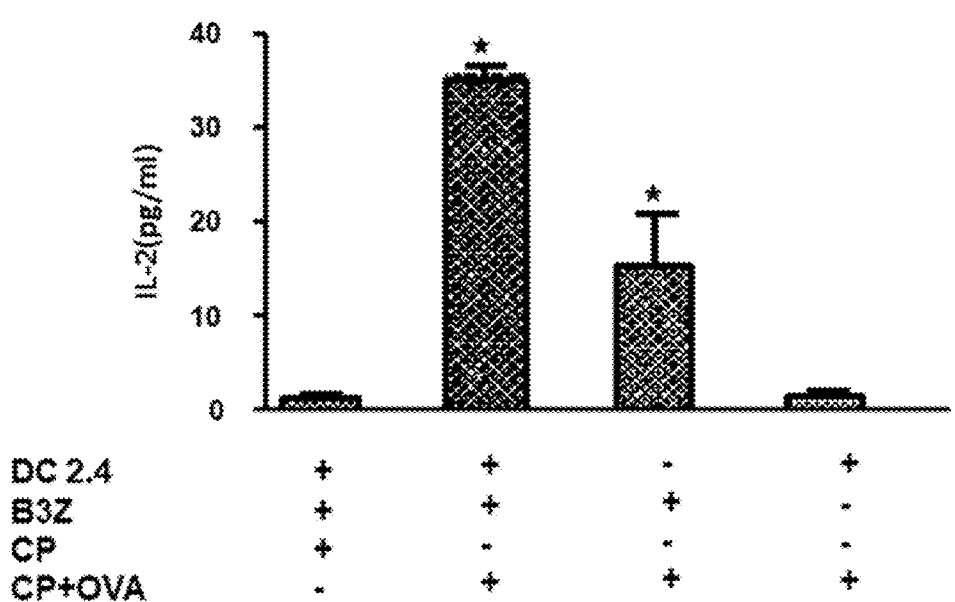
FIG. 2: Vault nanocapsules induce cross presentation to CD8 cells. B3Z cells ($1\times10^5$ cells/200 uL/well) were co cultured with DC 2.4 ($5\times10^4$ cells/200 μL/well) in the presence or absence of CP-OVA (3.3 μg/200 uL/well) for 24 hrs. Control vaults (CP) were also used at concentration of 3.3 μg/200 uL/well. Following 24 hrs, T cell activation was analyzed by measuring IL-2 production. Data in all panels are representative of 3 independent experiments. Student's t-test was used to determine statistical significance between the CP-OVA and control CP-vaults. *$p<0.05$.

Example 2: Ovalbumin Packaged Inside Vault Nanocapsules can Induce a MHC-I Restricted Response Dendritic cells (DCs) possess the unique ability to process particulate antigens efficiently into the MHC-I pathway, in a process known as cross-priming. Several approaches have been used to encourage cross priming such as adding exogenous antigenic proteins or peptides with adjuvants to stimulate cytotoxic T lymphocytes (CTLs) [35]. Therefore, we investigated whether recombinant vaults engineered to express OVA could be efficiently internalized, processed and presented by DC in an MHC-I restricted manner to activate CD8$^+$ T cells. To this end, the DC2.4 cell line (H-2K$^b$) was pulsed with CP-OVA and secretion of IL-2 was measured as an activation marker of the OVA-responsive CD8$^+$ T cell hybridoma B3Z (H-2K$^b$). The combination of DC2.4 cells, B3Z cells and CP that did not contain OVA-INT could not effectively stimulate IL-2 secretion. However, CP-OVA (produced by combining CP+OVA-INT) incubated with both DC2.4 cells and B3Z hybridoma cells induced secretion of IL-2 (FIG. 2). We examined different concentrations of CP-OVA vaults and determined that 3.3 µg CP-OVA vaults per 200 µL per well gave us the greatest IL-2 secretion (data not shown). Additional controls included the B3Z CD8+ T cell hybridoma incubated with CP-OVA alone which induced modest IL-2 levels and suggests that vaults interact with T cells and participate in autopresentation of MHC-I responses [36]. Finally, incubation of CP-OVA vaults with the DC2.4 cell line only produced baseline levels of IL-2. We concluded that exogenous antigen packaged within vault nanocapsules could be delivered and presented by the MHC-I pathway in DCs and possibly through autopresentation to enhance T cell responses.

Figure 3:
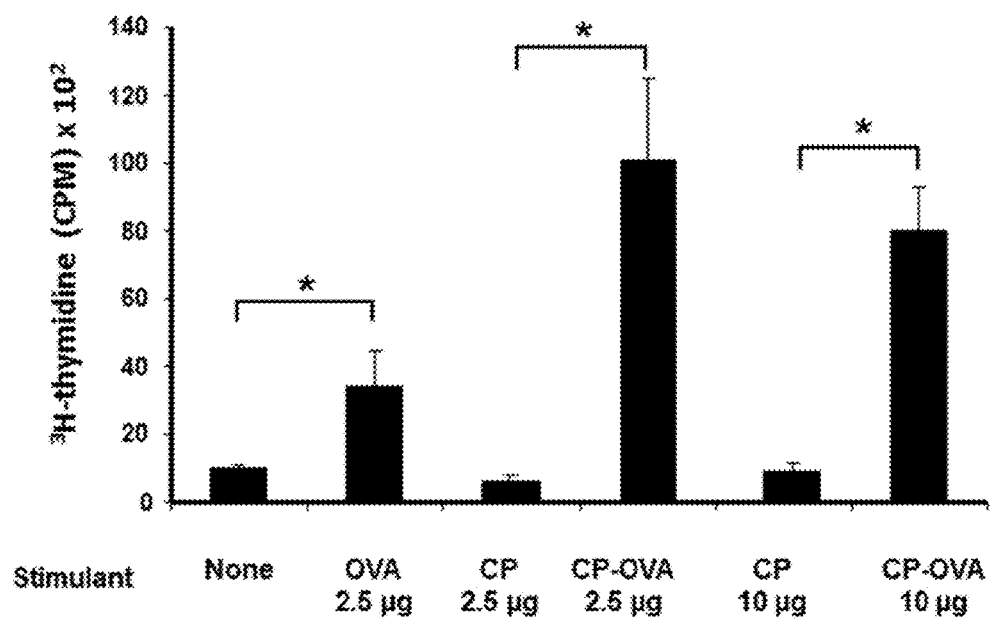
FIG. 3: Vault nanocapsules induce CD4 T cell activation. T cells ($2\times10^5$ cells/mL) were co-cultured with DC ($2\times10^4$ cells/mL) in the presence of PBS, recombinant OVA protein (2.5 μg/mL), control CP-vaults and CP-OVA with the indicated concentrations. DC-induced T cell proliferation was assessed by incorporation of [$^3$H] thymidine. The graphs show mean (SEM) values from a representative experiment (n=6 replicates) of three independent experiments. Student's t test was used to determine the p value by comparing appropriate control. *$p<0.05$.

Example 3: Ovalbumin Packaged Inside Vault Nanocapsules can Induce a MHC-II Restricted Response We also examined the MHC class II pathway using bone-marrow-derived DCs from syngeneic BALB/c (H-2 IA/E$^d$) mice pulsed with CP-OVA for 24 hours. These DCs were then used to stimulate naive OVA-responsive CD4$^+$ T cells from DO11.10 (H-2 A/E$^d$) mice. D11.10 cells are transgenic for the TCR recognizing the amino acid 323-339 peptide of OVA on MHC-II. As shown in FIG. 3, DC induced significant proliferation in the presence of OVA. However, OVA encased in vault nanoparticles at two concentrations; 2.5 µg and 10.0 µg, stimulated a greater degree of T cell proliferation at both concentrations compared to recombinant OVA protein alone and were not statistically different from each other (FIG. 3). These data show that OVA encased in vault nanocapsules was more effective at inducing CD4$^+$ T cell proliferation than soluble OVA.

Figure 4:
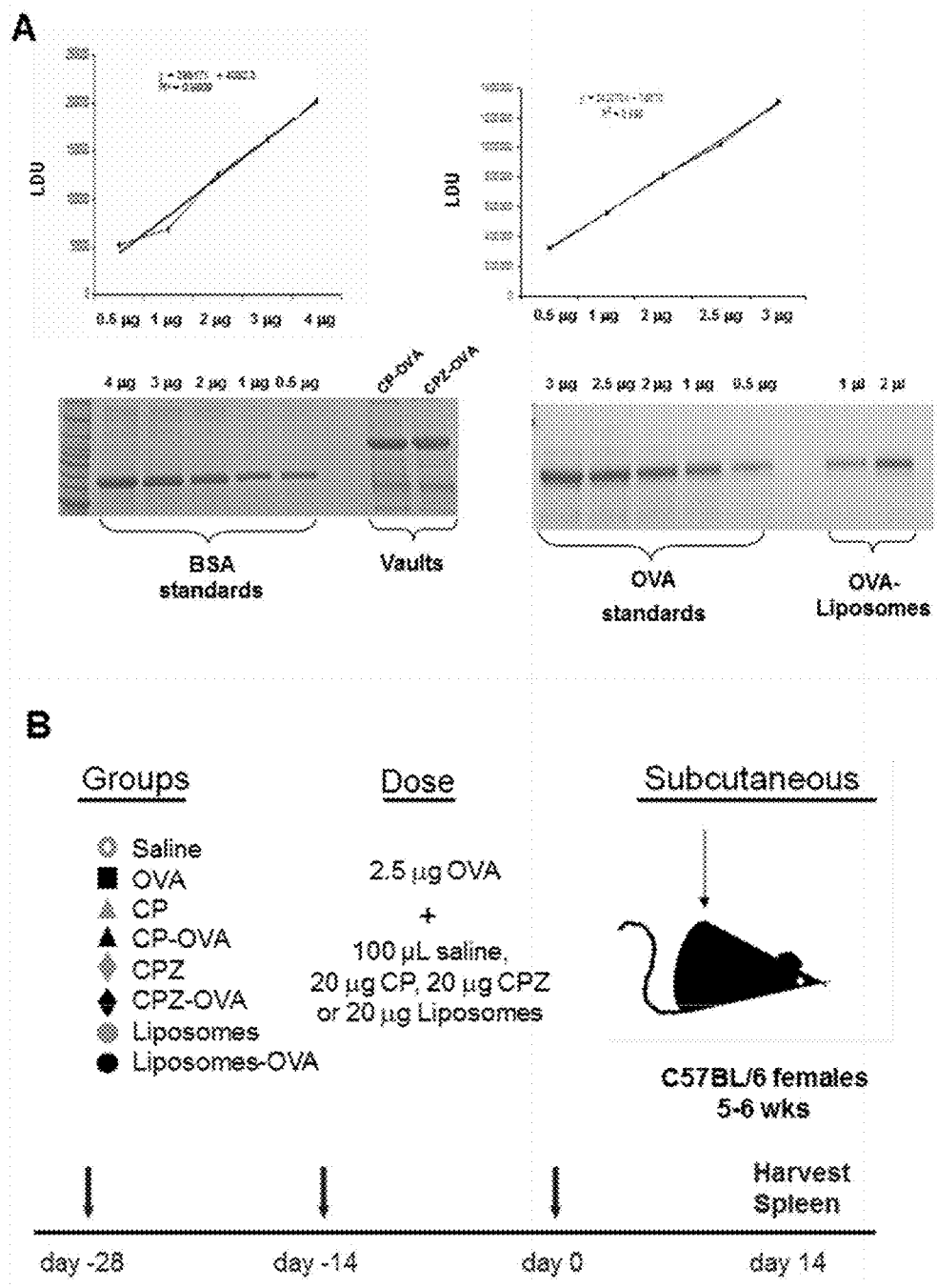
FIG. 4. Quantitation of OVA in delivery vehicles and immunization regimen. (A) Images of representative 4-15% SDS polyacrylamide gel showing standards, CP-OVA, CPZ-OVA and OVA-liposomes. The amount of OVA incorporated into the delivery vehicles were quantitated using a Typhoon 9410 Typhoon Variable Mode Scanner of Coomassie blue stained SDS-PAGE gels. (B) Schematic representation of vaccination schedules and subcutaneous immunizations with saline (✷), unencapsulated OVA with saline (■), CP (▲), CP-OVA (▲), CPZ (✦), CPZ-OVA (♦), liposome (✷) or liposome-OVA (●). The immunization regimen involved three vaccinations (day −28, −14 and 0).

Example 4: Vaccination of Mice with OVA Packaged Vault Nanocapsules Induces CD8$^+$ and CD4$^+$ T Cells in Vivo We characterized cell- and antibody-mediated immune responses to OVA encapsulated in vault nanocapsules and liposomes in vivo following subcutaneous administration. To evaluate the type of immune response we immunized mice with either CP-OVA or CPZ-OVA vaults containing equal amounts of endotoxin-free OVA (see material and methods). Liposomes where chosen as a control delivery method since they are a class of nanocarriers and have been utilized as delivery systems for drugs, peptides, proteins and DNA [29,37]. Liposomes are microscopic vesicles consisting of phospholipid bilayers which surround aqueous compartments and were prepared in this study by encapsulating OVA in DOTAP/DOPE as described in the methods section [38]. The amount of OVA within the vaults and liposomes was quantitated by SDS gel quantitation (FIG. 4A). Mice were immunized with equal amounts of delivery vehicle and OVA and the immunization regimen is described in FIG. 4B. The percentage of T cells responsive to the OVA CD8 peptide (SIINFEKL (SEQ ID NO:17)) or the OVA CD4 peptide 265-280 (TEWTSSNVMEERKIKV (SEQ ID NO:18)) were documented by surface, intracellular cytokine or perforin staining and FACS analysis after stimulation with each OVA peptide in C57BL/6 mice (H2$^b$ background) as described in the methods section. We also examined the anti-OVA-antibody responses following immunization by ELISA.

Figure 5:
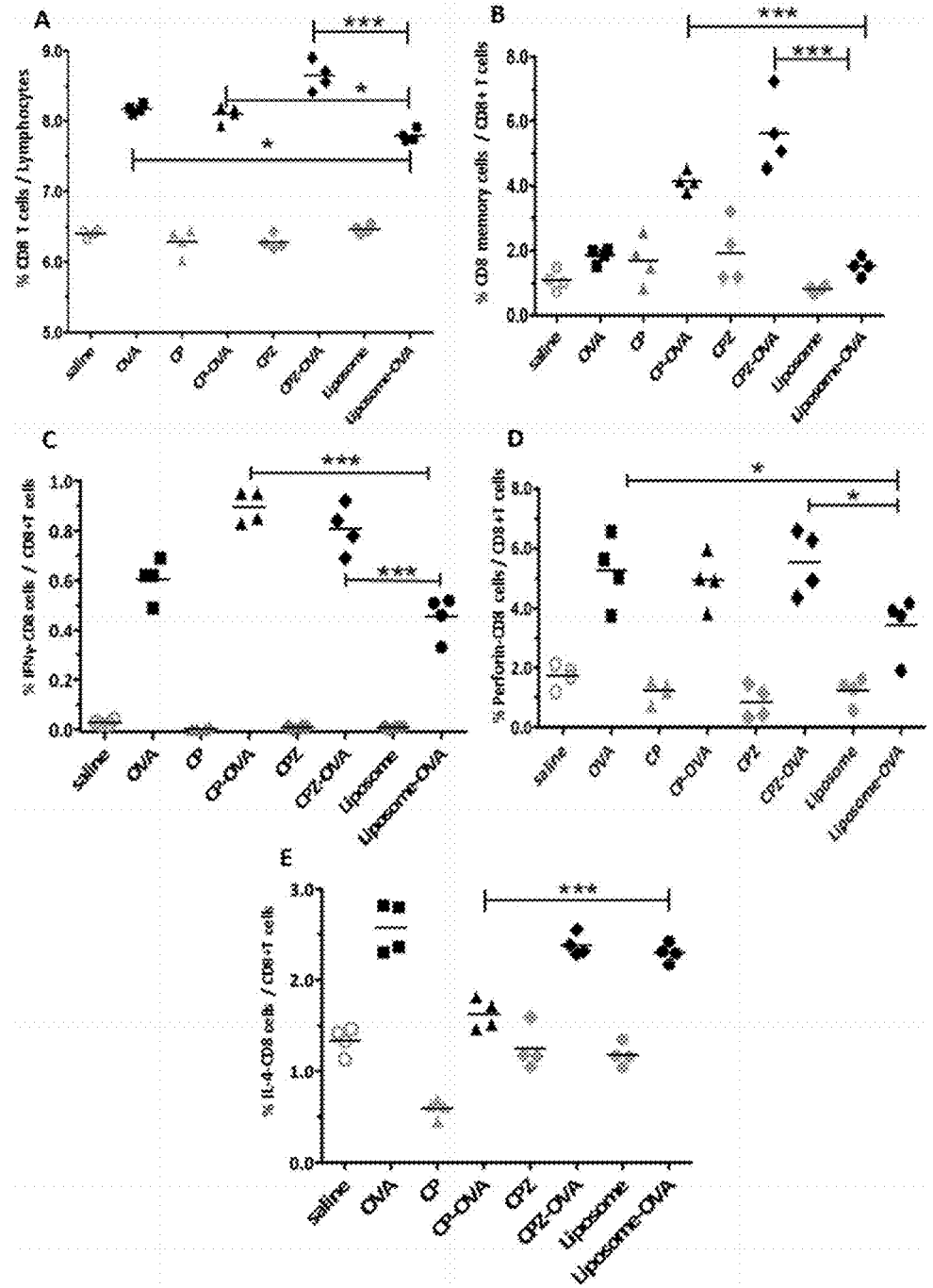
FIG. 5: Vault nanocapsules enhance priming of endogenous CD8+ T cells. Mice were injected with various immunogens as shown on the x-axis; saline (✷), unencapsulated OVA with saline (■), CP (▲) CP-OVA (▲), CPZ (✦), CPZ-OVA (♦), liposome (✷), or liposome-OVA (●). Splenocytes were harvested, stained and gated on lymphocytes as described in the methods section. The frequency of CD8 subpopulations are shown on the y-axis. (A) Total CD8+ cells, (B) CD8+ memory cells (CD8+CD44$^{hi}$), (C) IFNγ-producing CD8+ cells, (D) Perforin-expressing CD8+ cells and (E) IL-4 producing CD8 cells. The cell populations from immunized groups were compared using one-way ANOVA and Bonferroni's post-hoc test). *p<0.001, p<0.01, *p<0.05. Representative of 3 independent experiments.

CD8+ T cells play a critical role in protection against viral and intracellular bacterial and protozoan infections and are important in tumor and graft rejection [39]. After activation, naive antigen (Ag)-responsive CD8$^+$ T cells are able to proliferate quickly and differentiate into potent effector cells capable of rapid cytokine production and cytolytic killing of target cells [40,41]. We wanted to see if entrapment of OVA in vault nanocapsules facilitated cross-presentation of Ag to the MHC-I pathway, resulting in activation of a potent CD8$^+$ T cell immunity in vivo as we observed previously in vitro. We evaluated induction of CD8$^+$ T-cell responses among mice immunized with OVA-vaults (CP-OVA and CPZ-OVA), empty vaults (CP and CPZ) and Liposome-OVA as shown in FIG. 5. Control groups included soluble OVA and saline immunization. The induction of effector CD8$^+$ T cell responses in the spleen was measured 2 weeks after the last immunization by measuring the number of total CD8$^+$ T cells, CD8$^+$ memory T cells (CD44$^{hi}$), expression of the cytolytic marker perforin, and the production of IFNγ and IL-4 after stimulation with the H2$^b$ restricted CD8 OVA peptide, SIINFEKL (SEQ ID NO:17). All experimental controls were elevated over their respective controls. To simplify the graphs we only show statistical results for comparison of our control immunization group (Liposome-OVA) to the other OVA immunization groups. Our "control" group was Liposome-OVA group because we were interested to learn how vault immunization differed from liposome immunization.

As shown in FIG. 5A, we found a marked in increase of OVA-responsive SIINFEKL (SEQ ID NO:17) CD8$^+$ T cells in the CPZ-OVA immunized group over that found in Liposome-OVA immunized mice in the lymphoid compartment. It was surprising that total CD8$^+$ responses were only slightly elevated in the OVA and CP-OVA group and suggested that CD8$^+$ T cell subset examination may be more revealing than examining total CD8$^+$ T cells in the lymphoid compartment. We also saw an increase in CD8$^+$ memory T cells (FIG. 5B) and CD8$^+$ IFNγ producing T cells (FIG. 5C) in mice immunized with OVA encased vault nanocapsules compared to OVA delivered in liposomes while OVA immunization in saline did not increase these responses compared to the Liposome-OVA group. This is consistent with previous studies finding that OVA alone and liposome delivery does not enhance memory CD8$^+$ cytotoxic T cells [42]. Although we noted an increase in the number of CD8$^+$ T cells expressing perforin in CPZ-OVA immunized mice compared to Liposome-OVA immunized mice we also found increased CD8$^+$ perforin$^-$ T cells in the OVA group but no increase in the CP-OVA immunized mice. Interestingly, the number of IL-4 producing cells in CP-OVA immunized mice had markedly lower numbers compared to other OVA immunized groups. As expected, vaccination with OVA in any delivery vehicle or dissolved in saline significantly increased SINFEKL (SEQ ID NO:17)-responsive CD8$^+$ T cells over control groups for all immunization groups (FIG. 5). These findings demonstrate that immunization of antigen encased within vaults is cross-presented in vivo and stimulates a CD8$^+$ T cell response characterized by memory T cells and IFNγ producing T cells.

It has been documented that CD4$^-$ T cell help is important for CD8$^+$ T cell function. Since we observed increased numbers of OVA-responsive CD8$^+$ memory and IFNγ producing T cells in CP- and CPZ-OVA immunized mice, we investigated if the number of CD4$^+$ T cells was also increased following vault immunization. To address this issue, splenocytes from each group were stimulated ex vivo with the class II peptide, OVA 265-280 and the CD4$^+$ T cell response was characterized by FACS.

Figure 6:
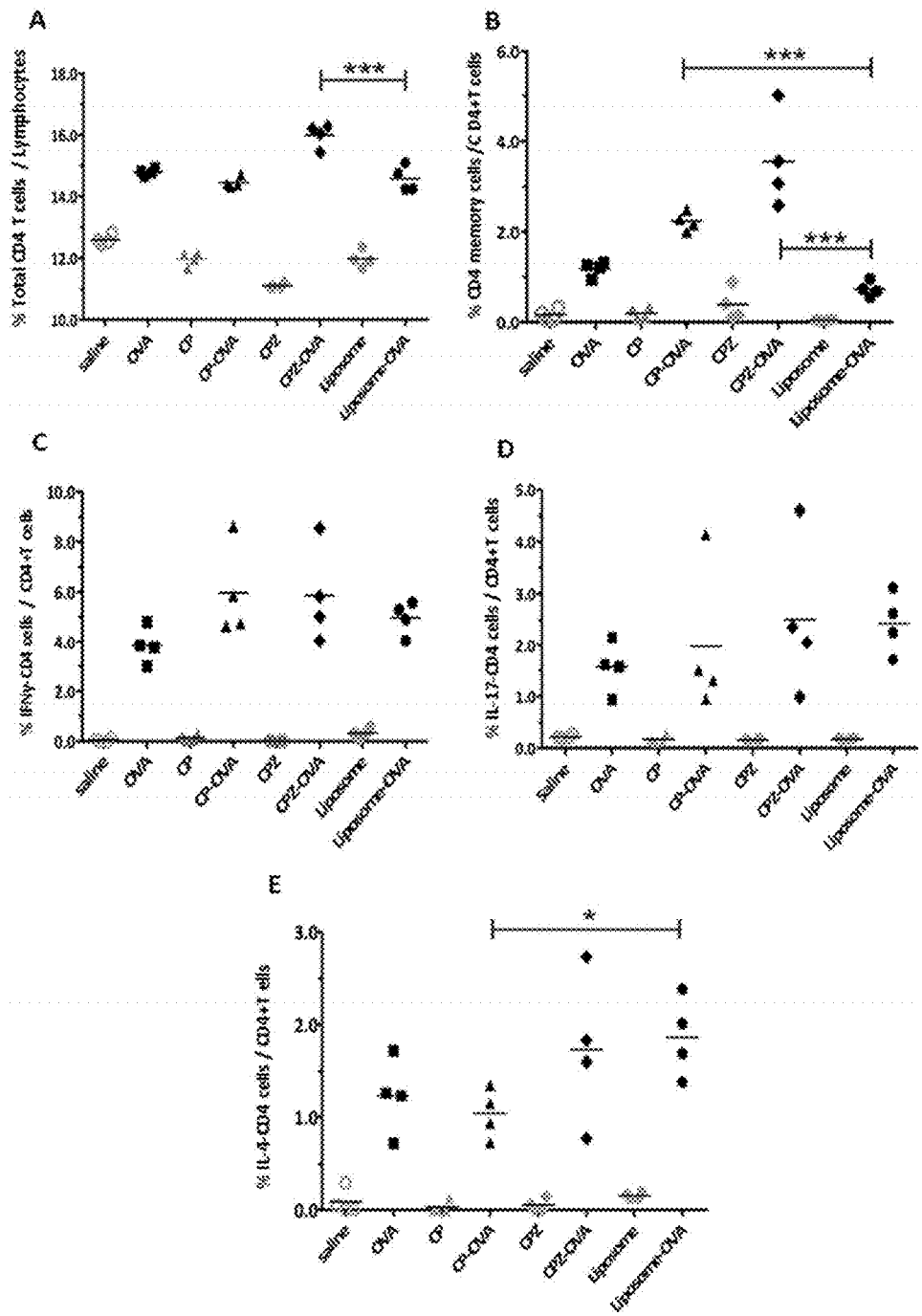
FIG. 6. Vault nanocapsules encourage production of CD4+ T cells upon vaccination. Mice were injected with various immunogens as shown on the x-axis; saline (⊛), unencapsulated OVA with saline (■), CP (▦), CP-OVA (▲), CPZ (✴), CPZ-OVA (♦), liposome (⊛), or liposome-OVA (●). Splenocytes were harvested, stained and gated on lymphocytes as described in the methods section. The frequency of CD4 subpopulations are shown on the y-axis. (A) Total CD4+ cells, (B) CD4+ memory cells (CD4+CD44$^{hi}$), (C) IFNγ-producing CD4+ cells, (D) IL-17 producing CD4+ cells and (E) IL-4 producing CD4 cells. The cell populations from immunized groups were compared using one-way ANOVA and Bonferroni's post-hoc test). *p<0.001, p<0.01, *p<0.05. Representative of 2 independent experiments.

We found that immunization with CPZ-OVA but not CP-OVA vault nanocapsules induced a significant amount of total CD4$^+$ T cells in the lymphoid compartment of the spleen when compared to Liposome-OVA group (FIG. 6A). Also, immunization with both forms of vault nanocapsules significantly elevated the number of CD4$^-$ memory T cells compared to Liposome-OVA immunized mice (FIG. 6B). We did not see a significant increase in IFNγ or IL-17 producing CD4$^+$ T cells over that seen in Liposome-OVA immunized mice following vault or liposome immunization of OVA (FIGS. 6C & D). However, CPZ-OVA but not CP-OVA immunization induced similar numbers of IL-4 producing CD4+ T cells as mice immunized with Liposome-OVA (FIG. 6E). We also noted significant increases in subsets as well as total CD4$^+$ T cells in all immunized groups when compared to control groups as expected (FIG. 6). Taken together, these data show that immunization with CPZ-OVA induces CD4$^+$ T cells characterized by memory cells and IL-4 producing cells. Immunization with CPZ vaults results in the combination CD8$^+$ T cells and CD4$^+$ helper T cells.

Figure 7:
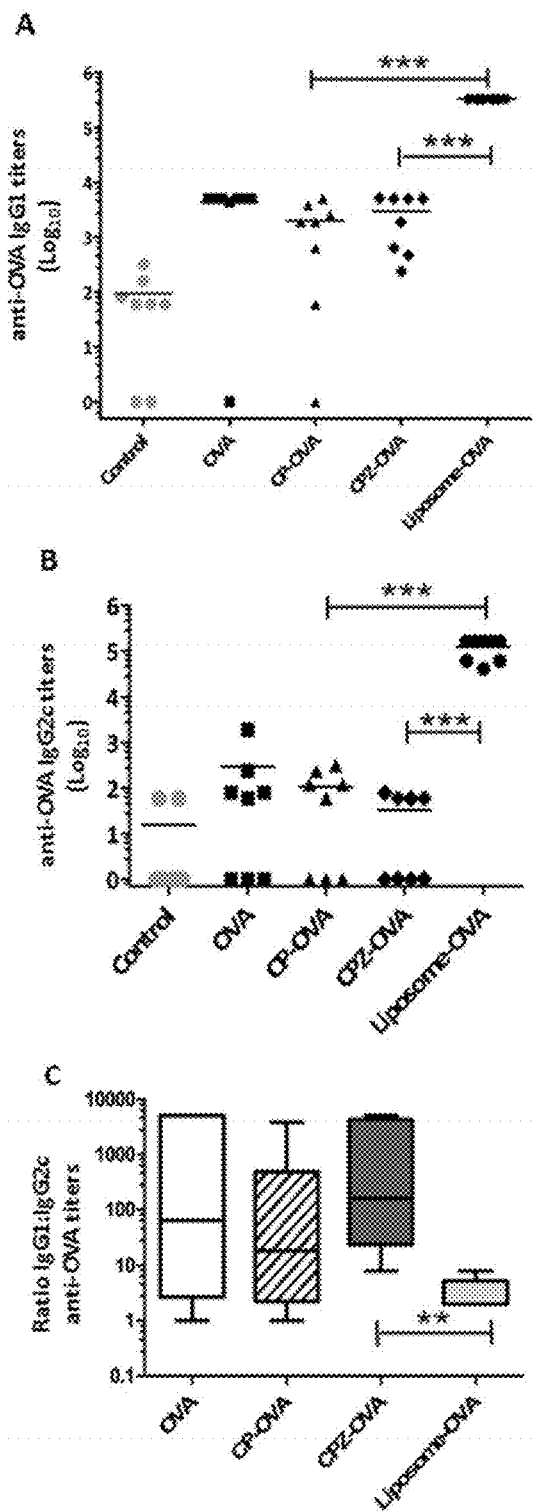
FIG. 7: Vault nanocapsules produce lower anti-OVA antibody titers. Antibody titers after vaccination schedule, composed of 3 weekly s.c. injections with control saline (⊛), unencapsulated OVA in saline (■), CP-OVA (▲), CPZ-OVA (♦) or Liposome-OVA (●). (A) Total anti-OVA-IgG1 titers and (B) Total anti-OVA-IgG2c titers. Significance was determined by ANOVA (p<0.001) with Bonferroni post-hoc test (***p<0.001). (C) Ratio of anti-OVA IgG1 to IgG2c antibody. The ratio of Liposome-OVA immunized mice were compared to the other OVA-immunized groups using Mann Whitney t-test (*p<0.001). Data are representative of 2 independent experiments.
Figure 8:
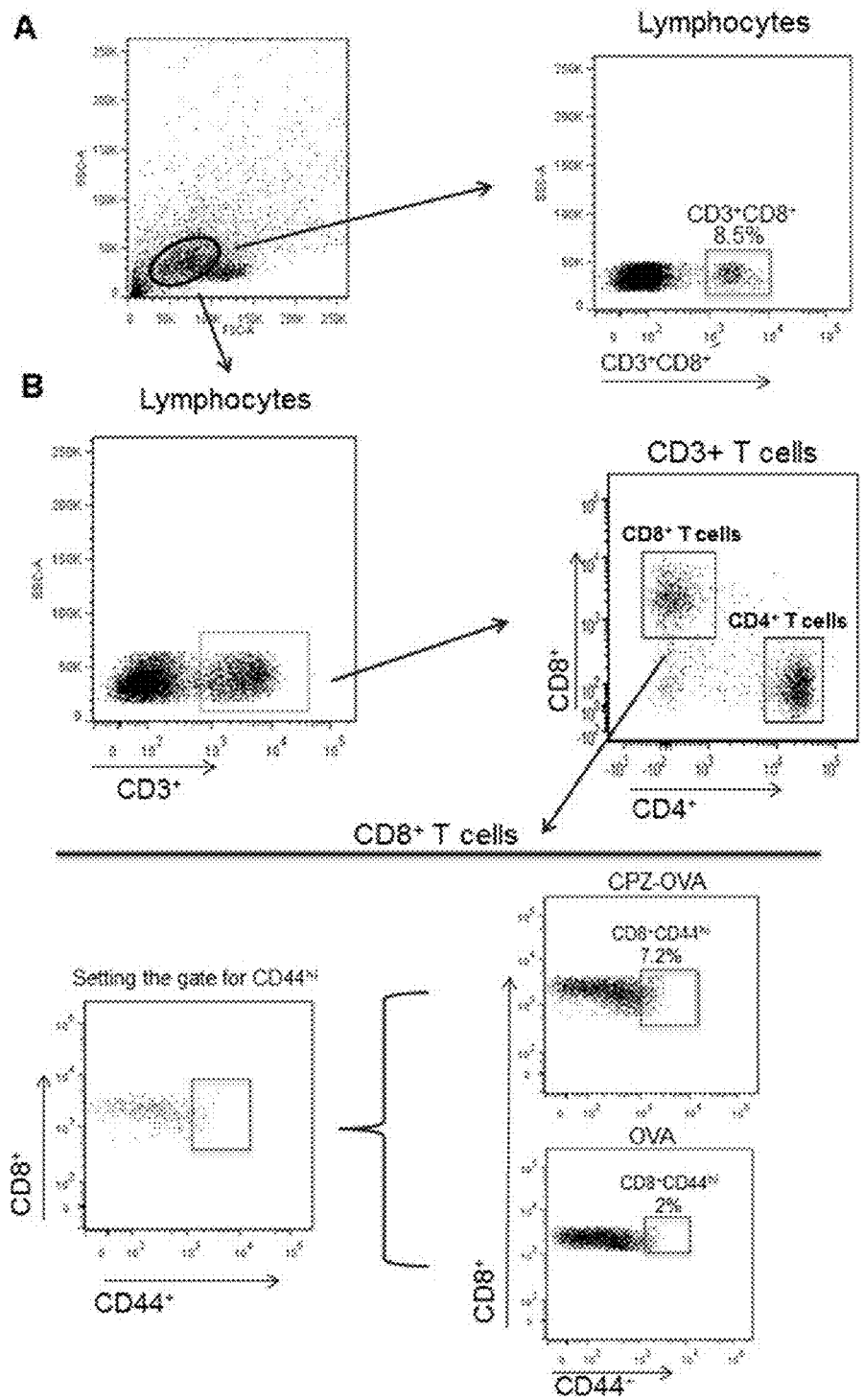
FIG. 8: Flow cytometry gating scheme used to define cell populations. (A) A representative dotplot from a CPZ-OVA immunized mouse was gated on lymphocytes using SSC versus FSC. The percent of CD3$^+$CD8$^+$ memory T cells was determined from the events in the lymphocyte gate. (B) The lymphocyte gated population was further gated on CD3$^+$ T cells and CD3$^+$ T cells were separated into CD8$^+$ or CD4$^+$ T cells. Memory cell population was determined by hi expression of CD44 and a gate drawn. This was applied to all experimental mice to determine the percentage of CD8$^+$ memory cells. The scheme was applied to CD8$^+$ or CD4$^+$ T cells producing cytokines or expressing perforin by gating on the CD3$^+$CD8$^+$ or CD3$^+$CD4$^+$ population.

Example 5: Vault Nanocapsules can be Modified to Induce Select Antibody Ig Isotypes Co-operation of CD4$^+$ T helper cells with antigen specific B cells is crucial for inducing long-lived neutralizing antibody responses for protective immunity followed by vaccination [43]. We investigated whether OVA delivered in vault nanocapsules also induced anti-OVA antibody since they were capable of inducing CD4$^+$ T cell memory and IL-4 producing cells. The serum titers of OVA-responsive IgG1 and IgG2c in each group were measured after immunization by ELISA. We found that mice immunized with Liposome-OVA induced significantly greater levels of anti-OVA IgG1 and IgG2c compared to CP-OVA, CPZ-OVA or OVA immunized mice (FIGS. 7A & B) indicating that liposomes induce high levels of anti-OVA antibody [44-46]. Further inspection revealed that the addition of the "Z" domain reduced mean anti-OVA IgG2c titers by 0.5 to 1 log in comparison to CP-OVA and OVA groups while IgG1 remained comparable. Comparison of the ratio of anti-OVA IgG1:IgG2c revealed that Liposome-OVA immunized mice produced equal levels of IgG1 and IgG2c resulting in a ratio near one while immunization with CP-OVA, CPZ-OVA or OVA increased the ratio of IgG1:IgG2. Moreover, mice immunized with vault nanocapsules modified to express the "Z" domain (CPZ-OVA) had a significantly increased this ratio compared to Liposome-OVA immunized group. In contrast, the OVA and CP-OVA groups were not significantly different compared to the Liposome-OVA group (FIG. 7C). As expected all OVA immunization groups induced significant IgG1 and IgG2c serum antibody titers compared to the corresponding controls (FIG. 7). These data show that modification of the vault body by addition of the "Z" domain modifies the antibody isotype and suggests that the vault nanocapsule can be modified to alter the humoral responses.

Example 6: Use of Vault Particles as an Adjuvant to Deliver an Antigen

When the vault particle is used as an adjuvant to deliver the model antigen ovalbumin (OVA) to mice harboring the solid tumor produced from Lewis lung carcinoma cells engineered to express ovalbumin, a cellular immune response directed against the tumor is induced resulting in immune attack on the tumor itself leading to reduction in the tumor size. This antitumor immune response can be induced with a contralateral subcutaneous injection of the vault encapsulated ovalbumin with equal efficacy. See FIGS. 9A and B and 10A and B.

Example 7: Use of CCL21 Chemokine Containing Vault Particles to Activate an Antitumor Response The antitumor immune response to the vault adjuvant engineered to deliver specific antigens can be further activated by vault particles containing the CCL21 chemokine. See FIGS. 11 A and B and Table 2.

As one embodiment of this invention, the CCL21-vault can be combined with one or more than one vault containing tumor antigens to increase the cellular immune response induced toward the tumor. See FIG. 11A and Table 2.

Example 8: Use of Vault Particles to Deliver the Tumor Antigens

When the vault particle is used as an adjuvant to deliver the tumor antigen NYESO1 to mice harboring the solid tumor produced from Lewis lung carcinoma cells engineered to express NYESO1, immune responses directed against the tumor are induced resulting in immune attack on the tumor itself. This antitumor immune response can be induced with a contralateral subcutaneous injection of the vault encapsulated NYESO. See FIGS. 12A and B.

Figure 13:
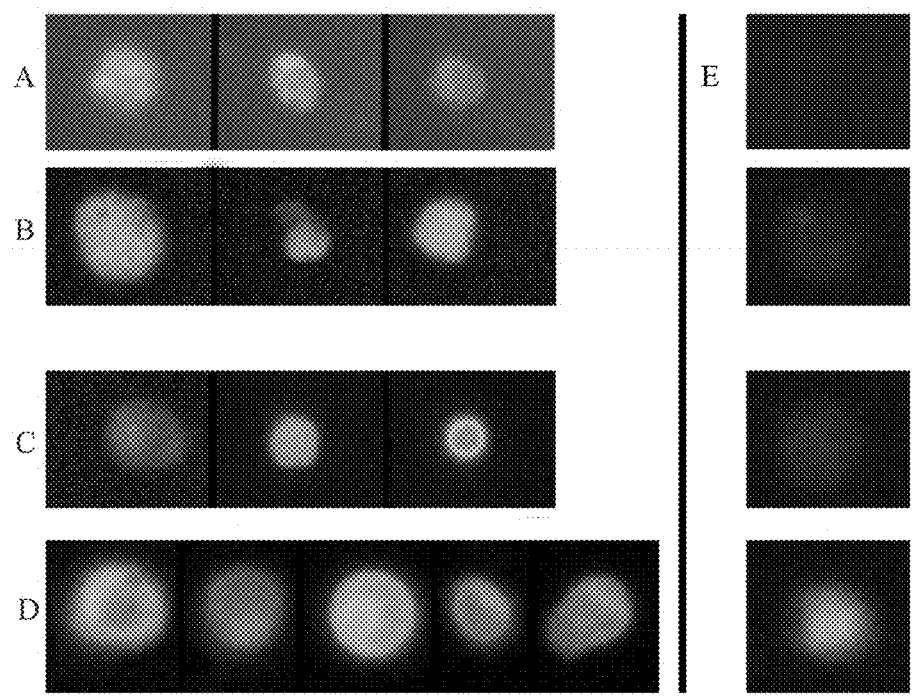
FIG. 13: Efficient uptake of vault nanoparticles housing NYESO by dentritic cells. Fluorescent microscopy images demonstrating DC integration of INT vaults. DCs stained in green with either media alone or our vaults stained in red. At zero minutes and T60 for the media (A and B), autofluorescence surrounding the exterior of the DC. After 60 minutes of incubation with vaults, clear concentration of vaults within the confines of the DCs (C and D). Vaults stained in red are shown in media (top) and integrated in a DC (bottom) (E).

These results have also been extended to glioblastoma by packaging the glioblastoma associated antigens (GAA): GP100, EGFRv3, NY-ESO, and TRP-2 onto the INT domain. All GAA-INT fusion proteins have been packaged into CP, CPZ, or pVIZ vaults. Vault nanoparticles housing NY-ESO have been shown efficient uptake by dendritic cells. See FIG. 13.

Figure 14:
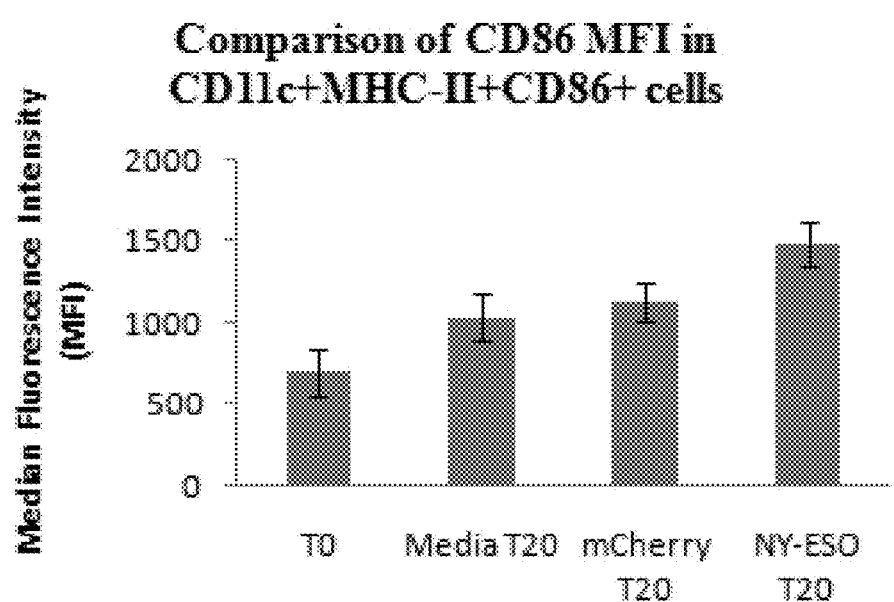
FIG. 14: Increased dentritic cell activation and maturation as measured by CD86 expression by treatment with NYESO vaults. Flow cytometry for DC maturation following 20 hours of incubation with NY-ESO-1 vaults, vaults with a red fluorescent protein, or media alone. CD86 median fluorescence intensity for the NY-ESO-1 vaults demonstrated a statistically significant 43% increase in MFI.

Furthermore, dendritic cell activation and maturation as measured by CD86 expression has also been shown to be significantly increased by treatment with NY-ESO vaults. See FIG. 14.

Figure 15:
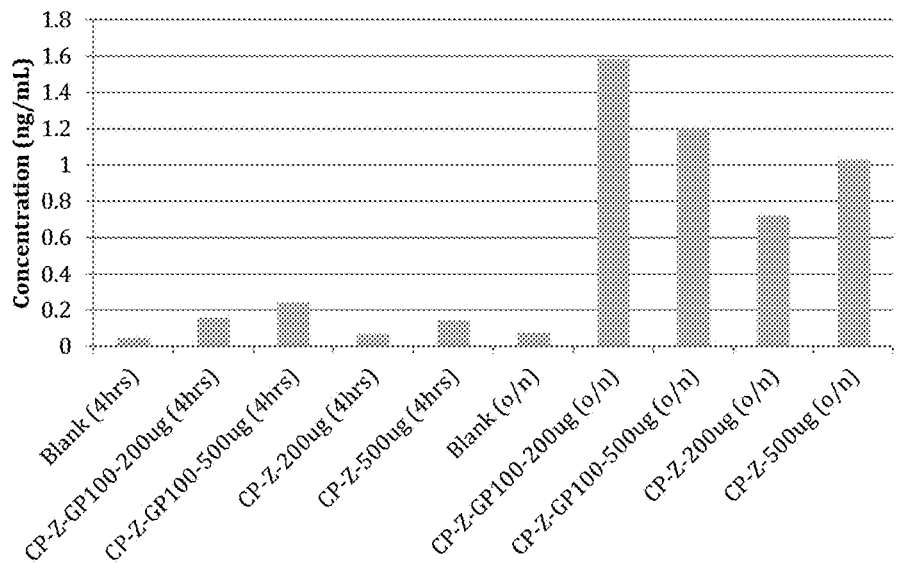
FIG. 15: Dendritic cells treated with GP100 vaults have demonstrated efficacy in stimulating CD8 T cells as shown by elevated levels of interferon gamma. In vitro ELISA demonstrating a significant increase in interferon gamma in T cells incubated with dendritic cells treated with GP100 vaults at 4 hours and for 24 hours.

Additionally, dendritic cells treated with GP100 vaults have demonstrated efficacy in stimulating CD8 T cells shown by elevated levels of interferon gamma. See FIG. 15.

Example 9: Use of Vault Particle Delivery of Tumor Antigens for Personalized Therapeutics The compositions and methods disclosed herein can be utilized for personalized therapeutics directed against a wide variety of tumors. For example a biopsy of a particular tumor (lung glioblastoma etc.) can analyzed using existing procedures to determine the presence of common tumor antigens (biomarkers). Vault particles can be produced and engineered to contain individual tumor antigens and a mixture of these particles can be formulated based on the biopsy results of an individual tumor. This mixture of vault particles can then be used to immunize the patient and stimulate a specific cellular immune response that will be directed against the patient's particular tumor.

In other words, in lung cancer there are approximately 10 to 15 different antigens (tumor biomarkers) that are primarily expressed in nearly 99% of all lung tumors. Each of these 10 to 15 different antigens can be produced as fusion proteins with the vault packaging domain INT (antigen 1-INT, antigen 2-INT, antigen 3-INT etc.). These 10 to 15 different antigens-INT fusion proteins can be expressed, purified and stored either separately or mixed with recombinant vaults to form individual vault adjuvant antigen preparations that can be stored. Following biopsy, an individual's lung tumor can be analyzed for expression of the presence of the common biomarkers (the 10 to 15 different antigens) that are present in that tumor, thus allowing for tailored treatments for tumor eradication. For this example we will assume that antigens 3, 5 and 9 are present in an individual's tumor. A formulation of three different vault preparations (vaults containing antigen 3-INT, plus vaults containing antigen 5-INT plus vaults containing antigen 9-INT) can then be administered by subcutaneous injection to induce a cellular immune response to the individual tumor.

Example 10: Methods and Materials

Expression and Purification of Recombinant Vaults

Recombinant baculoviruses were generated using the Bac-to-Bac protocol (Invitrogen, Carlsbad, Calif.). The 385 amino acid coding region of ovalbumin was fused to major vault protein interaction domain (INT) derived from VPARP (amino acids 1563-1724) by PCR ligation[52,53]. Two PCR reactions were carried out: first=OVA-forward: CCCCACTAGTCCATGGGCTCCATCGG (SEQ ID NO:19) and OVA-INT reverse: TCCTGCCAGTGTTGTGT-GCAGCTAGCAGGGGAAACACATCTGCC (SEQ ID NO:20) using plasmid pMFG-OVA as the template (plasmid pMFG-OVA was a kind gift from Dr Carlo Heirman, Laboratory of Molecular and Cellular Therapy, Department of Physiology—Immunology, Medical School of the Vrije Universiteit Brussel, Brussels, Belgium). The second PCR reaction with primer OVA-INT forward: TTGGCAGATGT-GTTTCCCCTGCTAGCTGC ACACAACACTGGCAGGA (SEQ ID NO:21) and INT reverse: GGGCTCGAGTTAGC-CTTGACTGTAATGGAG (SEQ ID NO:22) using INT in pET28 as the template. The PCR reactions were purified on a Qiagen column and a second round of PCR was carried out using the OVA-forward x INT reverse. The resultant PCR product containing the fused OVA-INT was purified on a Qiagen column, digested with Spe I and Xho I, gel purified, and ligated to pFastBac to form a pFastBac vector containing OVA-INT. Construction of cp-MVP-z, or cp-MVP in pFastBac has been described previously [32].

Sf9 cells were infected with Ova-INT, cp-MVP-z, or cp-MVP recombinant baculoviruses at a multiplicity of infection (MOI) of 0.01 for approximately 65 h and then pelleted and lysed on ice in buffer A [50 mM Tris-HCl (pH 7.4), 75 mM NaCl, and 0.5 mM MgCl2] with 1% Triton X-100, 1 mM dithiothreitol, 0.5 mM µg/ml chymostatin, 5 µM leupeptin, 5 µM pepstatin) (Sigma, St. Louis, Mo.). Lysates containing cp-MVP-z vaults were mixed with lysates containing either OVA-INT were incubated on ice for 30 min to allow the INT fusion proteins to package inside of vaults. Recombinant vaults were purified as previously described[33] and resuspended in 100-200 µl of sterile phosphate buffered saline. The protein concentration was determined using the BCA assay (Pierce, Rockville, Ill.) and sample integrity was analyzed by negative stain electron microscopy and SDS-PAGE with Coomassie staining or transferred to hybond membrane (Amersham) for Western blot analysis. The density of the bands was determined by gel scanning and densitometry analysis using a 9410 Typhoon Variable Mode Scanner (GE Healthcare Life Sciences, Piscataway, N.J.).

Preparation of OVA-Liposomes

To generate OVA-liposomes, 10 mg lyophilized DOTAP/DOPE (1:1) (1,2-dioleoyl-3-trimethylammonium-propane/1,2-dioleoyl-sn-glycero-3-phospho-ethanolamine) (Avanti Polar Lipids, Alabaster, Ala.) was re-hydrated in 1 mL endotoxin-free 5% glucose and mixed slowly (rotated) overnight at room temperature. Lyophilized EndoGrade Ovalbumin (<1 EU/mg=1 endotoxin unit has ~0.1 ng of endotoxin) (Profos AG, BioVender, LLC, Candler, N.C.) was reconstituted in endotoxin-free sterile saline (<0.1 EU/mL endotoxin, Sigma) to a stock solution of 10 mg/mL. Aliquots were stored frozen and thawed immediately before use. The entrapment of OVA was generated by combining 1.25 mg of resuspended ovalbumin with 2.5 mg of swollen DOTAP/DOPE lipids and further facilitated by brief sonication. OVA-liposomes were separated from unincorporated ovalbumin by ultracentrifugation at 100,000×g using an Optima XL-80K (Beckman Coulter, Fullerton, Calif.) ultracentrifuge and washed two additional times. Quantitation of encapsulated OVA was determined by subjecting OVA-liposomes (1, 2, 4 µL) to SDS-PAGE electrophoresis in parallel with known amounts of ovalbumin (0.25, 0.5, 1.0, 2.5, 5 µg) and visualized by Coomassie blue staining.

Gel Electrophoresis and Immunoblotting

Sodium dodecyl sulfate-polyacrylamide gel electrophoresis was performed using the discontinuous buffer system and 4-15% acrylamide gels. Protein samples of OVA-liposome or OVA-vaults were transferred to an Immobilon-P transfer membrane (Millipore, city, Bedford, Mass.) and blocked with 5% (wt/vol) nonfat dry milk in PBS-0.1% Tween 20 (PBS-T). Membranes were incubated for 1 hr with anti-MVP (1:500, MAB 1023, Santa Cruz Biotechnology Inc, Santa Cruz, Calif.) or anti-INT followed by a 1 h incubation with the appropriate horseradish conjugate (1:5,000, Amersham Biosciences, Piscataway, N.J.). Bound conjugates were detected with ECL-Plus (GE Healthcare, Life Sciences, Piscataway, N.J.) and 9410 Typhoon Variable Mode Scanner (GE Healthcare Life Sciences, Piscataway, N.J.).

Antigen Processing and Presentation Assay

DC2.4 H-2Kb ($5 \times 10^4$/well) were plated in triplicates in 96-well plates and allowed to settle at 37° C. Then, MHC Class I restricted CD8$^+$ T cell line B3Z ($10^5$/well) were added, in the presence of control vaults (200 ng/mL) and OVA vaults (200 ng/mL) for 24 hrs. After 24 h incubation at 37° C., the plate was centrifuged at 1800 rpm, and the culture supernatant was collected and assayed for IL-2 using an IL-2 ELISA kit (BD Biosciences, San Jose, Calif.).

DC-Dependent T Cell Proliferation

DC cultures were generated by flushing the bone marrow (BM) from the bone shafts, washed and plated bacteriological Petri dishes (Falcon Plastics, Oxnard, Calif.). The cells were cultured at $2 \times 10^5$ cells/mL in RPMI 1640 culture medium (10 mM HEPES/2 mM l-glutamine/10% 0.22 um filtered FBS/50 uM β-mercaptoethanol) supplemented with mGM-CSF (20 ng/mL) and mIL-4 (20 ng/mL) in an atmosphere of 5% $CO_2$ at 37° C. Fresh medium containing mGM-CSF (20 ng/mL) and mIL-4 (20 ng/mL) was added for 3-6 days after the start of culture. To induce maturation, cells were cultured for an additional 24 h in the presence of LPS (1 µg/mL). The DC were harvested and purified with anti-CD11c magnetic beads, and suspended in complete RPMI-1640 medium and seeded at $5 \times 10^5$/mL/well on 24-well culture plates followed by incubation with 25 and 100 µg/mL of CP-OVA or recombinant OVA protein for 4 h at 37° C., 5% $CO_2$. Nonadherent cells consisting of mostly immature or mature DC were harvested for all the analyses performed in this study. Responder CD4+ T cells were separated from splenocytes with mouse CD4+ T-cell enrichment system (StemCell Technologies, Vancouver, Canada) according to the manufacturer's instructions. CD4+ T cells ($2\times10^4$/well) were added to OVA protein or CP-OVA pulsed DC and cultured for an additional 4 days. During the last 16-18 h of the 4-day culture, cells were pulsed with 1 µCi [3H]thymidine (Amersham, Arlington, Ill.). The cells were harvested onto filter paper and [3H]thymidine incorporation was measured with a β-plate scintillation counter (PerkinElmer, Wellesley, Mass.).

Immunization Procedures

The OVA protein concentration was adjusted using endotoxin-free sterile saline (<0.1 EU/mL, 1 EU has ~0.1 of endotoxin (Sigma) to 2.5 µg OVA in 20 µg of vault nanoparticles or liposomes using a Typhoon 9410 Variable Mode Scanner of Coomassie blue stained SDS-PAGE gels. The immunogens were injected into C57BL/6 mice (5-6 wk old) by subcutaneous injections at the base of the neck in 100 µl sterile saline. The mice were immunized 3 times at 2 wk intervals. The spleen and blood was obtained 2 wk after the last immunization. The splenocytes were immediately used for FACS analysis and serum samples were stored frozen at −80° C. until assayed.

Measurement of Anti-OVA Antibody from Serum

An ELISA was used to determine the level of anti-OVA antibody isotypes in the serum. Briefly 96-well microtitre plates (Nunc, Roskilde, Denmark) were coated with 75 µl per well of OVA (1 µg/75 µl) in PBS and incubated over night at 4° C. After being washed in buffer (phosphate buffered saline containing 0.05% Tween-20 (v/v) (PBS/T20) the plates were blocked with 150 µl of PBS supplemented with 5% non-fat dry milk for 2 h at room temperature. After washing, 7 µl of serum diluted from 1:40 to 1:5120 in PBS was added and incubated at 4° C. overnight. Unbound antibody was then washed away and 75 µl of goat anti-mouse IgG1-IgG2c-biotin (Southern Biotechnology Associates, Inc., Birmingham, Ala.), diluted 1/10,000 in PBS, was added and the plates incubated for 4 h at room temperature. The plates were then washed and 75 µl of NeutraAvidin horse radish peroxidase diluted in PBS at 1:1000 was added for 20 min. After a final wash step, 100 mL of TetraMethylBenzidine (TMB) (Zymed Laboratories Inc., San Francisco, Calif.) substrate was added and incubated at room temperature, in the dark, for 20 min. The reaction was stopped with 50 µL of 2 N sulphuric acid and the plates were read at 450 nm in a microplate reader (Model 550, Bio-Rad Laboratories, Hercules, Calif.).

Measurement of IL-2 Production

Spleens were removed and placed in RPMI media (Gibco, Grand Island, N.Y.) supplemented with 10% heat inactivated FCS. They were macerated to release the lymphocytes which were then washed by centrifugation. The cell pellet was resuspended in fresh media at a concentration of $2\times10^6$ cells/mL and 1 mL of cells placed in each well of a 24-well plate (Nunc, Roskilde, Demark). They were restimulated with media (negative control) or OVA (100 µg/mL) for 72 h at 37° C. in a humidified atmosphere with 5% $CO_2$. The plate was frozen until required. One hundred microliters of the supernatants were tested for IL-2 in a sandwich ELISA following the manufacturer's instructions (PharMingen, San Diego, USA). In brief, 96-well, flat-bottomed plates were coated with 50 µL of a 2 µg/mL concentration of capture antibody (PharMingen). Plates were washed and blocked with 200 µL/well of PBS/FCS. Doubling dilutions of standards and supernatants were added and incubated at 4° C. overnight. The plates were washed and 100 µL of a biotin-conjugated detecting mAb (PharMingen) was added at a concentration of 1 mg/mL. The enzyme and substrate were then added and analyzed as per the serum antibody ELISA. The amount of each cytokine in the supernatant was extrapolated from the standard curve derived using recombinant IL-2 (PharMingen) standards.

Characterization of T Cell Populations by Flow Cytometry

Lymphocytes were isolated from spleens by mechanical disruption through a cell strainer. RBCs were lysed using ammonium chloride-potassium buffer. The cells were stimulated @37° C. with OVA peptide 265-280:TEWTSSNVMEERKIKV (SEQ ID NO: 18) (2 µg) to identify CD4 cells or OVA peptide: SIINFEKL (SEQ ID NO: 17) (2 µg) to identify CD8 cells for 5 hr. For the last 4 h, cells were incubated in the presence of Brefeldin A (BioLegend) at 1 µg/mL. At the end of culture, the cells were stained using fluorochrome-conjugated MAbs against CD3, CD8, CD4, CD44, CCR7 and CD62L (BioLegend, San Diego, Calif.) in staining buffer (PBS with 2% fetal bovine serum and 0.1% sodium azide) and then treated with Fix/Perm (BioLegend). After permeabilization, the cells were further stained with fluorochrome-conjugated antibodies against IFN-γ, IL-4, IL-17 and perforin. Data were collected on LSR II (BD Biosciences, San Jose, Calif.) and analyzed using FCS Express (De Novo Software, Los Angeles, Calif.). CD8+ and CD4+ T cells were determined by gating on lymphocytes (FSC vs SSC) and CD8+ or CD4+ memory, cytokine producing or perforin expressing T cells were determined by gating on either CD3+CD8+ or CD3+CD4+ T cells as shown in FIG. 51.

Statistical Analysis

Statistical analysis was performed using Prism 5 (GraphPad, San Diego, Calif.). Data are presented as mean for each group and statistical significance for IL-2 secretion, proliferation, flow cytometry and Ig titers were determined by one way analysis of variance (ANOVA) with Bonferroni's Multiple Comparison Test. The ratio of isotypes was compared by Kruskal-Walis and Dunn's post-test.

Discussion

The work presented here illustrates the potential of engineered vault nanocapsules to act as potent adjuvants for the induction of combined cellular and humoral immune responses. Overall, our results demonstrate that immunization of OVA encased in vault nanocapsules, was more effective at generating greater cellular immunity characterized by increased numbers of OVA responsive memory CD8− and CD4+ T cells. Also, modification of the vault body, by addition of the "Z" domain, altered the level of anti-OVA Ig subclass as shown by an increased IgG1:IgG2C ratio. These findings show that immune responses against OVA induced by vault nanoparticles differ compared to those induced by liposomes.

An important feature of vault nanocapsules as adjuvants is the robust induction of CD8+ and CD4+ memory T cells. The delivery of antigens to antigen presenting cells, especially DC, is a critical step for initiating and regulating the adaptive immune responses and we have shown that DC efficiently internalize vault nanocapules [27,41]. We have also shown that vaults containing immunogenic proteins activate inflammasomes and escape into the cytoplasm [unpublished data, [27]. This may explain induction of an OVA-responsive CD8+ memory T cell response and cross-presentation. Vaults may also stimulate antigen-responsive CD8+ and CD4+ memory T cells by acting as intracellular depots or altering JAK/STAT signaling [47].

A potential vaccine should have the ability to induce and maintain antigen-responsive effector and/or memory T cells [7]. Our data show that immunization with vault nanocapsules was capable of inducing phenotypic markers of memory cells in CD8⁻ and CD4⁺ T cells. It will be interesting to extend these studies and examine memory responses in vivo using protection from infection or tumor models. In addition, we found enhanced production of OVA-responsive CD8⁺ T cells that could secrete IFNγ. Surprisingly, there was not much difference between Liposome-OVA and OVA immunized groups and one questions the present of LPS. We did not measure LPS concentrations directly but all reagents used were endotoxin free and the purchased OVA was endotoxin free (see methods). However, there are differences in the amount of IFNγ produced when splenocytes are stimulated with OVA protein, CD8 or CD4 OVA peptides and whether IFNγ is measured in total splenocytes or CD8⁺ or CD4⁺ T cells [48].

The induction of effector CD4⁺ T cells occurs in the same manner and with similar dynamics as is seen with the induction of effector memory CD8⁺ T cells [43]. However, the increased CD4⁻ memory T cells appear to be dominated by helper cells in mice immunized with CPZ-OVA vaults. Our data shows that the addition of the "Z" domain modifies antibody isotypes and supports the increased ratio of anti-OVA IgG1 over IgG2c titers. Adjuvants enhance immunity to immunogens but also steer immunity toward specific immune responses. For instance, alum is a known to promote Th2 responses [49]. The ability of vault vaccines to alter antibody isotypes suggests that modification of the vault toward certain immune responses is possible [50]. Recently, we have modified the vault by the addition of a lytic peptide derived from the adenovirus pIV protein. This modification allows those vaults to rapidly escape phagocytic vesicles [51]. Future studies will examine the in vivo immune responses generated by these vaults.

These results plus our previous studies with chemokines (CCL21) [28] and a chlamydial protein (MOMP) [27], supports the hypothesis that vault nanocapsules can be potent antigen delivery vehicles. Vault nanocapsules act as "smart" adjuvants that are capable of directing immunity toward desired responses with little induction of inflammatory cytokines when delivered via a mucosal route [27]. Further studies comparing immunization routes will be needed to determine the most effective route for the desired immune response. Since vaults are ubiquitous and conserved across eukaryote species, the platform has a major advantage over other delivery systems which have safety concerns associated with attenuated bacteria or viruses. In addition, vault nanocapsules are uniform in size and are able to be produced in abundance. Combining adjuvant and carrier activity, engineered vaults enhance the response with a much lower dose of the antigen and circumvent the protein-purification requirements of traditional subunit vaccines and particulate antigen-delivery modalities. With possibilities of further engineering the surface of vaults to either target specific cells or by allowing the proteins to escape endosomes, vaults provide a uniquely tunable platform with ease of manufacture for the delivery of a wide spectrum of subunit antigens for vaccines against infectious disease or other therapeutic targets.

REFERENCES

1. Reed S G, Bertholet S, Coler R N, Friede M (2009) New horizons in adjuvants for vaccine development. Trends Immunol 30: 23-32.
2. Walker B D, Burton D R (2008) Toward an AIDS vaccine. Science 320: 760-764.
3. Zhou F (2010) Perforin: More than Just a Pore-Forming Protein. Int Rev Immunol 29: 56-76.
4. Fritsche P J, Helbling A, Ballmer-Weber B K (2010) Vaccine hypersensitivity—update and overview. Swiss Med Wkly 140: 238-246.
5. Fulginiti V A, Eller J J, Sieber O F, Joyner J W, Minamitani M, et al. (1969) Respiratory virus immunization. I. A field trial of two inactivated respiratory virus vaccines; an aqueous trivalent parainfluenza virus vaccine and an alum-precipitated respiratory syncytial virus vaccine. Am J Epidemiol 89: 435-448.
6. Flatz L, Hegazy A N, Bergthaler A, Verschoor A, Claus C, et al. (2010) Development of replication-defective lymphocytic choriomeningitis virus vectors for the induction of potent CD8(+) T cell immunity. Nat Med 16: 339-U142.
7. Haglund K, Leiner I, Kerksiek K, Buonocore L, Pamer E, et al. (2002) Robust recall and long-term memory T-cell responses induced by prime-boost regimens with heterologous live viral vectors expressing human immunodeficiency virus type I Gag and Env proteins. J Virol 76: 7506-7517.
8. Brave A, Ljungberg K, Wahren B, Liu M A (2007) Vaccine delivery methods using viral vectors. Mol Pharm 4: 18-32.
9. Hubbell J A, Thomas S N, Swartz M A (2009) Materials engineering for immunomodulation. Nature 462: 449-460.
10. Heath W R, Carbone F R (2001) Cross-presentation in viral immunity and self-tolerance. Nat Rev Immunol 1: 126-134.
11. Langridge W, Denes B, Fodor I (2010) Cholera toxin B subunit modulation of mucosal vaccines for infectious and autoimmune diseases. Curr Opin Investig Drugs 11: 919-928.
12. Harnack U, Johnen H, Pecher G (2010) IL-1 receptor antagonist anakinra enhances tumour growth inhibition in mice receiving peptide vaccination and beta-(1-3),(1-6)-D-glucan. Anticancer Res 30: 3959-3965.
13. Guy B (2007) The perfect mix: recent progress in adjuvant research. Nat Rev Microbiol 5: 505-517.
14. Perrie Y, Mohammed A R, Kirby D J, McNeil S E, Bramwell V W (2008) Vaccine adjuvant systems: Enhancing the efficacy of sub-unit protein antigens. Int J Pharm 364: 272-280.
15. Watts C (1997) Capture and processing of exogenous antigens for presentation on MHC molecules. Ann Rev Immuno 15: 821-850.
16. Regnault A, Lankar D, Lacabanne V, Rodriguez A, Thery C, et al. (1999) Fc gamma receptor-mediated induction of dendritic cell maturation and major histocompatibility complex class I-restricted antigen presentation after immune complex internalization. J Exp Med 189: 371-380.
17. Mitchell D A, Nair S K, Gilboa E (1998) Dendritic cell macrophage precursors capture exogenous antigen for MHC class I presentation by dendritic cells (vol 28, pg 1923, 1998). Eur J Immunol 28: 3891-3891.
18. Ingolotti M, Kawalekar O, Shedlock D J, Muthumani K, Weiner D B (2010) DNA vaccines for targeting bacterial infections. Expert Rev Vaccines 9: 747-763.
19. Ohlschlager P, Spies E, Alvarez G, Quetting M, Groettrup M (2011) The combination of TLR-9 adjuvantation and electroporation-mediated delivery enhances in vivo antitumor responses after vaccination with HPV-16 E7 encoding DNA. Int J Cancer 128: 473-481.
20. McNeela E, Mills K (2001) Manipulating the immune system: humoral versus cell-mediated immunity. Adv Drug Deliv Rev 51: 43-54.

21. Pathak Y, Thassu D, editors (2009) Drug delivery nanoparticles formulations and characterization. New York: Informa healthcare. p. 1-391.
22. Bolhassani A, Safaiyan S, Rafati S (2011) Improvement of different vaccine delivery systems for cancer therapy. Mol Cancer 10:3.
23. Chou L Y, Ming K, Chan W C (2011) Strategies for the intracellular delivery of nanoparticles. Chem Soc Rev 40: 233-245.
24. Izquierdo M A, Scheffer G L, Flens M J, Giaccone G, Broxterman H J, et al. (1996) Broad distribution of the multidrug resistance-related vault lung resistance protein in normal human tissues and tumors. Am J Pathol 148: 877-887.
25. Suprenant K (2002) Vault ribonucleoprotein particles: sarcophagi, gondolas, or safety deposit boxes? Biochemistry 41: 14447-14454.
26. Berger W, Steiner E, Grusch M, Elbling L, Micksche M (2009) Vaults and the major vault protein: Novel roles in signal pathway regulation and immunity. Cellular and Molecular Life Sciences 66: 43-61.
27. Champion C I, Kickhoefer V A, Liu G C, Moniz R J, Freed A S, et al. (2009) A Vault Nanoparticle Vaccine Induces Protective Mucosal Immunity. Plos One 4: e5409.
28. Kar U K, Srivastava M K, Andersson A, Baratelli F, Huang M, et al. (2011) Novel CCL21-Vault Nanocapsule Intratumoral Delivery Inhibits Lung Cancer Growth. Plos One 6: e18758.
29. Carstens M G, Camps M G, Henriksen-Lacey M, Franken K, Ottenhoff T H, et al. (2011) Effect of vesicle size on tissue localization and immunogenicity of liposomal DNA vaccines. Vaccine 29: 4761-4770.
30. Assudani D, Cho H I, DeVito N, Bradley N, Celis E (2008) In vivo Expansion, Persistence, and Function of Peptide Vaccine-Induced CD8 T Cells Occur Independently of CD4 T Cells. Cancer Res 68: 9892-9899.
31. Mikyas Y, Makabi M, Raval-Fernandes S, Harrington L, Kickhoefer V A, et al. (2004) Cryoelectron microscopy imaging of recombinant and tissue derived vaults: localization of the MVP N termini and VPARP. J Mol Biol 344: 91-105.
32. Kickhoefer V A, Han M, Raval-Fernandes S, Poderycki M J, Moniz R J, et al. (2009) Targeting vault nanoparticles to specific cell surface receptors. ACS Nano 3: 27-36.
33. Stephen A G, Raval-Fernandes S, Huynh T, Tones M, Kickhoefer V A, et al. (2001) Assembly of vault-like particles in insect cells expressing only the major vault protein. J Biol Chem 276: 23217-23220.
34. Poderycki M J, Kickhoefer V A, Kaddis C S, Raval-Fernandes S, Johansson E, et al. (2006) The vault exterior shell is a dynamic structure that allows incorporation of vault-associated proteins into its interior. Biochemistry 45: 12184-12193.
35. Burgdorf S, Scholz C, Kautz A, Tampe R, Kurts C (2008) Spatial and mechanistic separation of cross-presentation and endogenous antigen presentation. Nat Immunol 9: 558-566.
36. Ferrari C, Pilli M, Penna A, Bertoletti A, Valli A, et al. (1992) Autopresentation of hepatitis B virus envelope antigens by T cells. J Virol 66: 2536-2540.
37. Tiwari S, Agrawal G P, Vyas S P (2010) Molecular basis of the mucosal immune system: from fundamental concepts to advances in liposome-based vaccines. Nanomedicine (Lond) 5: 1617-1640.
38. Moon J J, Suh H, Bershteyn A, Stephan M T, Liu H, et al. (2011) Interbilayer-crosslinked multilamellar vesicles as synthetic vaccines for potent humoral and cellular immune responses. Nat Mater 10: 243-251.
39. Kim C, Williams M A (2010) Nature and nurture: T-cell receptor-dependent and T-cell receptor-independent differentiation cues in the selection of the memory T-cell pool. Immunology 131: 310-317.
40. Moser M (2001) Regulation of Th1/Th2 development by antigen-presenting cells in vivo. Immunobiology 204: 551-557.
41. Joffre O, Nolte M A, Sporri R, Sousa C R E (2009) Inflammatory signals in dendritic cell activation and the induction of adaptive immunity. Immunol Rev 227: 234-247.
42. Nembrini C, Stano A, Dane K Y, Ballester M, van der Vlies A J, et al. (2011) Nanoparticle conjugation of antigen enhances cytotoxic T-cell responses in pulmonary vaccination. Proc Natl Acad Sci USA 108:E989-97.
43. Ahlers J D, Belyakov I M (2010) Molecular pathways regulating CD4(+) T cell differentiation, anergy and memory with implications for vaccines. Trends Mol Med 16: 478-491.
44. Henriques A M, Madeira C, Fevereiro M, Prazeres D M, Aires-Barros M R, et al. (2009) Effect of cationic liposomes/DNA charge ratio on gene expression and antibody response of a candidate DNA vaccine against Maedi Visna virus. Int J Pharm 377: 92-98.
45. Mohanan D, Shiner B, Henriksen-Lacey M, Jiskoot W, Bouwstra J A, et al. (2010) Administration routes affect the quality of immune responses: A cross-sectional evaluation of particulate antigen-delivery systems. J Control Release 147: 342-349.
46. Zhong Z, Wei X, Qi B, Xiao W, Yang L, et al. (2010) A novel liposomal vaccine improves humoral immunity and prevents tumor pulmonary metastasis in mice. Int J Pharm 399: 156-162.
47. Steiner E, Holzmann K, Pirker C, Elbling L, Micksche M, et al. (2006) The major vault protein is responsive to and interferes with interferon-gamma-mediated STAT1 signals. J Cell Sci 119: 459-469.
48. Andrews C D, Huh M-S, Patton K, Higgins D, Van Nest G, et al. (2012) Encapsulating Immunostimulatory CpG Oligonucleotides in Listeriolysin O-Liposomes Promotes a Th1-Type Response and CTL Activity. Molecular Pharmaceutics April 6. [Epub ahead of print]
49. Marrack P, McKee A S, Munks M W (2009) Towards an understanding of the adjuvant action of aluminium. Nat Rev Immunol 9: 287-293.
50. Huber V C, McKeon R M, Brackin M N, Miller L A, Keating R, et al. (2006) Distinct contributions of vaccine-induced immunoglobulin G1 (IgG1) and IgG2a antibodies to protective immunity against influenza. Clin Vaccine Immunol 13: 981-990.
51. Han M, Kickhoefer V A, Nemerow G R, Rome L H (2011) Targeted vault nanoparticles engineered with an endosomolytic peptide deliver biomolecules to the cytoplasm. ACS Nano 5: 6128-6137.
52. Kickhoefer V A, Siva A C, Kedersha N L, Inman E M, Ruland C, et al. (1999) The 193-Kd Vault Protein, Vparp, Is a Novel Poly(Adp-Ribose) Polymerase. J Cell Biol 146: 917-928.
53. Kickhoefer V A, Garcia Y, Mikyas Y, Johansson E, Zhou J C, et al. (2005) Engineering of vault nanocapsules with enzymatic and fluorescent properties. Proc Natl Acad Sci USA 102: 4348-4352.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 1

Sequences

SEQ ID NO: 1 INT DNA sequence
TGC ACA CAA CAC TGG CAG GAT GCT GTG CCT TGG ACA GAA CTC CTC AGT
CTA CAG ACA GAG GAT GGC TTC TGG AAA CTT ACA CCA GAA CTG GGA CTT
ATA TTA AAT CTT AAT ACA AAT GGT TTG CAC AGC TTT CTT AAA CAA AAA
GGC ATT CAA TCT CTA GGT GTA AAA GGA AGA GAA TGT CTC CTG GAC CTA
ATT GCC ACA ATG CTG GTA CTA CAG TTT ATT CGC ACC AGG TTG GAA AAA
GAG GGA ATA GTG TTC AAA TCA CTG ATG AAA ATG GAT GAC CCT TCT ATT
TCC AGG AAT ATT CCC TGG GCT TTT GAG GCA ATA APG CAA GCA AGT GAA
TGG GTA AGA AGA ACT GAA GGA CAG TAC CCA TCT ATC TGC CCA CGG CTT
GAA CTG GGG APC GAC TGG GAC TCT GCC ACC APG CAG TTG CTG GGA CTC
CAG CCC ATA AGC ACT GTG TCC CCT CTT CAT AGA GTC CTC CAT TAC AGT
CAA GGC TAA SEQ ID NO: 2 INT protein sequence (residues 1563-1724 of the human
VPARP protein sequence)
CTQHWQDAVPWTELLSLQTEDGFWKLTPELGLILNLNTNGLHSFLKQKGIQSLGVKGRECLLDLIA
TMLVLQFIRTRLEKEGIVEKSLMKMDDPSISRNIPWAFEAIKQASEWVRRTEGQYPSICPRLELGN
DWDSATKQLLGLQPISTVSPLHRVLHYSQG SEQ ID NO: 3 VPARP protein sequence (Genbank #AAD47250)
Met Val Met Gly Ile Phe Ala Asn Cys Ile Phe Cys Leu Lys Val Lys Tyr Leu
Pro Gln Gln Gln Lys Lys Lys Leu Gln Thr Asp Ile Lys Glu Asn Gly Gly Lys
Phe Ser Phe Ser Leu Asn Pro Gln Cys Thr His Ile Leu Asp Asn Ala Asp
Val Leu Ser Gln Tyr Gln Leu Asn Ser Ile Gln Lys Asn His Val His Ile Ala
Asn Pro Asp Phe Ile Trp Lys Ser Ile Arg Glu Lys Arg Leu Leu Asp Val Lys
Asn Tyr Asp Pro Tyr Lys Pro Leu Asp Ile Thr Pro Pro Asp Gln Lys Ala
Ser Ser Ser Glu Val Lys Thr Gly Leu Cys Pro Asp Ser Ala Thr Glu Glu
Glu Asp Thr Val Glu Leu Thr Glu Phe Gly Met Gln Asn Val Glu Ile Pro His
Leu Pro Gln Asp Phe Glu Val Ala Lys Tyr Asn Thr Leu Glu Lys Val Gly Met
Glu Gly Gly Gln Glu Ala Val Val Val Glu Leu Gln Cys Ser Arg Asp Ser Arg
Asp Cys Pro Phe Leu Ile Ser Ser His Phe Leu Asn Asp Asp Gly Met Glu Thr
Arg Arg Gln Phe Ala Ile Lys Lys Thr Ser Glu Asp Ala Ser Glu Val Tyr Phe Glu
Asn Tyr Ile Glu Glu Leu Lys Lys Gln Gly Phe Leu Leu Arg Glu His Phe Thr
Pro Glu Ala Thr Gln Leu Ala Ser Glu Gln Leu Gln Ala Leu Leu Glu Glu
Val Met Asn Ser Ser Thr Leu Ser Gln Glu Val Ser Asp Leu Val Glu Met Ile
Trp Ala Glu Ala Leu Gly His Leu His Met Met Leu Leu Lys Pro Val Asn Arg
Ile Ser Leu Asn Asp Val Ser Lys Ala Glu Gly Ile Leu Leu Leu Lys Ala
Ala Leu Lys Asn Gly Glu Thr Ala Glu Gln Leu Gln Lys Met Met Thr Glu Phe
Tyr Arg Leu Ile Pro His Lys Gly Thr Met Pro Lys Glu Val Asn Leu Gly Leu
Leu Ala Lys Lys Ala Asp Leu Cys Gln Leu Ile Arg Asp Met Val Asn Val Cys
Glu Thr Asn Leu Ser Lys Pro Asn Pro Pro Ser Leu Ala Lys Tyr Arg Ala Leu
Arg Cys Lys Ile Glu His Val Glu Gln Asn Thr Glu Glu Phe Leu Arg Val Arg
Lys Glu Val Leu Gln Asn His His Ser Lys Ser Pro Val Asp Val Leu Gln Ile
Phe Arg Val Gly Arg Val Asn Glu Thr Thr Glu Phe Leu Ser Lys Leu Gly Asn
Val Arg Pro Leu Leu His Gly Ser Pro Val Gln Asn Ile Val Gly Ile Leu Cys
Arg Gly Leu Leu Leu Pro Lys Val Val Glu Asp Arg Gly Val Gln Arg Thr Asp
Val Gly Asn Leu Gly Ser Gly Ile Tyr Phe Ser Asp Ser Leu Ser Thr Ser Ile
Lys Tyr Ser His Pro Gly Glu Thr Asp Gly Thr Arg Leu Leu Leu Ile Cys Asp
Val Ala Leu Gly Lys Cys Met Asp Leu His Glu Lys Asp Phe Pro Leu Thr Glu
Ala Pro Pro Gly Tyr Asp Ser Val His Gly Val Ser Gln Thr Ala Ser Val Thr
Thr Asp Phe Glu Asp Asp Glu Phe Val Val Tyr Lys Thr Asn Gln Val Lys Met
Lys Tyr Ile Ile Lys Phe Ser Met Pro Gly Asp Ile Lys Asp Phe His Pro
Ser Asp His Thr Glu Leu Glu Glu Tyr Arg Pro Glu Phe Ser Asn Phe Ser Lys
Val Glu Asp Tyr Gln Leu Pro Asp Ala Lys Thr Ser Ser Ser Thr Lys Ala Gly
Leu Gln Asp Ala Ser Gly Asn Leu Val Pro Leu Glu Asp Val His Ile Lys Gly
Arg Ile Ile Asp Thr Val Ala Gln Val Ile Val Phe Gln Thr Tyr Thr Asn Lys
Ser His Val Pro Ile Glu Ala Lys Tyr Ile Phe Pro Leu Asp Asp Lys Ala Ala
Val Cys Gly Phe Glu Ala Phe Ile Asn Gly Lys His Ile Val Gly Glu Ile Lys
Glu Lys Glu Glu Ala Gln Gln Glu Tyr Leu Glu Ala Val Thr Gln Gly His Gly
Ala Tyr Leu Met Ser Gln Asp Ala Pro Asp Val Phe Thr Val Ser Val Gly Asn
Leu Pro Pro Lys Ala Lys Val Leu Ile Lys Ile Thr Tyr Ile Thr Glu Leu Ser
Ile Leu Gly Thr Val Gly Val Phe Phe Met Pro Ala Thr Val Ala Pro Trp Gln
Gln Asp Lys Ala Leu Asn Glu Asn Leu Gln Asp Thr Val Glu Lys Ile Cys Ile
Lys Glu Ile Gly Thr Lys Gln Ser Phe Ser Leu Thr Met Ser Ile Glu Met Pro
Tyr Val Ile Glu Phe Ile Phe Ser Asp Thr His Leu Leu Lys Gln Lys Arg Thr
Asp Cys Lys Ala Val Ile Ser Thr Met Glu Gly Ser Ser Leu Asp Ser Ser Gly
Phe Ser Leu His Ile Gly Leu Ser Ala Ala Tyr Leu Pro Arg Met Trp Val Glu
Lys His Pro Glu Lys Glu Ser Glu Ala Cys Met Leu Val Phe Gln Pro Asp Leu
Asp Val Asp Leu Pro Asp Leu Ala Ser Glu Ser Gln Val Ile Ile Cys Leu Asp
Cys Ser Ser Ser Met Glu Gly Val Thr Phe Leu Gln Ala Lys Gln Ile Thr Leu
His Ala Leu Ser Leu Val Gly Glu Lys Gln Lys Val Asn Ile Ile Gln Phe Gly
Thr Gly Tyr Lys Glu Leu Phe Ser Tyr Pro Lys His Ile Thr Ser Asn Thr Thr
Ala Glu Gln Phe Ile Met Ser Ala Thr Pro Thr Met Gly Asn Thr Asp Phe Trp
Lys Thr Leu Arg Tyr Leu Ser Leu Leu Tyr Pro Ala Arg Gly Ser Arg Asn Ile
Leu Leu Val Ser Asp Gly His Leu Gln Asp Glu Ser Leu Thr Leu Gln Leu Val
Lys Arg Ser Arg Pro His Thr Arg Leu Phe Ala Cys Gly Ile Gly Ser Thr Ala
Asn Arg His Val Leu Arg Ile Leu Ser Gln Cys Gly Ala Gly Val Phe Glu Tyr
Phe Asn Ala Lys Ser Lys His Ser Trp Arg Lys Gln Ile Glu Asp Gln Met Thr TABLE 1 -continued Sequences Arg Leu Cys Ser Pro Ser Cys His Ser Val Ser Val Lys Trp Gln Gln Leu Asn
Pro Asp Ala Pro Glu Ala Leu Gln Ala Pro Ala Gln Val Pro Ser Leu Phe Arg
Asn Asp Arg Leu Leu Val Tyr Gly Phe Ile Pro His Cys Thr Gln Ala Thr Leu
Cys Ala Leu Ile Gln Glu Lys Glu Phe Cys Thr Met Val Ser Thr Thr Glu Leu
Gln Lys Thr Thr Gly Thr Met Ile His Lys Leu Ala Ala Arg Ala Leu Ile Arg
Asp Tyr Glu Asp Gly Ile Lue His Glu Asn Glu Thr Ser His Glu Met Lys Lys
Gln Thr Leu Lys Ser Ile Ile Lys Leu Ser Lys Glu Asn Ser Leu Ile Thr
Gln Phe Thr Ser Phe Val Ala Val Glu Lys Arg Asp Glu Asn Glu Ser Pro Phe
Pro Asp Ile Pro Lys Val Ser Glu Leu Ile Ala Lys Glu Asp Val Asp Phe Leu
Pro Tyr Met Ser Trp Gln Gly Glu Pro Gln Glu Ala Val Arg Asn Gln Ser Leu
Leu Ala Ser Glu Trp Pro Glu Leu Arg Ser Lys Arg Lys Lys His Arg Lys
Ile Pro Phe Ser Lys Arg Lys Met Glu Leu Ser Gln Pro Glu Val Ser Glu Asp
Phe Glu Glu Asp Gly Leu Gly Val Leu Pro Ala Phe Thr Ser Asn Leu Glu Arg
Gly Gly Val Glu Lys Leu Leu Asp Leu Ser Trp Thr Glu Ser Cys Lys Pro Thr
Ala Thr Glu Pro Leu Phe Lys Lys Val Ser Pro Thr Trp Thr Ser Thr Ser Ser
Phe Phe Pro Ile Leu Ala Pro Ala Val Gly Ser Tyr Leu Thr Pro Thr Thr Arg
Ala His Ser Pro Ala Ser Leu Ser Phe Ala Ser Tyr Arg Gln Val Ala Ser Phe
Gly Ser Ala Ala Pro Pro Arg Gln Phe Asp Ala Ser Gln Phe Ser Gln Gly Pro
Val Pro Gly Thr Cys Ala Asp Trp Ile Pro Gln Ser Ala Ser Cys Pro Thr Gly
Pro Pro Gln Asn Pro Pro Ser Ala Pro Tyr Cys Gly Ile Val Phe Ser Gly Ser
Ser Leu Ser Ser Ala Gln Ser Ala Pro Leu Gln His Pro Gly Gly Phe Thr Thr
Arg Pro Ser Ala Gly Thr Phe Pro Glu Leu Asp Ser Pro Gln Leu His Phe Ser
Leu Pro Thr Asp Pro Asp Pro Ile Arg Gly Phe Gly Ser Tyr His Pro Ser Ala
Tyr Ser Pro Phe His Phe Gln Pro Ser Ala Ala Ser Leu Thr Ala Asn Leu Arg
Leu Pro Met Ala Ser Ala Leu Pro Glu Ala Leu Cys Ser Gln Ser Arg Thr Thr
Pro Val Asp Leu Cys Leu Leu Glu Glu Ser Val Gly Ser Leu Glu Gly Ser Arg
Cys Pro Val Phe Ala Phe Gln Ser Ser Asp Thr Glu Ser Asp Glu Leu Ser Glu
Val Leu Gln Asp Ser Cys Phe Leu Gln Ile Lys Cys Asp Thr Lys Asp Asp Ser
Ile Pro Cys Phe Leu Glu Leu Lys Glu Glu Asp Glu Ile Val Cys Thr Gln His
Trp Gln Asp Ala Val Pro Trp Thr Glu Leu Leu Ser Leu Gln Thr Glu Asp Gly
Phe Trp Lys Leu Thr Pro Glu Leu Gly Leu Ile Leu Asn Leu Asn Thr Asn Gly
Leu His Ser Phe Leu Lys Gln Lys Gly Ile Gln Ser Leu Gly Val Lys Gly Arg
Glu Cys Leu Leu Asp Leu Ile Ala Thr Met Leu Val Leu Gln Phe Ile Arg Thr
Arg Leu Glu Lys Glu Gly Ile Val Phe Lys Ser Leu Met Lys Met Asp Asp Pro
Ser Ile Ser Arg Asn Ile Pro Trp Ala Phe Glu Ala Ile Lys Gln Ala Ser Glu
Trp Val Arg Arg Thr Glu Gly Gln Tyr Pro Ser Leu Cys Pro Arg Leu Glu Leu
Gly Asn Asp Trp Asp Ser Ala Thr Lys Gln Leu Leu Gly Leu Gln Pro Ile Ser
Thr Val Ser Pro Leu His Arg Val Leu His Tyr Ser Gln Gly SEQ ID NO: 5 VPARP cDNA, Genbank #AF158255
atggtgatgg gaatctttgc aaattgtatc ttctgtttga aagtgaagta cttacctcag
cagcagaaga aaaagctaca aactgacatt aaggaaaatg gcggaaagtt ttccttttcg
ttaaatcctc agtgcacaca tataatctta gataatgctg atgttctgag tcagtaccaa
ctgaattcta tccaaaagaa ccacgttcat attgcaaacc cagattttat atggaaatct
atcagagaaa agagactctt ggatgtaaag aattatgatc cttataagcc cctggacatc
acaccacctc ctgatcagaa ggcgagcagt tctgaagtga aaacagaagg tctatgcccg
gacagtgcca cagaggagga agacactgtg gaactcactg agtttggtat gcagaatgtt
gaaattcctc atcttcctca agattttgaa gttgcaaaat ataacacctt ggagaaagtg
ggaatggagg gaggccagga agctgtggtg gtggagcttc agtgttcgcg ggactccagg
gactgtcctt tcctgatatc ctcacacttc ctcctggatg atggcatgga gactagaaga
cagtttgcta taaagaaaac ctctgaagat gcaagtgaat actttgaaaa ttacattgaa
gaactgaaga aacaaggatt tctactaaga gaacatttca cacctgaagc aacccaatta
gcatctgaac aattgcaagc attgcttttg gaggaagtca tgaattcaag cactctgagc
caagaggtga gcgatttagt agagatgatt tgggcagagg ccctgggcca cctggaacac
atgcttctca agccagtgaa caggattagc ctcaacgatg tgagcaaggc agaggggatt
ctccttctag taaaggcagc actgaaaaat ggagaaacag cagagcaatt gcaaaagatg
atgacagagt tttacagact gatacctcac aaaggcacaa tgcccaaaga agtgaacctg
ggactattgg ctaagaaagc agacctctgc cagctaataa agacatggt taatgtctgt
gaaactaatt tgtccaaacc caacccacca tccctggcca aataccgagc tttgaggtgc
aaaattgagc atgttgaaca gaatactgaa gaatttctca gggttagaaa agaggttttg
cagaatcatc acagtaagag cccagtggat gtcttgcaga tatttagagt tggcagagtg
aatgaaacca cagagttttt gagcaaactt ggtaatgtga ggcccttgtt gcatggttct
cctgtacaaa acatcgtggg aatcttgtgt cgagggttgc ttttacccaa agtagtggaa
gatcgtggtg tgcaaagaac agacgtcgga aaccttggaa gtgggattta tttcagtgat
tcgctcagta caagtatcaa gtactcacac ccgggagaga catggcac cagactcctg
ctcatttgtg acgtagccct cggaaagtgt atggacttac atgagaagga cttcccctta
actgaagcac caccaggcta cgacagtgtg catggagttt cacaaacagc ctctgtcacc
acagacttg aggatgatga atttgttgtc tataaaacca atcaggttaa atgaaatat
attattaaat tttccatgcc tggagatcag ataaaggact ttcatcctag tgatcatact
gaattagagg aatacagacc tgagtttttca aattttttcaa aggttgaaga ttaccagtta
ccagatgcca aaacttccag cagcaccaag gccggcctcc aggatgcctc tgggaacttg
gttcctctgg aggatgtcca catcaaaggg agaatcatag acactgtagc ccaggtcatt
gttttttcaga catacacaaa taaaagtcac gtgcccattg aggcaaaata tcttttcct
ttggatgaca aggccgctgt gtgtggcttc gaagccttca tcaatgggaa gcacatagtt
ggagagatta agagaagga agaagcccag caagagtacc tagaagccgt gacccagggc
catgcgcctt acctgatgag tcaggatgct ccggacgttt ttactgtaag tgttggaaac
ttaccccta aggctaaggt tcttataaaa attacctaca tcacagaact cagcatcctg
ggcactgttg gtgtcttttt catgcccgcc accgtagcac cctggcaaca ggacaaggct TABLE 1 -continued Sequences

```
ttgaatgaaa accttcagga tacagtagag aagatttgta taaaagaaat aggaacaaag
caaagcttct ctttgactat gtctattgag atgccgtatg tgattgaatt cattttcagt
gatacacatg aactgaaaca aaagcgcaca gactgcaaag ctgtcattag caccatgaa
ggcagctcct tagacagcag tggatttttct ctccacatcg gtttgtctgc tgcctatctc
ccaagaatgt gggttgaaaa acatccagaa aaagaaagcg aggcttgcat gcttgtcttt
caacccgatc tcgatgtcga cctccctgac ctagccagtg agagcgaagt gattatttgt
cttgactgct ccagttccat ggagggtgtg acattcttgc aagccaagca aatcaccttg
catgcgctgt ccttggtggg tgagaagcag aaagtaaata ttatccagtt cggcacaggt
tacaaggagc tattttcgta tcctaagcat atcacaagca ataccacggc agcagagttc
atcatgtctg ccacacctac catggggaac acagacttct ggaaaacact ccgatatctt
agcttattgt accctgctcg agggtcacgg aacatcctcc tggtgtctga tgggcacctc
caggatgaga gcctgacatt acagctcgtg aagaggagcc gcccgcacac caggttattc
gcctgcggta tcggttctac agcaaatcgt cacgtcttaa ggattttgtc ccagtgtggt
gccggagtat ttgaatattt taatgcaaaa tccaagcata gttggagaaa acagatagaa
gaccaaatga ccaggctatg ttctccgagt tgccactctg tctccgtcaa atggcagcaa
ctcaatccag atgcgcccga ggccctgcag gccccagccc aggtgccatc cttgtttcgc
aatgatcgac tccttgtcta tggattcatt cctcactgca cacaagcaac tctgtgtgca
ctaattcaag agaaagaatt ttgtacaatg gtgtcgacta ctgagcttca gaagacaact
ggaactatga tccacaagct ggcagcccga gctctaatca gagattatga agatggcatt
cttcacgaaa atgaaaccag tcatgagatg aaaaaacaaa ccttgaaatc tctgattatt
aaactcagta agaaaaactc tctcataaca caatttacaa gctttgtggc agttgagaaa
agggatgaga atgagtcgcc ttttcctgat attccaaaag tttctgaact tattgccaaa
gaagatgtag acttcctgcc ctacatgagc tggcagggg agccccaaga agccgtcagg
aaccagtctc ttttagcatc ctctgagtgg ccagaattac gtttatccaa acgaaaacat
aggaaaattc cattttccaa aagaaaaatg gaattatctc agccagaagt ttctgaagat
tttgaagagg atggcttagg tgtactacca gctttcacat caaatttgga acgtggaggt
gtggaaaagc tattggattt aagttggaca gagtcatgta aaccaacagc aactgaacca
ctatttaaga aagtcagtcc atgggaaaca tctacttcta gcttttttcc tatttttggct
ccggccgttg gttcctatct taccccgact acccgcgctc acagtcctgc ttccttgtct
tttgcctcat atcgtcaggt agctagtttc ggttcagctg ctcctcccag acagtttgat
gcatctcaat tcagccaagg ccctgtgcct ggcacttgtg ctgactggat cccacagtcg
gcgtcttgtc ccacaggacc tccccagaac ccaccttctg caccctattg tggcattgtt
ttttcaggga gctcattaag ctctgcacag tctgctccac tgcaacatcc tggaggcttt
actaccaggc cttctgctgg caccttccct gagctggatt ctccccagct tcatttctct
cttcctacag accctgatcc catcagaggt tttgggtctt atcatccctc tgcttactct
cctttcatt ttcaaccttc cgcagcctct tgactgcca accttaggct gccaatggcc
tctgctttac ctgaggctct ttgcagtcag tcccggacta ccccagtaga tctctgtctt
ctagaagaat cagtaggcag tctcgaagga agtcgatgtc ctgtctttgc ttttcaaagt
tctgacacag aaagtgatga gctatcagaa gtacttcaag acagctgctt tttacaaata
aagtgtgata caaaagatga cagtatcccg tgctttctgt aattaaaaga agaggatgaa
atagtgtgca cacaacactg gcaggatgct gtgccttgga cagaactcct cagtctacag
acagaggatg gcttctggaa acttacacca gaactgggac ttatattaaa tcttaataca
aatggtttgc acagctttct taaacaaaaa ggcattcaat ctctaggtgt aaaaggaaga
gaatgtctcc tggacctaat tgccacaatg ctggtactac agtttattcg caccaggttg
gaaaaagagg gaatagtgtt caaatcactg atgaaaatgg atgacccttc tatttccagg
aatattccct gggcttttga ggcaataaag caagcaagtg aatgggtaag aagaactgaa
ggacagtacc catctatctg cccacggctt gaactgggga acgactggga ctctgccacc
aagcagttgc tgggactcca gcccataagc actgtgtccc ctcttcatag agtcctccat
tacagtcaag gctaa
```

SEQ ID NO: 6 MVP (Genbank #CAA56256)
Met Ala Thr Glu Glu Phe Ile Ile Arg Ile Pro Pro Tyr His Tyr Ile His Val
Leu Asp Gln Asn Ser Asn Val Ser Arg Val Glu Val Gly Pro Lys Thr Tyr Ile
Arg Gln Asp Asn Glu Arg Val Leu Phe Ala Pro Met Arg Met Val Thr Val Pro
Pro Arg His Tyr Cys Thr Val Ala Asn Pro Val Ser Arg Asp Ala Gln Gly Leu
Val Leu Phe Asp Val Thr Gly Gln Val Arg Leu Arg His Ala Asp Leu Glu Ile
Arg Leu Ala Gln Asp Pro Phe Pro Leu Tyr Pro Gly Glu Val Leu Glu Lys Asp
Ile Thr Pro Leu Gln Val Val Leu Pro Asn Thr Ala Leu His Leu Lys Ala Leu
Leu Asp Phe Glu Asp Lys Asp Gly Asp Lys Val Val Ala Gly Asp Glu Trp Leu
Phe Glu Gly Pro Gly Thr Tyr Ile Pro Arg Lys Glu Val Glu Val Val Glu Ile
Ile Glu Ala Thr Ile Ile Arg Gln Asn Gln Ala Leu Arg Leu Arg Ala Arg Lys
Glu Cys Trp Asp Arg Asp Gly Lys Glu Arg Val Thr Gly Glu Glu Trp Leu Val
Thr Thr Val Gly Ala Tyr Leu Pro Ala Val Phe Glu Glu Val Leu Asp Leu Val
Asp Ala Val Ile Leu Thr Glu Lys Thr Ala Leu His Leu Arg Ala Arg Arg Asn
Phe Arg Asp Phe Arg Gly Val Ser Arg Arg Thr Gly Glu Glu Trp Leu Val Thr
Val Gln Asp Thr Glu Ala His Val Pro Asp Val His Glu Glu Val Leu Gly Val
Val Pro Ile Thr Thr Leu Gly Pro His Asn Tyr Cys Val Ile Leu Asp Pro Val
Gly Pro Asp Gly Lys Asn Gln Leu Gly Gln Lys Arg Val Val Lys Gly Glu Lys
Ser Phe Phe Leu Gln Pro Gly Glu Gln Leu Glu Gln Gly Ile Gln Asp Val Tyr
Val Leu Ser Glu Gln Gln Gly Leu Leu Leu Arg Ala Leu Gln Pro Leu Glu Glu
Gly Glu Asp Glu Glu Lys Val Ser His Gln Ala Gly Asp His Trp Leu Ile Arg
Gly Pro Leu Glu Tyr Val Pro Ser Ala Lys Val Glu Val Val Glu Glu Arg Gln
Ala Ile Pro Leu Asp Glu Asn Glu Gly Ile Tyr Val Gln Asp Val Lys Thr Gly
Lys Val Arg Ala Val Ile Gly Ser Thr Tyr Met Leu Thr Gln Asp Glu Val Leu
Trp Glu Lys Glu Leu Pro Pro Gly Val Glu Glu Leu Leu Asn Lys Gly Gln Asp
Pro Leu Ala Asp Arg Gly Glu Lys Asp Thr Ala Lys Ser Leu Gln Pro Leu Ala
Pro Arg Asn Lys Thr Arg Val Val Ser Tyr Arg Val Pro His Asn Ala Ala Val
Gln Val Tyr Asp Tyr Arg Glu Lys Arg Ala Arg Val Val Phe Gly Pro Glu Leu TABLE 1 -continued Sequences Val Ser Leu Gly Pro Glu Glu Gln Phe Thr Val Leu Ser Leu Ser Ala Gly Arg
Pro Lys Arg Pro His Ala Arg Arg Ala Leu Cys Leu Leu Gly Pro Asp Phe
Phe Thr Asp Val Ile Thr Ile Glu Thr Ala Asp His Ala Arg Leu Gln Leu Gln
Leu Ala Tyr Asn Trp His Phe Glu Val Asn Asp Arg Lys Asp Pro Gln Glu Thr
Ala Lys Leu Phe Ser Val Pro Asp Phe Val Gly Asp Ala Cys Lys Ala Ile Ala
Ser Arg Val Arg Gly Ala Val Ala Ser Val Thr Phe Asp Phe His Lys Asn
Ser Ala Arg Ile Leu Arg Thr Ala Val Phe Gly Phe Glu Thr Ser Glu Ala Lys
Gly Pro Asp Gly Met Ala Leu Pro Arg Pro Arg Asp Gln Ala Val Phe Pro Gln
Asn Gly Leu Val Val Ser Ser Val Asp Val Gln Ser Val Glu Pro Val Asp Gln
Arg Thr Arg Asp Ala Leu Gln Arg Ser Val Gln Leu Ala Ile Glu Ile Thr Thr
Asn Ser Gln Glu Ala Ala Ala Lys His Glu Ala Gln Arg Leu Glu Gln Glu Ala
Arg Gly Arg Leu Glu Arg Gln Lys Ile Leu Asp Gln Ser Glu Ala Glu Lys Ala
Arg Lys Glu Leu Leu Glu Leu Glu Ala Leu Ser Met Ala Val Glu Ser Thr Gly
Thr Ala Lys Ala Glu Ala Glu Ser Arg Ala Glu Ala Ala Arg Ile Glu Gly Glu
Gly Ser Val Leu Gln Ala Lys Leu Lys Ala Gln Ala Leu Ala Ile Glu Thr Glu
Ala Glu Leu Gln Arg Val Gln Lys Val Arg Glu Leu Glu Leu Val Tyr Ala Arg
Ala Gln Leu Glu Leu Glu Val Ser Lys Ala Gln Leu Ala Glu Val Glu Val
Lys Lys Phe Lys Gln Met Thr Glu Ala Ile Gly Pro Ser Thr Ile Arg Asp Leu
Ala Val Ala Gly Pro Glu Met Gln Val Lys Leu Gln Ser Leu Gly Leu Lys
Ser Thr Leu Ile Thr Asp Gly Ser Thr Pro Ile Asn Leu Phe Asn Thr Ala Phe
Gly Leu Leu Gly Met Gly Pro Glu Gly Gln Pro Leu Gly Arg Arg Val Ala Ser
Gly Pro Ser Pro Gly Glu Gly Ile Ser Pro Gln Ser Ala Gln Ala Pro Gln Ala
Pro Gly Asp Asn His Val Val Pro Val Leu Arg SEQ ID NO: 7 MVP cDNA, Genbank #X79882
atggcaactg aagagttcat catccgcatc cccccatacc actatatcca tgtgctggac
cagaacagca acgtgtcccg tgtggaggtc gggccaaaga cctacatccg gcaggacaat
gagagggtac tgtttgcccc catgcgcatg gtgaccgtcc ccccacgtca ctactgcaca
gtggccaacc ctgtgtctcg ggatgcccag ggcttggtgc tgtttgatgt cacagggcaa
gttcggcttc gccacgctga cctcgagatc cggctggccc aggacccctt ccccctgtac
ccaggggagg tgctggaaaa ggacatcaca ccctgcagg tggttctgcc caacactgcc
ctccatctaa aggcgctgct tgattttgag gataaagatg gagacaaggt ggtggcagga
gatgagtggc ttttcgaggg acctggcacg tacatccccc ggaaggaagt ggaggtcgtg
gagatcattc aggccaccat catcaggcag aaccaggctc tgcggctcag ggcccgcaag
gagtgctggg accgggacgg caaggagagg gtgacagggg aagaatggct ggtcaccaca
gtaggggcgt acctcccagc ggtgtttgag gaggttcctg atttggtgga cgccgtcatc
cttacggaaa agacagccct gcacctccgg gctcggcgga acttccggga cttcaggtca
gtgtcccgcc gcactgggga ggagtggctg gtaacagtgc aggacacaga ggcccacgtg
ccagatgtcc acgaggaggt gctggggtt gtgcccatca ccaccctggg ccccacaac
tactgcgtga ttctcgaccc tgtcggaccg gatggcaaga atcagctgga gcagaagcgc
gtggtcaagg gagagaagtc tttttcctc cagccaggag agcagctgga acaaggcatc
caggatgtgt atgtgctgtc ggagcagcag gggctgctgc tgagggccct gcagcccctg
gaggaggggg aggatgagga gaaggtctca caccaggctg ggaccactg gctcatccgc
ggaccctgg agtatgtgcc atctgccaaa gtggaggtgg tggaggagcg ccaggccatc
cctctagacg agaacgaggg catctatgtg caggatgtca agaccggaaa ggtgcgcgct
gtgattggaa gcacctacat gctgacccag gacgaagtcc tgtgggagaa agagctgcct
cccgggggtgt aggagctgct gaacaaggg gcaggaccctc tggcagacag gggtgagaag
gacacagcta agagcctcca gcccttggcc cccggaaca agacccgtgt ggtcagctac
cgcgtgcccc acaacgctgc ggtgcaggtg tacgactacc gagagaagcg agcccgcgtg
gtcttcgggc ctgagctggt gtcgctgggc cctgaggagc agttcacagt gttgtccctc
tcagctgggg ggcccaagcg tcccatgcc cgccgtgcgc tctgcctgct gctgggggcct
gacttcttca cagacgtcat caccatcgaa acggcggatc atgccaggct gcaactgcag
ctggcctaca actggcactt tgaggtgaat gaccggaagg acccccaaga gacggccaag
ctcttttcag tgccagactt tgtaggtgat gcctgcaaag ccatcgcatc ccgggtgcgg
ggggccgtgg cctctgtcac tttcgatgac ttccataaga ctcagcccg catcattcgc
actgctgtct ttggctttga gacctcgaa gcgaagggcc ccgatggcat ggcccctgcc
aggcccgggg accaggctgt cttccccaa aacgggctgg tggtcagcag tgtggacgtg
cagtcagtgg agcctgtgga tcagaggacc cggacgcccc tgcaacgcag cgtccagctg
gccatcgaga tcaccaccaa ctcccaggaa gcggcggcca agcatgaggc tcagagactg
gagcaggaag cccgcggccg gcttgagcgg cagaagatcc tggaccagtc agaagccgag
aaagctcgca aggaactttt ggagctggag gctctgagca gtccgtgga gagcaccggg
actgccaagg cggaggccga gtccgtgcg gaggcagccc ggattgaggg agaagggtcc
gtgctgcagg ccaagctaaa agcacaggcc ttggccattg aaacggaggc tgagctccag
agggtccaga aggtccgaga gctggaactg gtctatgccc gggcccagct ggagctggag
gtgagcaagg ctcagcagct ggctgaggtg gaggtgaaga agttcaagca gatgacagag
gccataggcc ccagcaccat cagggacctt gctgtggctg gcctgagat gcaggtaaaa
ctgctccagt ccctgggcct gaaatcaacc ctcatcaccg atggctccac tcccatcaac
ctcttcaaca cagcctttgg gctgctgggg atggggcccg agggtcagcc cctgggcaga
agggtggcca gtgggcccag ccctggggag gggatatccc cccagtctgc tcaggccct
caagctcctg gagacaacca cgtggtgcct gtactgcgct aa SEQ ID NO: 8 CP Peptide
Met Ala Gly Cys Gly Cys Pro Cys Gly Cys Gly Ala SEQ ID NO: 9 CP-MVP
Met Ala Gly Cys Gly Cys Pro Cys Gly Cys Gly Ala Met Ala Thr Glu Glu Phe
Ile Ile Arg Ile Pro Pro Tyr His Tyr Ile His Val Leu Asp Gln Asn Ser Asn
Val Ser Arg Val Glu Val Gly Pro Lys Thr Tyr Ile Arg Gln Asp Asn Glu Arg TABLE 1 -continued Sequences Val Leu Phe Ala Pro Met Arg Met Val Thr Val Pro Arg His Tyr Cys Thr
Val Asn Pro Val Ser Arg Asp Ala Gln Gly Leu Val Leu Phe Asp Val Thr
Gly Gln Val Arg Leu Arg His Ala Asp Leu Glu Ile Arg Leu Ala Gln Asp
Phe Pro Leu Tyr Pro Gly Glu Val Leu Glu Lys Asp Ile Thr Pro Leu Gln Val
Val Leu Pro Asn Thr Ala Leu His Leu Lys Ala Leu Leu Asp Phe Glu Asp Lys
Asp Gly Asp Lys Val Val Ala Gly Asp Glu Trp Leu Phe Glu Gly Pro Gly Thr
Tyr Ile Pro Arg Lys Glu Val Glu Val Val Glu Ile Ile Gln Ala Thr Ile Thr
Arg Gln Asn Gln Ala Leu Arg Leu Arg Ala Arg Lys Glu Cys Trp Asp Arg Asp
Gly Lys Glu Arg Val Thr Gly Glu Glu Trp Leu Val Thr Val Gly Ala Tyr
Leu Pro Ala Val Phe Glu Glu Val Leu Asp Leu Val Asp Ala Val Ile Leu Thr
Glu Lys Thr Ala Leu His Leu Arg Ala Arg Arg Asn Phe Arg Asp Phe Arg Gly
Val Ser Arg Arg Thr Gly Glu Glu Trp Leu Val Thr Val Gln Asp Thr Glu Ala
His Val Pro Asp Val His Glu Glu Val Leu Gly Val Val Pro Ile Thr Thr Leu
Gly Pro His Asn Tyr Cys Val Ile Leu Asp Pro Val Gly Pro Asp Gly Lys Asn
Gln Leu Gly Gln Lys Arg Val Val Lys Gly Val Lys Ser Phe Phe Leu Gln Pro
Gly Glu Gln Leu Glu Gln Gly Ile Gln Asp Val Tyr Val Leu Ser Glu Gln Gln
Gly Leu Leu Arg Ala Leu Gln Pro Leu Glu Glu Gly Glu Asp Glu Lys
Val Ser His Gln Ala Gly Asp His Trp Leu Ile Arg Gly Pro Leu Glu Tyr Val
Pro Ser Ala Lys Val Glu Val Val Glu Glu Arg Gln Ala Ile Pro Leu Asp Glu
Asn Glu Gly Ile Tyr Val Gln Asp Val Lys Thr Gly Lys Val Arg Ala Val Ile
Gly Ser Thr Tyr Met Leu Thr Gln Asp Glu Val Leu Trp Glu Lys Glu Leu Pro
Pro Gly Val Glu Glu Leu Leu Asn Lys Gly Gln Asp Pro Leu Ala Asp Arg Gly
Glu Lys Asp Thr Ala Lys Ser Leu Gln Pro Leu Ala Pro Arg Asn Lys Thr Arg
Val Val Ser Tyr Arg Val Pro His Asn Ala Ala Val Gln Val Tyr Asp Tyr Arg
Glu Lys Arg Ala Arg Val Val Phe Gly Pro Glu Leu Val Ser Leu Gly Pro Glu
Glu Gln Phe Thr Val Leu Ser Leu Ser Ala Gly Arg Pro Lys Arg Pro His Ala
Arg Arg Ala Leu Cys Leu Leu Leu Gly Pro Asp Phe Phe Thr Asp Val Ile Thr
Ile Glu Thr Ala Asp His Ala Arg Leu Gln Leu Gln Leu Ala Tyr Asn Trp His
Phe Glu Val Asn Asp Arg Lys Asp Pro Gln Glu Thr Ala Lys Leu Phe Ser Val
Pro Asp Phe Val Gly Asp Ala Cys Lys Ala Ile Ala Ser Arg Val Arg Gly Ala
Val Ala Ser Val Thr Phe Asp Asp Phe His Lys Asn Ser Ala Arg Ile Ile Arg
Thr Ala Val Phe Gly Phe Glu Thr Ser Glu Ala Lys Gly Pro Asp Gly Met Ala
Leu Pro Arg Pro Arg Asp Gln Ala Val Phe Pro Gln Asn Gly Leu Val Val Ser
Ser Val Asp Val Gln Ser Val Glu Pro Val Asp Gln Arg Thr Arg Asp Ala Leu
Gln Arg Ser Val Gln Leu Ala Ile Glu Ile Thr Thr Asn Ser Gln Glu Ala Ala
Ala Lys His Glu Ala Arg Leu Glu Arg Glu Ala Arg Gly Arg Leu Glu Arg Gln
Lys Ile Leu Asp Gln Ser Glu Ala Glu Lys Ala Arg Lys Glu Leu Leu Glu
Leu Glu Ala Leu Ser Met Ala Val Glu Ser Thr Gly Thr Ala Lys Ala Glu Ala
Glu Ser Arg Ala Glu Ala Ala Arg Ile Glu Gly Glu Gly Ser Val Leu Gln Ala
Lys Leu Lys Ala Gln Ala Leu Ala Ile Glu Thr Glu Ala Glu Leu Gln Arg Val
Gln Lys Val Arg Glu Leu Glu Leu Val Tyr Ala Arg Ala Gln Leu Glu Leu Glu
Val Ser Lys Ala Gln Gln Leu Ala Glu Val Glu Val Lys Lys Phe Lys Gln Met
Thr Glu Ala Ile Gly Pro Ser Thr Ile Arg Asp Leu Ala Val Ala Gly Pro Glu
Met Gln Val Lys Leu Leu Gln Ser Leu Gly Leu Lys Ser Thr Leu Ile Thr Asp
Gly Ser Thr Pro Ile Asn Leu Phe Asn Thr Ala Phe Gly Leu Leu Gly Met Gly
Pro Glu Gly Gln Pro Leu Gly Arg Arg Val Ala Ser Gly Pro Ser Pro Gly Glu
Gly Ile Ser Pro Gln Ser Ala Gln Ala Pro Gln Ala Pro Gly Asp Asn His Val
Val Pro Val Leu Arg SEQ ID NO: 10 CP-MVP cDNA
atggcaggct gcggttgtcc atgcggttgt ggcgccatgg caactgaaga gttcatcatc
cgcatccccc cataccacta tatccatgtg ctggaccaga acagcaacgt gtcccgtgtg
gaggtcgggc caaagaccta catccggcag gacaatgaag gggtactgtt tgccccacatg
cgcatggtga ccgtcccccc acgtcactac tgcacagtgg ccaaccctgt gtctcgggat
gcccagggct tggtgctgtt tgatgtcaca gggcaagttc ggcttcgcca cgctgacctc
gagatccggc tggcccagga ccccttcccc ctgtaccag gggaggtgct ggaaaaggac
atcacacccc tgcaggtggt tctgcccaac actgccctcc atctaaaggc gctgcttgat
tttgaggata aagatggaga caaggtggtg gcaggagatg agtggctttt cgagggacct
ggcacgtaca tcccccggaa ggaagtggag gtcgtggaga tcattcaggc caccatcatc
aggcagaacc aggctctgcg gctcagggcc cgcaaggagt gctgggaccg ggacggcaag
gagagggtga caggggaaga atggctggtc accacagtag gggcgtacct cccagcggtg
tttgaggagg ttctggattt ggtggacgcc gtcatcctta cggaaaagac agccctgcac
ctccgggctc ggcggaactt ccggacttc aggagagtgt cccgccgcac tggggaggag
tggctggtaa cagtgcagga cacagaggcc acgtgccag atgtccacga ggaggtgctg
ggggttgtgc ccatcaccac cctgggcccc cacaactact gcgtgattct cgaccctgtg
ggaccggatg gcaagaatca gctggggcag aagcgcgtgg tcaagggaga aagtcttt
ttcctccagc caggagagca gctggaacaa ggcatccagg atgtgtatgt gctgtcggag
cagcagggggc tgctgctgag ggccctgcag ccctggagg aggggggaga tgaggagaag
gtctcacacc aggctgggga ccactggctc atccgcggac ccctggagta tgtgccatct
gccaaagtgg aggtggtgga ggagcgccaa gccatccctc tagacgagaa cgagggcatc
tatgtgcagg atgtcaagac cggaaaggtg cgcgctgtga ttggaagcac ctacatgctg
acccaggacg aagtcctgtg ggagaaagag ctgcctcccg ggtgagga gctgctgaac
aaggggcagg acccctctggc agacaggggt gagaaggaca cagctaagag cctccagccc
ttggcgcccc ggaacaagac ccgtgtggtc agctaccgcg tgccccacaa cgctgcggtg
caggtgtacg actaccgaga gaagcgagcc cgcgtggtct cgggcctga ctggtgtcg
ctgggtcctg aggagcagtt cacagtgttg tccctctcag ctgggcggcc caagcgtccc
catgcccgcc gtgcgctctg cctgctgctg gggcctgact tcttcacaga cgtcatcacc
atcgaaacgg cggatcatgc caggctgcaa ctgcagctgg cctacaactg gcactttgag

TABLE 1 -continued

Sequences

```
gtgaatgacc ggaaggaccc ccaagagacg gccaagctct tttcagtgcc agactttgta
ggtgatgcct gcaaagccat cgcatcccgg gtgcgggggg ccgtggcctc tgtcactttc
gatgacttcc ataagaactc agcccgcatc attcgcactg ctgtctttgg ctttgagacc
tcggaagcga agggccccga tggcatggcc ctgcccaggc cccgggacca ggctgtcttc
ccccaaaacg ggctggtggt cagcagtgtg gacgtgcagt cagtggagcc tgtggatcag
aggacccggg acgccctgca acgcagcgtc cagctggcca tcgagatcac caccaactcc
caggaagcgg cggccaagca tgaggctcag agactggagc aggaagcccg cggccggctt
gagcggcaga agatcctgga ccagtcagaa gccgagaaag ctcgcaagga acttttggag
ctggaggctc tgagcatggc cgtggagagc accgggactg ccaaggcgga ggccgagtcc
cgtgcggagg cagcccggat tgaggagaa gggtccgtgc tgcaggccaa gctaaaagca
caggccttgg ccattgaaac ggaggctgag tccagaaggt ccagagagctg
gaactggtct atgccggggc ccagctggag ctggaggtga gcaaggctca gcagctggct
gaggtggagg tgaagaagtt caagcagatg acagaggcca taggccccag caccatcagg
gaccttgctg tggctgggcc tgagatgcag gtaaaactgc tccagtccct gggcctgaaa
tcaaccctca tcaccgatgg ctccactccc atcaacctct tcaacacagc ctttgggctg
ctggggatgg ggcccgaggg tcagcccctg ggcagaaggg tggccagtgg gcccagccct
ggggagggga tatcccccca gtctgctcag gccccctcaag ctcctggaga caaccacgtg
gtgcctgtac tgcgctaa
```

SEQ ID NO: 11 TEP1, Genbank #AAC51107

```
Met Glu Lys Leu His Gly His Val Ser Ala His Pro Asp Ile Leu Ser Leu Glu
Asn Arg Cys Leu Ala Met Leu Pro Asp Leu Gln Pro Leu Glu Lys Leu His Gln
Val Ser Thr His Ser Asp Ile Leu Ser Leu Asn Gln Cys Leu Ala Thr
Leu Pro Asp Leu Lys Thr Met Glu Lys Pro His Gly Tyr Val Ser Ala His Pro
Asp Ile Leu Ser Leu Glu Asn Gln Cys Leu Ala Thr Leu Ser Asp Leu Lys Thr
Met Glu Lys Pro His Gly His Val Ser Ala His Pro Asp Ile Leu Ser Leu Glu
Asn Arg Cys Leu Ala Thr Leu Pro Ser Leu Lys Ser Thr Val Ser Ala Ser Pro
Leu Phe Gln Ser Leu Gln Ile Ser His Met Thr Gln Ala Asp Leu Tyr Arg Val
Asn Asn Ser Asn Cys Leu Leu Ser Glu Pro Pro Ser Trp Arg Ala Gln His Phe
Ser Lys Gly Leu Asp Leu Ser Thr Cys Pro Ile Ala Leu Lys Ser Ile Ser Ala
Thr Glu Thr Ala Gln Glu Ala Thr Leu Gly Arg Trp Phe Asp Ser Glu Glu Lys
Lys Gly Ala Glu Thr Gln Met Pro Ser Tyr Ser Leu Ser Leu Gly Glu Glu
Glu Val Glu Asp Leu Ala Val Lys Leu Thr Ser Gly Asp Ser Glu Ser His Pro
Glu Pro Thr Asp His Val Leu Gln Glu Lys Lys Met Ala Leu Leu Ser Leu Leu
Cys Ser Thr Leu Val Ser Glu Val Asn Met Asn Asn Thr Ser Asp Pro Thr Leu
Ala Ala Ile Phe Glu Ile Cys Arg Glu Leu Ala Leu Glu Leu Pro Glu Phe Ile
Leu Lys Ala Ser Leu Tyr Ala Arg Gln Gln Leu Asn Val Arg Asn Val Ala Asn
Asn Ile Leu Ala Ile Ala Ala Phe Leu Pro Ala Cys Arg Pro His Leu Arg Arg
Tyr Phe Cys Ala Ile Val Gln Leu Pro Ser Asp Trp Ile Gln Val Ala Glu Leu
Tyr Gln Asn Ser Leu Ala Glu Gly Asp Lys Asn Lys Leu Val Pro Leu Pro Ala Cys
Leu Arg Thr Ala Met Thr Asp Lys Phe Ala Gln Phe Asp Glu Tyr Gln Leu Ala
Lys Tyr Asn Pro Arg Lys His Arg Ala Lys Arg His Pro Arg Arg Pro Pro Arg
Ser Pro Gly Met Glu Pro Pro Phe Ser His Arg Cys Phe Pro Arg Tyr Ile Gly
Phe Leu Arg Glu Glu Gln Arg Lys Phe Glu Lys Ala Gly Asp Thr Val Ser Glu
Lys Lys Asn Pro Pro Arg Phe Thr Leu Lys Lys Leu Val Gln Arg Leu His Ile
His Lys Pro Ala Gln His Val Gln Ala Leu Leu Gly Tyr Arg Tyr Pro Ser Asn
Leu Gln Leu Phe Ser Arg Ser Arg Leu Pro Gly Pro Trp Asp Ser Ser Arg Ala
Gly Lys Arg Met Lys Leu Ser Arg Pro Glu Thr Trp Glu Glu Leu Ser Leu
Arg Gly Asn Lys Ala Ser Val Trp Glu Glu Leu Ile Glu Asn Gly Lys Leu Pro
Phe Met Ala Met Leu Arg Asn Leu Cys Asn Leu Leu Arg Val Gly Ile Ser Ser
Arg His His Glu Leu Ile Leu Gln Arg Leu Gln His Gly Lys Ser Val Ile His
Ser Arg Gln Phe Pro Phe Arg Phe Leu Asn Ala His Asp Ala Ile Ala Asp Ala Leu
Glu Ala Gln Leu Arg Asn Gln Ala Leu Pro Phe Pro Ser Asn Ile Thr Leu Met
Arg Arg Ile Leu Thr Arg Asn Glu Lys Asn Arg Pro Arg Arg Phe Leu Cys
His Leu Ser Arg Gln Gln Leu Arg Met Ala Met Arg Ile Pro Val Leu Tyr Glu
Gln Leu Lys Arg Glu Lys Arg Val Leu His Lys Ala Arg Gln Trp Lys Tyr Asp
Gly Glu Met Leu Asn Arg Tyr Arg Gln Ala Leu Glu Thr Ala Val Asn Leu Ser
Val Lys His Ser Leu Pro Leu Leu Pro Gly Arg Thr Val Leu Val Tyr Leu Thr
Asp Ala Asn Ala Asp Arg Leu Cys Pro Lys Ser Asn Pro Gln Gly Pro Pro Leu
Asn Tyr Ala Leu Leu Leu Ile Gly Met Met Ile Thr Arg Ala Glu Gln Val Asp
Val Val Leu Cys Gly Gly Asp Thr Leu Lys Thr Ala Val Leu Lys Ala Glu Gly
Gly Ile Leu Lys Thr Ala Ile Lys Leu Gln Ala Gln Val Gln Glu Phe Asp Glu
Asn Asp Gly Trp Ser Leu Asn Thr Phe Gly Lys Tyr Leu Leu Ser Leu Ala Gly
Gln Arg Val Pro Val Asp Arg Val Ile Leu Leu Gly Gln Ser Met Asp Asp Gly
Met Ile Asn Val Ala Lys Gln Leu Tyr Trp Gln Arg Val Asn Ser Lys Cys Leu
Phe Val Gly Ile Leu Leu Arg Arg Val Gln Tyr Leu Ser Thr Asp Leu Asn Pro
Asn Asp Val Thr Leu Ser Gly Cys Thr Asp Ala Ile Leu Lys Phe Ile Ala Glu
His Gly Ala Ser His Leu Leu Glu His Val Gly Gln Met Asp Lys Ile Phe Lys
Ile Pro Pro Pro Gly Lys Thr Gly Val Gln Leu Ser Leu Thr Arg Pro Glu Leu Val
Asp Thr Pro Ser Pro Leu Ala Pro Val Ser Gln Gln Gly Trp Arg Ser Ile Arg
Leu Phe Ile Ser Ser Thr Phe Arg Asp Met His Gly Glu Arg Asp Leu Leu Leu
Arg Ser Val Leu Pro Ala Leu Gln Ala Arg Ala Ala Pro His Arg Ile Ser Leu
His Gly Ile Asp Leu Arg Trp Gly Val Thr Glu Glu Val Thr Arg Ala Asn Arg
Gln Leu Glu Val Cys Leu Gly Glu Val Glu Asn Ala Gln Leu Phe Val Gly Ile
Leu Gly Ser Arg Tyr Gly Tyr Ile Pro Pro Ser Tyr Asn Leu Pro Asp His Pro
His Phe His Trp Ala Gln Gln Tyr Pro Ser Gly Arg Ser Val Thr Glu Met Glu
Val Met Gln Phe Leu Asn Arg Asn Gln Arg Leu Gln Pro Ser Ala Gln Ala Leu
Ile Tyr Phe Arg Asp Ser Ser Phe Leu Ser Ser Val Pro Asp Ala Trp Lys Ser
```

TABLE 1 -continued

Sequences

Asp Phe Val Ser Glu Ser Glu Ala Ala Cys Arg Ile Ser Glu Leu Lys Ser
Tyr Leu Ser Arg Gln Lys Gly Ile Thr Cys Arg Tyr Pro Cys Glu Trp Gly
Gly Val Ala Ala Gly Arg Pro Tyr Val Gly Gly Leu Glu Glu Phe Gly Gln Leu
Val Leu Gln Asp Val Trp Asn Met Ile Gln Lys Leu Tyr Leu Gln Pro Gly Ala
Leu Leu Glu Gln Pro Val Ser Ile Pro Asp Asp Leu Val Gln Ala Thr Phe
Gln Gln Leu Gln Lys Pro Pro Ser Pro Ala Arg Pro Arg Leu Leu Gln Asp Thr
Val Gln Gln Leu Met Leu Pro His Gly Arg Leu Ser Leu Val Thr Gly Gln Ser
Gly Gln Gly Lys Thr Ala Phe Leu Ala Ser Leu Val Ser Ala Leu Gln Ala Pro
Asp Gly Ala Lys Val Ala Pro Leu Val Phe His Phe Ser Gly Ala Arg Pro
Asp Gln Gly Leu Ala Leu Thr Leu Leu Arg Arg Leu Cys Thr Tyr Leu Arg Gly
Gln Leu Lys Glu Pro Gly Ala Leu Pro Ser Thr Tyr Arg Ser Leu Val Trp Glu
Leu Gln Gln Arg Leu Leu Pro Lys Ser Ala Glu Ser Leu His Pro Gly Gln Thr
Gln Val Leu Ile Ile Asp Gly Ala Asp Arg Leu Val Asp Gln Asn Gly Gln Leu
Ile Ser Asp Trp Ile Pro Lys Lys Leu Pro Arg Cys Val His Leu Val Leu Ser
Val Ser Ser Asp Ala Gly Leu Gly Glu Thr Leu Glu Gln Ser Gln Gly Ala His
Val Leu Ala Leu Gly Pro Leu Glu Ala Ser Ala Arg Ala Arg Leu Val Arg Glu
Glu Leu Ala Leu Tyr Gly Lys Arg Leu Glu Glu Ser Pro Phe Asn Asn Gln Met
Arg Leu Leu Leu Val Lys Arg Glu Ser Gly Arg Pro Leu Tyr Leu Arg Leu Val
Thr Asp His Leu Arg Leu Phe Thr Leu Tyr Glu Val Ser Glu Val Arg Leu Arg
Thr Leu Pro Ala Thr Val Pro Leu Leu Leu Gln His Ile Leu Ser Thr Leu Glu
Lys Glu His Gly Pro Asp Val Leu Pro Gln Ala Leu Thr Ala Leu Glu Val Thr
Arg Ser Gly Leu Thr Val Asp Gln Leu His Gly Val Leu Ser Val Trp Arg Thr
Leu Pro Lys Gly Thr Lys Ser Trp Glu Glu Val Ala Val Ala Ala Gly Leu Asn Ser Gly
Asp Pro Tyr Pro Met Gly Pro Phe Ala Cys Leu Val Gln Ser Leu Arg Ser Leu
Leu Gly Glu Gly Pro Leu Glu Arg Pro Gly Ala Arg Leu Cys Leu Pro Asp Gly
Pro Leu Arg Thr Ala Ala Lys Arg Cys Tyr Gly Lys Arg Pro Gly Leu Glu Asp
Thr Ala His Ile Leu Ile Ala Ala Gln Leu Trp Lys Thr Cys Asp Ala Asp Ala
Ser Gly Thr Phe Arg Ser Cys Pro Pro Glu Ala Leu Gly Asp Leu Pro Tyr His
Leu Leu Gln Ser Gly Asn Arg Gly Leu Leu Ser Lys Phe Leu Thr Asn Leu His
Val Val Ala Ala His Leu Glu Leu Gly Leu Val Ser Arg Leu Leu Glu Ala His
Ala Leu Tyr Ala Ser Ser Val Pro Lys Glu Gln Lys Leu Pro Glu Leu Ala Asp
Val Ala Val Phe Arg Thr Phe Leu Arg Gln Gln Ala Ser Ile Leu Ser Gln Tyr
Pro Arg Leu Leu Pro Gln Gln Ala Ala Asn Gln Pro Leu Asp Ser Pro Leu Cys
His Gln Ala Ser Leu Leu Ser Arg Arg Trp His Leu Gln His Thr Leu Arg Trp
Leu Asn Lys Pro Arg Thr Met Lys Asn Gln Gln Ser Ser Ser Leu Ser Leu Ala
Val Ser Ser Ser Pro Thr Ala Val Ala Phe Ser Thr Asn Gly Gln Arg Ala Ala
Val Gly Thr Ala Asn Gly Thr Val Tyr Leu Leu Asp Leu Arg Thr Trp Gln Glu
Glu Lys Ser Val Val Ser Gly Cys Asp Gly Ile Ser Als Cys Leu Phe Leu Ser
Asp Asp Thr Leu Phe Leu Thr Ala Phe Asp Gly Leu Leu Glu Leu Trp Asp Leu
Gln His Gly Cys Arg Val Leu Gln Thr Lys Ala His Gly Tyr Gln Ile Thr Gly
Cys Cys Leu Ser Pro Asp Cys Arg Leu Leu Ala Thr Val Cys Leu Gly Gly Cys
Leu Lys Leu Trp Asp Thr Val Arg Gly Gln Leu Ala Phe Gln His Thr Tyr Pro
Lys Ser Leu Asn Cys Val Ala Phe His Pro Glu Gly Gln Val Ile Ala Thr Gly
Ser Ala Gly Ser Ile Ser Phe Phe Gln Val Asp Gly Leu Lys Val Thr Lys Lys
Asp Leu Gly Ala Pro Gly Ala Ser Ile Arg Thr Leu Ala Phe Asn Val Pro Gly
Gly Val Val Ala Val Gly Arg Leu Asp Ser Met Val Glu Leu Trp Ala Trp Arg
Glu Gly Ala Arg Leu Ala Ala Phe Pro Ala His His Gly Phe Val Ala Ala Ala
Leu Phe Leu His Ala Gly Cys Gln Leu Leu Thr Ala Gly Leu Gly Asp Gly Lys Val
Gln Val Trp Ser Gly Ser Leu Gly Arg Pro Arg Gly His Leu Gly Ser Leu Ser
Leu Ser Pro Ala Leu Ser Val Ala Leu Ser Pro Asp Gly Asp Arg Val Ala Val
Gly Tyr Arg Ala Asp Gly Ile Arg Ile Tyr Lys Ile Ser Ser Gly Ser Gln Gly
Ala Gln Gly Gln Ala Leu Asp Val Ala Val Ser Arg Leu Ala Trp Leu Pro
Lys Val Leu Val Ser Gly Ala Glu Asp Gly Ser Leu Gln Gly Trp Ala Leu Lys
Glu Cys Ser Leu Gln Ser Leu Trp Leu Leu Ser Arg Phe Gln Lys Pro Val Leu
Gly Leu Ala Thr Ser Gln Glu Leu Leu Ala Ser Ala Ser Glu Asp Phe Thr Val
Gln Leu Trp Pro Arg Gln Leu Leu Thr Arg Pro His Lys Ala Glu Asp Phe Pro
Cys Gly Thr Glu Leu Arg Gly His Glu Gly Pro Val Ser Cys Cys Ser Phe Ser
Thr Asp Gly Gly Ser Leu Ala Thr Gly Gly Arg Asp Arg Ser Leu Leu Cys Trp
Asp Val Arg Thr Pro Lys Thr Pro Val Leu Ile His Ser Phe Pro Ala Cys His
Arg Asp Trp Val Thr Gly Cys Ala Trp Thr Lys Asp Asn Leu Leu Ile Ser Cys
Ser Ser Asp Gly Ser Val Gly Leu Trp Asp Pro Gly Ser Gly Arg Leu Gly Gly
Gln Phe Leu Gly His Gln Ser Ala Val Ser Ala Val Ala Ala Val Glu Glu His
Val Val Ser Val Ser Arg Asp Gly Thr Leu Lys Val Trp Asp His Gln Gly Val
Glu Leu Thr Ser Ile Pro Ala His Ser Gly Pro Ile Ser His Cys Ala Ala Ala
Met Glu Pro Arg Ala Ala Gly Gln Pro Gly Ser Leu Leu Val Val Thr Val
Gly Leu Asp Gly Ala Thr Arg Leu Trp His Pro Leu Leu Val Cys Gln Thr His
Thr Leu Leu Gly His Ser Gly Pro Val Arg Ala Ala Val Ser Glu Thr Ser
Gly Leu Met Leu Thr Ala Ser Glu Asp Gly Ser Val Arg Leu Trp Gln Val Pro
Lys Glu Ala Asp Asp Thr Cys Ile Pro Arg Ser Arg Ser Ala Ala Val Thr Ala Val
Ala Trp Ala Pro Asp Gly Ser Met Ala Val Ser Gly Asn Gln Ala Gly Glu Leu
Ile Leu Trp Gln Glu Ala Lys Ala Val Ala Thr Ala Gln Ala Pro Gly His Ile
Gly Ala Leu Ile Trp Ser Ser Ala His Thr Phe Phe Val Leu Ser Ala Asp Glu
Lys Ile Ser Glu Trp Gln Val Lys Leu Arg Gly Ser Ala Pro Gly Asn Leu
Ser Leu His Leu Asn Arg Ile Leu Gln Glu Asp Leu Gly Val Leu Thr Ser Leu
Asp Trp Ala Pro Asp Gly His Phe Leu Ile Leu Ala Lys Ala Asp Leu Lys Leu
Leu Cys Met Lys Pro Gly Asp Ala Pro Ser Glu Ile Trp Ser Ser Tyr Thr Glu
Asn Pro Met Ile Leu Ser Thr His Lys Glu Tyr Gly Ile Phe Val Leu Gln Pro
Lys Asp Pro Gly Val Leu Ser Phe Leu Arg Gln Lys Glu Ser Gly Glu Phe Glu

TABLE 1 -continued

Sequences

Glu Arg Leu Asn Phe Asp Ile Asn Leu Glu Asn Pro Ser Arg Thr Leu Ile Ser
Ile Thr Gln Ala Lys Pro Glu Ser Glu Ser Ser Phe Leu Cys Ala Ser Ser Asp
Gly Ile Leu Trp Asn Leu Ala Lys Cys Ser Pro Glu Gly Glu Trp Thr Thr Gly
Asn Met Trp Gln Lys Lys Ala Asn Thr Pro Glu Thr Gln Thr Pro Gly Thr Asp
Pro Ser Thr Cys Arg Glu Ser Asp Ala Ser Met Asp Ser Asp Ala Ser Met Asp
Ser Glu Pro Thr Pro His Leu Lys Thr Arg Gln Arg Arg Lys Ile His Ser Gly
Ser Val Thr Ala Leu His Val Leu Pro Glu Leu Leu Val Thr Ala Ser Lys Asp
Arg Asp Val Lys Leu Trp Glu Arg Pro Ser Met Gln Leu Leu Gly Leu Phe Arg
Cys Glu Gly Ser Val Ser Cys Leu Glu Pro Trp Leu Gly Ala Asn Ser Thr Leu
Gln Leu Ala Val Gly Asp Val Gln Gly Asn Val Tyr Phe Leu Asn Trp Glu

SEQ ID NO: 12 TEP1 cDNA, Genbank #U86136
atggaaaaac tccatgggca tgtgtctgcc catccagaca tcctctcctt ggagaaccgg
tgcctggcta tgctccctga cttacagccc ttggagaaac tacatcagca tgtatctacc
cactcagata tcctctcctt gaagaaccag tgcctgactg cgcttcctga cctgaagacc
atggaaaaac cacatggata tgtgtctgcc cacccagaca tcctctcctt ggagaaccag
tgcctggcca cactttctga cctgaagacc atggagaaac cacatggaca tgtttctgcc
cacccagaca tcctctcctt ggagaaccgg tgcctggcca ccctccctag tctaaagagc
actgtgtctg ccagcccctt gttccagagt tacagatat ctcacatgac gcaagctgat
ttgtaccgtg tgaacaacag caattgcctg ctctctgagc ctccaagttg gagggctcag
catttctcta agggactaga cctttcaacc tgcctatag ccctgaaatc catctctgcc
acagagacag ctcaggaagc aactttgggt cgttggtttg attcagaaga gaagaaggg
gcagagaccc aaatgccttc ttatagtctg agcttgggag aggaggagga ggtggaggat
ctggccgtga agctcacctc tggagactct gaatctcatc cagagcctac tgaccatgtc
cttcaggaaa agaagatggc tctactgagc ttgctgtgct ctactctggt ctcagaagta
aacatgaaca atacatctga cccccaccct gctgccattt ttgaaatctg tcgtgaactt
gccctcctgg agcctgagtt tatcctcaag gcatctttgt atgccaggca gcagctgaac
gtccggaatg tggccaataa catcttggcc attgctgctt tcttgccggc gtgtcgcccc
cacctgcgac gatatttctg tgccattgtc cagctgcctt ctgactggat ccaggtggct
gagctttacc agagcctggc tgagggagat aagaataagc tggtgcccct gcccgcctgt
ctccgtactg ccatgacgga caaatttgcc cagtttgacg agtaccagct ggctaagtac
aaccctcgga agcaccgggc caagagacac ccccgccggc caccccgctc tcagggatg
gagcctccat tttctcacag atgttttcca aggtacatag ggtttctcag agaagagcag
agaaagtttg agaaggccgg tgatacagtg tcagagaaaa agaatcctcc aaggttcacc
ctgaagaagc tggttcagcg actgcacatc cacaagcctg cccagcacgt tcaagccctg
ctgggttaca gatacccctc caacctacag ctctttctgt gaagtcgcct tcctgggcct
tgggattcta gcagagctgg gaagaggatg aagctgtcta ggccagagac tgggagcgg
gagctgagcc tacggggggaa caaagcgtcg gtctgggagg aactcattga aaatgggaag
cttcccttca tggccatgct tcggaacctg tgcaacctgc tgcgggttgg aatcagttcc
cgccaccatg agctcattct ccagagactc cagcatggga atcggtgat ccacagtgg
cagtttccat tcagatttct taacgcccat gatgccattg atgccctcga ggctcaactc
agaaatcaag cattgccctt tccttcgaat ataacactga tgaggcggat actaactaga
aatgaaagaa ccgtcccag gcggaggttt ctttgccacc taagccgtca gcagcttcgt
atggcaatga ggatacctgt gttgtatgag cagctcacag gggagaagct gagagtacac
aaggccagac agtggaaata tgatggtgag atgctgaaca ggtaccgaca ggccctagag
acagctgtga acctctctgt gaagcacagc ctgcccctgc tgccaggccg cactgtcttg
gtctatctga cagatgctaa tgcagacagg ctctgtccaa agagcaaccc acaagggccc
ccgctgaact atgcactgct gttgattggg atgatgatca cgagggcgga gcaggtggac
gtcgtgctgt gtggaggtga cactctgaag actgcagtgc ttaaggcaga agaaggcatc
ctgaagactg ccatcaagct ccaggctcaa gtccaggagt ttgatgaaaa tgatggatgg
tccctgaata cttttgggaa ataccctgctg tctctggctg gccaaggggt tcctgtggac
agggtcatcc tccttggcca aagcatggat gatgaaatga taaatgtgcc caaacagctt
tactggcagc gtgtgaattc caagtgcctc tttgttggta tcctcctaag aagggtacaa
tacctgtcaa cagatttgaa tcccaatgat gtgacactct caggctgtac tgatgcgata
ctgaagttca ttgcagagca tggggcctcc atcttctgg aacatgtggg ccaaatggac
aaaatattca agattccacc ccccccagga aagacagggg tccagtctct ccggccactg
gaagaggaca ctccaagccc cttggctcct gttccccagc aaggatggcc cagcatccgg
cttttcattt catccactt ccgagacatg cacggggagc gggacctgct gctgaggtct
gtgctgccag cactgcaggc ccgagcggcc cctcaccgta tcagccttca cggaatcgac
ctccgctggg gcgtcactga ggaggagacc cgtaggaaca gacaactgga agtgtgcctt
ggggaggtgg agaacgcaca gctgtttgtg gggattctgg gctcccgtta tggatacatt
ccccccagct acaaccttcc tgaccatcca cacttccact gggcccagca gtacccttca
gggcgctctg tgcagagat ggaggtgatg cagttcctga accggaacca acgtctgcag
ccctctgccc aagctctcat ctacttccgg gattccagct cctcagctc tgtgccagat
gcctggaaat ctgactttgt ttctgagtct gaagaggccg catgtcggat ctcagaactg
aagagctacc taagcagaca gaaagggata acctgccgca gatacccctg tgagtggggg
ggtgtggcag ctgccggcc ctatgttggc gggctgagg agtttgggca gttggttctg
caggatgtat ggaatatgat ccagaagctc tacctgcagc ctgggcccct gctggagcag
ccagtgtcca tcccagacga tgacttgtc caggccatt tccagcagct gcagaagcca
ccgagtcctg cccggccacg ccttcttcag gacacagtgc aacagctgat gctgcccac
ggaaggctga gcctggtgac ggggcagtca ggacagggca agacagcctt cctggcatct
cttgtgtcag ccctgcaggc tcctgatggg gccaaggtgg caccattagt cttcttccac
ttctctgggg ctcagcctct ctgactcaga cgcctctgta
tatctgcgtg gccaactaaa agagtcaggt gccctcccca gcacctaccg aagcctggtg
tgggagctgc agcagaggct gctgcccaag tctgctgagt ccctgcatcc tggccagacc
caggtcctga tcatcgatgg ggctgatagg ttagtggacc agaatgggca gctgatttca
gactggatcc aaagaagct tccccggtgt gtacacctgg tgctgagtgt gtctagtgat
gcaggcctag gggagaccct tgagcagagc cagggtgccc acgtgctggc cttggggcct TABLE 1 -continued Sequences ctggaggcct ctgctcgggc ccggctggtg agagaggagc tggccctgta cgggaagcgg
ctggaggagt caccatttaa caaccagatg cgactgctgc tggtgaagcg ggaatcaggc
cggccgctct acctgcgctt ggtcaccgat cacctgaggc tcttcacgct gtatgagcag
gtgtctgaga gactccggac cctgcctgcc actgtccccc tgctgctgca gcacatcctg
agcacactgg agaaggagca cgggcctgat gtccttcccc aggccttgac tgccctagaa
gtcacacgga gtggtttgac tgtggaccag ctgcacggag tgctgagtgt gtggcggaca
ctaccgaagg ggactaagag ctgggaagaa gcagtggctg ctggtaacag tggagacccc
taccccatgg gcccgtttgc ctgcctcgtc cagagtctgc gcagtttgct aggggagggc
cctctggagc gccctggtgc ccggctgtgc ctccctgatg ggccctgag aacagcagct
aaacgttgct atgggaagag gccagggcta aggacacgg cacacatcct cattgcagct
cagctctgga agacatgtga cgctgatgcc tcaggcacct tccgaagttg ccctcctgag
gctctgggag acctgcctta ccacctgctc cagagcggga accgtggact tctttcgaag
ttccttacca acctccatgt ggtggctgca cacttggaat tgggtctggt ctctcggctc
ttggaggccc atgccctcta tgcttcttca gtccccaaag aggaacaaaa gctcccgag
gctgacgttg cagtgtttcg cacctccctg aggcagcagg cttcaatcct cagccagtac
ccccggctcc tgcccagca ggcagccaac cagccctgg actcacctct ttgccaccaa
gcctcgctgc tctccggag atggcacctc caacacacac tacgatggct taataaaccc
cggaccatga aaaatcagca aagctccagc ctgtctctgg cagtttcctc atcccctact
gctgtggcct tctccaccaa tgggcaaaga gcagctgtgg gcactgccaa tgggacagtt
tacctgttgg acctgagaac ttggcaggag gagaagtctg tggtgagtgg ctgtgatgga
atctctgctt gtttgttcct ctccgatgat acactctttc ttactgcctt cgacgggctc
ctggagctct gggacctgca gcatggttgt cgggtgctgc agactaaggc tcaccagtac
caaatcactg gctgctgcct gagcccagac tgccggctgc tagccaccgt gtgcttggga
ggatgcctaa agctgtggga cacagtccgt gggcagctgg ccttccagca cacctacccc
aagtccctga actgtgttgc cttccaccca gaggggcagg taatagccac aggcagctgg
gctggcagca tcagcttctt ccaggtggat gggctcaaag tcaccaagga cctgggggca
cccggagcct ctatccgtac cttggccttc aatgtgcctg gggggttgt ggctgtgggc
cggctggaca gtatggtgga gctgtgggcc tggcgagaag gggcacggct ggctgccttc
cctgcccacc atggctttgt tgctgctgcg cttttcctgc atgcgggttg ccagttactg
acggctggag aggatggcaa ggttcaggtg tggtcagggt ctctgggtcg gccccgtggg
cacctgggtt ccctttctct ctctcctgcc ctctctgtgg cactcagccc agatggtgat
cgggtgctg ttggatatcg agcggatggc attaggatct acaaaatctc ttcaggttcc
cagggggctc agggtcaggc actggatgtg gcagtgtccg ccctggcctg gctaagcccc
aagtattgg tgagtggtgc agaagatggg tccttgcagg gctgggcact caaggaatgc
tcccttcagt ccctctggct cctgtccaga ttccagaagc ctgtgctagg actggccact
tcccaggagc tcttggcttc tgcctcagag gatttcacag tgcagctgtg gccaaggcag
ctgctgacgc ggccacacaa ggcagaagac tttccctgtg gcactgagct gcggggacat
gagggccctg tgagctgctg tagtttcagc actgatggag gcagcctggc caccgggggc
cgggatcgga gtctcctctg ctgggacgtg aggacaccca aaacccctgt tttgatccac
tccttccctg cctgtcaccg tgactgggtc actggctgtg cctggaccaa agataaccta
ctgatatcct gctccagtga tggctctgtg gggctctggg acccagagtc aggacagcgg
cttggtcagt tcctgggtca tcagagtgct gtgagcgctg tggcagctgt ggaggagcac
gtggtgtctg tgagccggga tgggaccttg aaagtgtggg accatcaagg cgtggagctg
accagcatcc ctgctcactc aggacccatt agccactgtg cagctgccat ggagcccatt
gcagctggac agcctgggtc agagcttctg gtggtaaccg tcgggctaga tggggccaca
cggttatggc atccactctt ggtgtgccaa acccacaccc tctgggaca cagcggccca
gtccgtgctg ctgctgtttc agaaacctca ggcctcatgc tgaccgcctc tgaggatggt
tctgtacggc tctggcaggt tcctaaggaa gcagatgaca catgtatacc aaggagttct
gcagccgtca ctgctgtggc ttgggcacca gatggttcca tggcagtatc tggaaatcaa
gctggggaac taatcttgtg gcaggaagct aaggctgtgg ccacagcaca ggctccaggc
cacattggtg ctctgatctg gtcctcggca cacacctttt ttgtcctcag tgctgatgag
aaaatcagcg agtggcaagt gaaactgcgg aagggttcgg caccgggaaa tttgagtctg
cacctgaacc gaattctaca ggaggactta ggggtgctga caagtctgga ttgggctcct
gatggtcact ttctcatctt ggccaaagca gatttgaagt tactttgcat gaagccaggg
gatgctccat ctgaaatctg gagcagctat acagaaaatc ctatgatatt gtccacccac
aaggagtatg gcatatttgt cctgcagccc aaggatcctg gagttctttc tttcttgagg
caaaaggaat caggagagtt tgaagagagg ctgaacttg atataacctt agagaatcct
agtaggaccc taatatcgat aactcaagcc aaacctgaat ctgagtcctc attttttgtgt
gccagctctg atgggatcct atggaacctg ccaaatgca gcccagaagg agaatggacc
acaggtaaca tgtggcagaa aaaagcaaac actccagaaa cccaaactcc agggacagac
ccatctacct gcagggaatc tgatgccagc atggatagtg atgccagcat ggatagtgag
ccaacaccac atctaaagac acggcagcgt agaaagattc actcgggctc tgtcacagcc
ctccatgtgc tacctgagtt gctggtgaca gcttcgaagg acagagatgt taagctatgg
gagagaccca gtatgcagct gctgggcctg ttccgatgcg aagggtcagt gagctgcctg
gaaccttggc tgggcgctaa ctccacccctg cagcttgccg tgggagacgt gcagggcaat
gtgtactttc tgaattggga atga SEQ ID NO: 13 vRNA, Genbank #AF045143
ggcuggcuuu agcucagcgg uuacuucgac aguucuuuaa uugaaacaag caaccugucu
ggguuguucg agacccgcgg gcgcucucca guccuuuu SEQ ID NO: 14 vRNA, Genbank #AF045144
ggcuggcuuu agcucagcgg uuacuucgag ucauuguaa ccaccucucu ggguгgucg
agacccgcgg gugcuuucca gcucuuuu SEQ ID NO: 15 vRNA, Genbank #AF045145
ggcuggcuuu agcucagcgg uuacuucgcg ugucaucaaa ccaccucucu ggguuguucg
agacccgcgg gcgcucucca gcccucuu

TABLE 1 -continued

Sequences

SEQ ID NO: 16 INT protein sequence (residues 1473-1724 of human VPARP protein sequence)

Ala Asn Leu Arg Leu Pro Met Ala Ser Ala Leu Pro Glu Ala Leu Cys Ser Gln
Ser Arg Thr Thr Pro Val Asp Leu Cys Leu Leu Glu Glu Ser Val Gly Ser Leu
Glu Gly Ser Arg Cys Pro Val Phe Ala Phe Gln Ser Ser Asp Thr Glu Ser Asp
Glu Leu Ser Glu Val Leu Gln Asp Ser Cys Phe Ser Gln Ile Lys Cys Asp Thr
Lys Asp Asp Ser Ile Pro Cys Phe Leu Glu Leu Lys Glu Glu Asp Glu Ile Val
Cys Thr Gln His Trp Gln Asp Ala Val Pro Trp Thr Glu Leu Leu Ser Leu Gln
Thr Glu Asp Gly Phe Trp Lys Leu Thr Pro Glu Leu Gly Leu Ile Leu Asn Leu
Asn Thr Asn Gly Leu His Ser Phe Leu Lys Gln Lys Gly Ile Gln Ser Leu Gly
Val Lys Gly Arg Glu Cys Leu Leu Asp Leu Ile Ala Thr Met Leu Val Leu Gln
Phe Ile Arg Thr Arg Leu Glu Lys Glu Gly Ile Val Phe Lys Ser Leu Met Lys
Met Asp Asp Pro Ser Ile Ser Arg Asn Ile Pro Trp Ala Phe Glu Ala Ile Lys
Gln Ala Ser Glu Trp Val Arg Arg Thr Glu Gln Tyr Pro Ser Ile Cys Pro
Arg Leu Glu Leu Gly Asn Asp Trp Asp Ser Ala Thr Lys Gln Leu Leu Gly Leu
Gln Pro Ile Ser Thr Val Ser Pro Leu His Arg Val Leu His Tyr Ser Gln Gly

---

The invention claimed is:

1. A method for stimulating presentation of a tumor antigen to the MHC Class I pathway in dendritic cells in a subject, comprising administering to the subject an effective amount of a vault complex comprising a major vault protein (MVP) and the tumor antigen or an antigenic fragment thereof encapsulated therein.

2. The method of claim 1, further comprising administering to the subject a second vault complex comprising a second tumor antigen or antigenic fragment encapsulated therein.

3. The method of claim 1, wherein the vault complex comprises two or more different tumor antigens or antigenic fragments thereof.

4. The method of claim 1, wherein the tumor antigen is fused to an INT sequence.

5. The method of claim 4, wherein the INT sequence comprises the amino acid sequence of SEQ ID NO: 2.

6. The method of claim 1, wherein the tumor antigen is fused to the MVP.

7. The method of claim 6, wherein the tumor antigen is fused to the N-terminus of the MVP.

8. The method of claim 2, wherein the second vault complex comprises a third tumor antigen or antigenic fragment thereof.

9. The method of claim 1, wherein the vault complex contains 1-78 major vault proteins.

10. The method of claim 1, wherein the vault complex contains 78 major vault proteins.

11. The method of claim 8, wherein the vault complex further comprises a vault poly ADP-ribose polymerase (VPARP).

12. The method of claim 1, wherein the presentation of the tumor antigen results in induction of CD8$^+$ and CD4$^+$ memory T-cells.

13. The method of claim 1, wherein the presentation of the tumor antigen results in production of INFγ.

14. The method of claim 1, further comprising administering to the subject a second vault complex, which comprises a chemokine.

15. The method of claim 14, wherein the chemokine is CCL21.

16. A method for stimulating presentation of a tumor antigen to the MEW Class I pathway in dendritic cells in a subject, comprising administering to the subject a pharmaceutical composition comprising a vault complex having a major vault protein (MVP) and a tumor antigen or an antigenic fragment thereof encapsulated therein and at least one pharmaceutically acceptable excipient.

17. The method of claim 16, wherein tumor antigen is fused to an INT sequence.

18. The method of claim 17, wherein the INT sequence comprises the amino acid sequence of SEQ ID NO: 2.

19. The method of claim 16, wherein the tumor antigen is fused to the MVP.

20. The method of claim 16, wherein the vault complex comprises two or more different tumor antigens or antigenic fragments thereof.

21. The method of claim 16, wherein the vault complex contains 1-78 major vault proteins.

22. The method of claim 16, wherein the vault complex contains 78 major vault proteins.

23. The method of claim 20, wherein the vault complex further comprises a vault poly ADP-ribose polymerase (VPARP).

24. The method of claim 16, wherein the presentation of the tumor antigen results in induction of CD8$^+$ and CD4$^+$ memory T-cells.

25. The method of claim 16, wherein the presentation of the tumor antigen results in production of INFγ.

26. The method of claim 16, further comprising a second vault complex, which contains a chemokine.

27. The method of claim 26, wherein the chemokine is CCL21.

28. A method of stimulating presentation of a tumor antigen to the MHC Class I pathway in dendritic cells in a subject, who has cancer, which comprises administering to the subject an effective amount of a vault complex comprising a major vault protein (MVP) and a tumor antigen or an antigenic fragment thereof encapsulated therein.

29. The method of claim 28, wherein tumor antigen is fused to an INT sequence.

30. The method of claim 29, wherein the INT sequence comprises the amino acid sequence of SEQ ID NO: 2.

31. The method of claim 28, wherein the tumor antigen is fused to MVP.

32. The method of claim 28, and further comprising administering to the subject a second vault complex comprising a second tumor antigen or antigenic fragment encapsulated therein.

33. The method of claim 28, wherein the vault complex contains 1-78 major vault proteins.

34. The method of claim 28, wherein the vault complex contains 78 major vault proteins.

35. The method of claim 32, wherein the vault complex further comprises a vault poly ADP-ribose polymerase (VPARP).

36. The method of claim 28, wherein the presentation of the tumor antigen results in induction of $CD8^+$ and $CD4^+$ memory T-cells.

37. The method of claim 28, wherein the presentation of the tumor antigen results in production of INFγ.

38. The method of claim 28, further comprising administering to the subject a second vault complex, which contains a chemokine.

39. The method of claim 38, wherein the chemokine is CCL21.

40. The method of any one of claims 28-39, wherein the administering reduces tumor volume.

41. The method of any one of claims 28-39, wherein the administering reduces tumor growth.

* * * * *

SEQUENCE LISTING

<160> NUMBER OF SEQ ID NOS: 22

<210> SEQ ID NO 1
<211> LENGTH: 489
<212> TYPE: DNA
<213> ORGANISM: Homo sapiens

<400> SEQUENCE: 1

```
tgcacacaac actggcagga tgctgtgcct tggacagaac tcctcagtct acagacagag      60
gatggcttct ggaaacttac accagaactg ggacttatat aaatcttaa tacaaatggt     120
ttgcacagct ttcttaaaca aaaaggcatt caatctctag gtgtaaaagg aagagaatgt    180
ctcctggacc taattgccac aatgctggta ctacagttta ttcgcaccag gttggaaaaa    240
gagggaatag tgttcaaatc actgatgaaa atggatgacc cttctatttc aggaatatt    300
ccctgggctt ttgaggcaat aaagcaagca agtgaatggg taagaagaac tgaaggacag    360
tacccatcta tctgcccacg gcttgaactg gggaacgact gggactctgc caccaagcag    420
ttgctgggac tccagcccat aagcactgtg tcccctcttc atagagtcct ccattacagt    480
caaggctaa                                                            489
```

<210> SEQ ID NO 2
<211> LENGTH: 162
<212> TYPE: PRT
<213> ORGANISM: Homo sapiens

<400> SEQUENCE: 2

Cys Thr Gln His Trp Gln Asp Ala Val Pro Trp Thr Glu Leu Leu Ser
1               5                   10                  15

Leu Gln Thr Glu Asp Gly Phe Trp Lys Leu Thr Pro Glu Leu Gly Leu
            20                  25                  30

Ile Leu Asn Leu Asn Thr Asn Gly Leu His Ser Phe Leu Lys Gln Lys
        35                  40                  45

Gly Ile Gln Ser Leu Gly Val Lys Gly Arg Glu Cys Leu Leu Asp Leu
    50                  55                  60

Ile Ala Thr Met Leu Val Leu Gln Phe Ile Arg Thr Arg Leu Glu Lys
65                  70                  75                  80

Glu Gly Ile Val Phe Lys Ser Leu Met Lys Met Asp Asp Pro Ser Ile
                85                  90                  95

```
Ser Arg Asn Ile Pro Trp Ala Phe Glu Ala Ile Lys Gln Ala Ser Glu
                100                 105                 110

Trp Val Arg Arg Thr Glu Gly Gln Tyr Pro Ser Ile Cys Pro Arg Leu
            115                 120                 125

Glu Leu Gly Asn Asp Trp Asp Ser Ala Thr Lys Gln Leu Leu Gly Leu
        130                 135                 140

Gln Pro Ile Ser Thr Val Ser Pro Leu His Arg Val Leu His Tyr Ser
145                 150                 155                 160

Gln Gly

<210> SEQ ID NO 3
<211> LENGTH: 1724
<212> TYPE: PRT
<213> ORGANISM: Homo sapiens

<400> SEQUENCE: 3

Met Val Met Gly Ile Phe Ala Asn Cys Ile Phe Cys Leu Lys Val Lys
1               5                   10                  15

Tyr Leu Pro Gln Gln Lys Lys Leu Gln Thr Asp Ile Lys Glu
                20                  25                  30

Asn Gly Gly Lys Phe Ser Phe Ser Leu Asn Pro Gln Cys Thr His Ile
            35                  40                  45

Ile Leu Asp Asn Ala Asp Val Leu Ser Gln Tyr Gln Leu Asn Ser Ile
    50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Asp Gln Lys Ala Ser Ser Ser Glu
                100                 105                 110

Val Lys Thr Glu Gly Leu Cys Pro Asp Ser Ala Thr Glu Glu Glu Asp
            115                 120                 125

Thr Val Glu Leu Thr Glu Phe Gly Met Gln Asn Val Glu Ile Pro His
130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Val Glu Leu Gln Cys Ser
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
        195                 200                 205

Glu Asp Ala Ser Glu Tyr Phe Glu Asn Tyr Ile Glu Glu Leu Lys Lys
    210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Leu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
        275                 280                 285

Ile Ser Leu Asn Asp Val Ser Lys Ala Glu Gly Ile Leu Leu Leu Val
    290                 295                 300
```

```
Lys Ala Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
            325                 330                 335

Glu Val Asn Leu Gly Leu Leu Ala Lys Lys Ala Asp Leu Cys Gln Leu
        340                 345                 350

Ile Arg Asp Met Val Asn Val Cys Glu Thr Asn Leu Ser Lys Pro Asn
            355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                405                 410                 415

Val Gly Arg Val Asn Glu Thr Thr Glu Phe Leu Ser Lys Leu Gly Asn
            420                 425                 430

Val Arg Pro Leu Leu His Gly Ser Pro Val Gln Asn Ile Val Gly Ile
        435                 440                 445

Leu Cys Arg Gly Leu Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480

Ser Leu Ser Thr Ser Ile Lys Tyr Ser His Pro Gly Glu Thr Asp Gly
                485                 490                 495

Thr Arg Leu Leu Leu Ile Cys Asp Val Ala Leu Gly Lys Cys Met Asp
            500                 505                 510

Leu His Glu Lys Asp Phe Pro Leu Thr Glu Ala Pro Pro Gly Tyr Asp
        515                 520                 525

Ser Val His Gly Val Ser Gln Thr Ala Ser Val Thr Thr Asp Phe Glu
    530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                565                 570                 575

Ser Asp His Thr Glu Leu Glu Glu Tyr Arg Pro Glu Phe Ser Asn Phe
            580                 585                 590

Ser Lys Val Glu Asp Tyr Gln Leu Pro Asp Ala Lys Thr Ser Ser Ser
        595                 600                 605

Thr Lys Ala Gly Leu Gln Asp Ala Ser Gly Asn Leu Val Pro Leu Glu
    610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                645                 650                 655

Tyr Ile Phe Pro Leu Asp Asp Lys Ala Ala Val Cys Gly Phe Glu Ala
            660                 665                 670

Phe Ile Asn Gly Lys His Ile Val Gly Glu Ile Lys Glu Lys Glu Glu
        675                 680                 685

Ala Gln Gln Glu Tyr Leu Glu Ala Val Thr Gln Gly His Gly Ala Tyr
    690                 695                 700

Leu Met Ser Gln Asp Ala Pro Asp Val Phe Thr Val Ser Val Gly Asn
705                 710                 715                 720
```

-continued

Leu Pro Pro Lys Ala Lys Val Leu Ile Lys Ile Thr Tyr Ile Thr Glu
            725                 730                 735

Leu Ser Ile Leu Gly Thr Val Gly Val Phe Phe Met Pro Ala Thr Val
            740                 745                 750

Ala Pro Trp Gln Gln Asp Lys Ala Leu Asn Glu Asn Leu Gln Asp Thr
            755                 760                 765

Val Glu Lys Ile Cys Ile Lys Glu Ile Gly Thr Lys Gln Ser Phe Ser
            770                 775                 780

Leu Thr Met Ser Ile Glu Met Pro Tyr Val Ile Glu Phe Ile Phe Ser
785                 790                 795                 800

Asp Thr His Glu Leu Lys Gln Lys Arg Thr Asp Cys Lys Ala Val Ile
            805                 810                 815

Ser Thr Met Glu Gly Ser Ser Leu Asp Ser Ser Gly Phe Ser Leu His
            820                 825                 830

Ile Gly Leu Ser Ala Ala Tyr Leu Pro Arg Met Trp Val Glu Lys His
            835                 840                 845

Pro Glu Lys Glu Ser Glu Ala Cys Met Leu Val Phe Gln Pro Asp Leu
            850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
            885                 890                 895

Gln Ile Thr Leu His Ala Leu Ser Leu Val Gly Glu Lys Gln Lys Val
            900                 905                 910

Asn Ile Ile Gln Phe Gly Thr Gly Tyr Lys Glu Leu Phe Ser Tyr Pro
            915                 920                 925

Lys His Ile Thr Ser Asn Thr Thr Ala Ala Glu Phe Ile Met Ser Ala
            930                 935                 940

Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
            965                 970                 975

Asp Gly His Leu Gln Asp Glu Ser Leu Thr Leu Gln Leu Val Lys Arg
            980                 985                 990

Ser Arg Pro His Thr Arg Leu Phe Ala Cys Gly Ile Gly Ser Thr Ala
            995                 1000                1005

Asn Arg His Val Leu Arg Ile Leu Ser Gln Cys Gly Ala Gly Val
        1010                1015                1020

Phe Glu Tyr Phe Asn Ala Lys Ser Lys His Ser Trp Arg Lys Gln
        1025                1030                1035

Ile Glu Asp Gln Met Thr Arg Leu Cys Ser Pro Ser Cys His Ser
        1040                1045                1050

Val Ser Val Lys Trp Gln Gln Leu Asn Pro Asp Ala Pro Glu Ala
        1055                1060                1065

Leu Gln Ala Pro Ala Gln Val Pro Ser Leu Phe Arg Asn Asp Arg
        1070                1075                1080

Leu Leu Val Tyr Gly Phe Ile Pro His Cys Thr Gln Ala Thr Leu
        1085                1090                1095

Cys Ala Leu Ile Gln Glu Lys Glu Phe Cys Thr Met Val Ser Thr
        1100                1105                1110

Thr Glu Leu Gln Lys Thr Thr Gly Thr Met Ile His Lys Leu Ala
        1115                1120                1125

```
Ala Arg Ala Leu Ile Arg Asp Tyr Glu Asp Gly Ile Leu His Glu
1130                1135                1140

Asn Glu Thr Ser His Glu Met Lys Lys Gln Thr Leu Lys Ser Leu
1145                1150                1155

Ile Ile Lys Leu Ser Lys Glu Asn Ser Leu Ile Thr Gln Phe Thr
1160                1165                1170

Ser Phe Val Ala Val Glu Lys Arg Asp Glu Asn Glu Ser Pro Phe
1175                1180                1185

Pro Asp Ile Pro Lys Val Ser Glu Leu Ile Ala Lys Glu Asp Val
1190                1195                1200

Asp Phe Leu Pro Tyr Met Ser Trp Gln Gly Glu Pro Gln Glu Ala
1205                1210                1215

Val Arg Asn Gln Ser Leu Leu Ala Ser Ser Glu Trp Pro Glu Leu
1220                1225                1230

Arg Leu Ser Lys Arg Lys His Arg Lys Ile Pro Phe Ser Lys Arg
1235                1240                1245

Lys Met Glu Leu Ser Gln Pro Glu Val Ser Glu Asp Phe Glu Glu
1250                1255                1260

Asp Gly Leu Gly Val Leu Pro Ala Phe Thr Ser Asn Leu Glu Arg
1265                1270                1275

Gly Gly Val Glu Lys Leu Leu Asp Leu Ser Trp Thr Glu Ser Cys
1280                1285                1290

Lys Pro Thr Ala Thr Glu Pro Leu Phe Lys Lys Val Ser Pro Trp
1295                1300                1305

Glu Thr Ser Thr Ser Ser Phe Phe Pro Ile Leu Ala Pro Ala Val
1310                1315                1320

Gly Ser Tyr Leu Thr Pro Thr Thr Arg Ala His Ser Pro Ala Ser
1325                1330                1335

Leu Ser Phe Ala Ser Tyr Arg Gln Val Ala Ser Phe Gly Ser Ala
1340                1345                1350

Ala Pro Pro Arg Gln Phe Asp Ala Ser Gln Phe Ser Gln Gly Pro
1355                1360                1365

Val Pro Gly Thr Cys Ala Asp Trp Ile Pro Gln Ser Ala Ser Cys
1370                1375                1380

Pro Thr Gly Pro Pro Gln Asn Pro Pro Ser Ala Pro Tyr Cys Gly
1385                1390                1395

Ile Val Phe Ser Gly Ser Ser Leu Ser Ser Ala Gln Ser Ala Pro
1400                1405                1410

Leu Gln His Pro Gly Gly Phe Thr Thr Arg Pro Ser Ala Gly Thr
1415                1420                1425

Phe Pro Glu Leu Asp Ser Pro Gln Leu His Phe Ser Leu Pro Thr
1430                1435                1440

Asp Pro Asp Pro Ile Arg Gly Phe Gly Ser Tyr His Pro Ser Ala
1445                1450                1455

Tyr Ser Pro Phe His Phe Gln Pro Ser Ala Ala Ser Leu Thr Ala
1460                1465                1470

Asn Leu Arg Leu Pro Met Ala Ser Ala Leu Pro Glu Ala Leu Cys
1475                1480                1485

Ser Gln Ser Arg Thr Thr Pro Val Asp Leu Cys Leu Leu Glu Glu
1490                1495                1500

Ser Val Gly Ser Leu Glu Gly Ser Arg Cys Pro Val Phe Ala Phe
1505                1510                1515
```

| | | | | | | | | | | | |
|---|---|---|---|---|---|---|---|---|---|---|---|
| Gln | Ser | Ser | Asp | Thr | Glu | Ser | Asp | Glu | Leu | Ser | Glu Val Leu Gln |
| | | 1520 | | | | 1525 | | | | 1530 | |

Gln  Ser  Ser  Asp  Thr  Glu  Ser  Asp  Glu  Leu  Ser  Glu  Val  Leu  Gln
         1520                    1525                    1530

Asp  Ser  Cys  Phe  Leu  Gln  Ile  Lys  Cys  Asp  Thr  Lys  Asp  Asp  Ser
  1535                    1540                    1545

Ile  Pro  Cys  Phe  Leu  Glu  Leu  Lys  Glu  Glu  Asp  Glu  Ile  Val  Cys
  1550                    1555                    1560

Thr  Gln  His  Trp  Gln  Asp  Ala  Val  Pro  Trp  Thr  Glu  Leu  Leu  Ser
  1565                    1570                    1575

Leu  Gln  Thr  Glu  Asp  Gly  Phe  Trp  Lys  Leu  Thr  Pro  Glu  Leu  Gly
  1580                    1585                    1590

Leu  Ile  Leu  Asn  Leu  Asn  Thr  Asn  Gly  Leu  His  Ser  Phe  Leu  Lys
  1595                    1600                    1605

Gln  Lys  Gly  Ile  Gln  Ser  Leu  Gly  Val  Lys  Gly  Arg  Glu  Cys  Leu
  1610                    1615                    1620

Leu  Asp  Leu  Ile  Ala  Thr  Met  Leu  Val  Leu  Gln  Phe  Ile  Arg  Thr
  1625                    1630                    1635

Arg  Leu  Glu  Lys  Glu  Gly  Ile  Val  Phe  Lys  Ser  Leu  Met  Lys  Met
  1640                    1645                    1650

Asp  Asp  Pro  Ser  Ile  Ser  Arg  Asn  Ile  Pro  Trp  Ala  Phe  Glu  Ala
  1655                    1660                    1665

Ile  Lys  Gln  Ala  Ser  Glu  Trp  Val  Arg  Arg  Thr  Glu  Gly  Gln  Tyr
  1670                    1675                    1680

Pro  Ser  Ile  Cys  Pro  Arg  Leu  Glu  Leu  Gly  Asn  Asp  Trp  Asp  Ser
  1685                    1690                    1695

Ala  Thr  Lys  Gln  Leu  Leu  Gly  Leu  Gln  Pro  Ile  Ser  Thr  Val  Ser
  1700                    1705                    1710

Pro  Leu  His  Arg  Val  Leu  His  Tyr  Ser  Gln  Gly
  1715                    1720

<210> SEQ ID NO 4

<400> SEQUENCE: 4

000

<210> SEQ ID NO 5
<211> LENGTH: 5175
<212> TYPE: DNA
<213> ORGANISM: Homo sapiens

<400> SEQUENCE: 5

```
atggtgatgg gaatctttgc aaattgtatc ttctgtttga aagtgaagta cttacctcag      60
cagcagaaga aaaagctaca aactgacatt aaggaaaatg gcggaaagtt ttccttttcg     120
ttaaatcctc agtgcacaca tataatctta gataatgctg atgttctgag tcagtaccaa     180
ctgaattcta tccaaaagaa ccacgttcat attgcaaacc cagattttat atggaaatct     240
atcagagaaa agagactctt ggatgtaaag aattatgatc cttataagcc cctggacatc     300
acaccacctc tgatcagaa ggcgagcagt tctgaagtga aaacagaagg tctatgcccg     360
gacagtgcca cagaggagga agacactgtg aactcactg agtttggtat gcagaatgtt     420
gaaattcctc atcttcctca gattttgaa gttgcaaaat ataacaccct tggagaaagtg     480 ggaatggagg gaggccagga agctgtggtg gtggagcttc agtgttcgcg ggactccagg     540
gactgtcctt tcctgatatc ctcacacttc ctcctggatg atggcatgga gactagaaga     600
cagtttgcta taagaaaac ctctgaagat gcaagtgaat acttgaaaa ttacattgaa     660
```

```
gaactgaaga acaaggatt tctactaaga gaacatttca cacctgaagc aacccaatta    720
gcatctgaac aattgcaagc attgcttttg gaggaagtca tgaattcaag cactctgagc    780
caagaggtga gcgatttagt agagatgatt tgggcagagg ccctgggcca cctggaacac    840
atgcttctca agccagtgaa caggattagc ctcaacgatg tgagcaaggc agaggggatt    900
ctccttctag taaaggcagc actgaaaaat ggagaaacag cagagcaatt gcaaaagatg    960
atgacagagt tttacagact gatacctcac aaaggcacaa tgcccaaaga agtgaacctg   1020
ggactattgg ctaagaaagc agacctctgc cagctaataa gagacatggt taatgtctgt   1080
gaaactaatt tgtccaaacc caacccacca tccctggcca aataccgagc tttgaggtgc   1140
aaaattgagc atgttgaaca gaatactgaa gaatttctca gggttagaaa agaggttttg   1200
cagaatcatc acagtaagag cccagtggat gtcttgcaga tatttagagt tggcagagtg   1260
aatgaaacca cagagttttt gagcaaactt ggtaatgtga ggcccttgtt gcatggttct   1320
cctgtacaaa acatcgtggg aatcttgtgt cgagggttgc ttttacccaa agtagtggaa   1380
gatcgtggtg tgcaaagaac agacgtcgga aaccttggaa gtgggattta tttcagtgat   1440
tcgctcagta caagtatcaa gtactcacac ccgggagaga cagatggcac cagactcctg   1500
ctcatttgtg acgtagccct cggaaagtgt atggacttac atgagaagga ctttccctta   1560
actgaagcac caccaggcta cgacagtgtg catggagttt cacaaacagc ctctgtcacc   1620
acagactttg aggatgatga atttgttgtc tataaaacca atcaggttaa aatgaaatat   1680
attattaaat tttccatgcc tggagatcag ataaaggact ttcatcctag tgatcatact   1740
gaattagagg aatacagacc tgagttttca aattttttcaa aggttgaaga ttaccagtta   1800
ccagatgcca aaacttccag cagcaccaag gccggcctcc aggatgcctc tgggaacttg   1860
gttcctctgg aggatgtcca catcaaaggg agaatcatag acactgtagc ccaggtcatt   1920
gtttttcaga catacacaaa taaagtcac gtgcccattg aggcaaaata tatctttcct   1980
ttggatgaca aggccgctgt gtgtggcttc gaagccttca tcaatgggaa gcacatagtt   2040
ggagagatta agagaagga agaagcccag caagagtacc tagaagccgt gacccagggc   2100
catggcgctt acctgatgag tcaggatgct ccggacgttt ttactgtaag tgttggaaac   2160
ttacccccta aggctaaggt tcttataaaa attacctaca tcacagaact cagcatcctg   2220
ggcactgttg tgtctttttt catgcccgcc accgtagcac cctggcaaca ggacaaggct   2280
ttgaatgaaa accttcagga tacagtagag aagatttgta taaagaaat aggaacaaag   2340 caaagcttct ctttgactat gtctattgag atgccgtatg tgattgaatt cattttcagt   2400
gatacacatg aactgaaaca aaagcgcaca gactgcaaag ctgtcattag caccatggaa   2460
ggcagctcct tagacagcag tggatttttct ctccacatcg gtttgtctgc tgcctatctc   2520
ccaagaatgt gggttgaaaa acatccagaa aaagaaagcg aggcttgcat gcttgtcttt   2580
caacccgatc tcgatgtcga cctccctgac ctagccagtg agagcgaagt gattatttgt   2640
cttgactgct ccagttccat ggagggtgtg acattcttgc aagccaagca aatcaccttg   2700
catgcgctgt ccttggtggg tgagaagcag aaagtaaata ttatccagtt cggcacaggt   2760
tacaaggagc tattttcgta tcctaagcat atcacaagca ataccacggc agcagagttc   2820
atcatgtctg ccacacctac catggggaac acagacttct ggaaaacact ccgatatctt   2880
agcttattgt accctgctcg agggtcacgg aacatcctcc tggtgtctga tgggcacctc   2940
caggatgaga gcctgacatt acagctcgtg aagaggagcc gcccgcacac caggttattc   3000
gcctgcggta tcggttctac agcaaatcgt cacgtcttaa ggattttgtc ccagtgtggt   3060
```

```
gccggagtat ttgaatattt taatgcaaaa tccaagcata gttggagaaa acagatagaa    3120
gaccaaatga ccaggctatg ttctccgagt tgccactctg tctccgtcaa atggcagcaa    3180
ctcaatccag atgcgcccga ggccctgcag gccccagccc aggtgccatc cttgtttcgc    3240
aatgatcgac tccttgtcta tggattcatt cctcactgca cacaagcaac tctgtgtgca    3300
ctaattcaag agaaagaatt tgtacaatg gtgtcgacta ctgagcttca gaagacaact     3360
ggaactatga tccacaagct ggcagcccga gctctaatca gagattatga agatggcatt    3420
cttcacgaaa atgaaaccag tcatgagatg aaaaaacaaa ccttgaaatc tctgattatt    3480
aaactcagta agaaaactc tctcataaca caatttacaa gctttgtggc agttgagaaa     3540
agggatgaga atgagtcgcc ttttcctgat attccaaaag tttctgaact tattgccaaa    3600
gaagatgtag acttcctgcc ctacatgagc tggcaggggg agccccaaga agccgtcagg    3660
aaccagtctc ttttagcatc ctctgagtgg ccagaattac gtttatccaa acgaaaacat    3720
aggaaaattc cattttccaa aagaaaaatg gaattatctc agccagaagt ttctgaagat    3780
tttgaagagg atggcttagg tgtactacca gctttcacat caaatttgga acgtggaggt    3840
gtggaaaagc tattggattt aagttggaca gagtcatgta aaccaacagc aactgaacca    3900
ctatttaaga aagtcagtcc atgggaaaca tctacttcta gctttttttcc tattttggct    3960 ccggccgttg gttcctatct taccccgact acccgcgctc acagtcctgc ttccttgtct    4020
tttgcctcat atcgtcaggt agctagtttc ggttcagctg ctcctcccag acagtttgat    4080
gcatctcaat tcagccaagg ccctgtgcct ggcacttgtg ctgactggat cccacagtcg    4140
gcgtcttgtc ccacaggacc tccccagaac ccaccttctg caccctattg tggcattgtt    4200
ttttcaggga gctcattaag ctctgcacag tctgctccac tgcaacatcc tggaggcttt    4260
actaccaggc cttctgctgg caccttccct gagctggatt ctccccagct tcatttctct    4320
cttcctacag accctgatcc catcagaggt tttgggtctt atcatccctc tgcttactct    4380
ccttttcatt ttcaaccttc cgcagcctct ttgactgcca accttaggct gccaatggcc    4440
tctgctttac ctgaggctct ttgcagtcag tcccggacta ccccagtaga tctctgtctt    4500
ctagaagaat cagtaggcag tctcgaagga agtcgatgtc ctgtctttgc ttttcaaagt    4560
tctgacacag aaagtgatga gctatcagaa gtacttcaag acagctgctt tttacaaata    4620
aagtgtgata caaagatga cagtatcccg tgctttctgg aattaaaaga agaggatgaa     4680
atagtgtgca cacaacactg gcaggatgct gtgccttgga cagaactcct cagtctacag    4740
acagaggatg gcttctggaa acttacacca gaactgggac ttatattaaa tcttaataca    4800
aatggtttgc acagctttct taaacaaaaa ggcattcaat ctctaggtgt aaaaggaaga    4860
gaatgtctcc tggacctaat tgccacaatg ctggtactac agtttattcg caccaggttg    4920
gaaaaagagg gaatagtgtt caaatcactg atgaaaatgg atgacccttc tatttccagg    4980
aatattccct gggcttttga ggcaataaag caagcaagtg aatgggtaag aagaactgaa    5040
ggacagtacc catctatctg cccacggctt gaactgggga acgactggga ctctgccacc    5100
aagcagttgc tgggactcca gcccataagc actgtgtccc ctcttcatag agtcctccat    5160
tacagtcaag gctaa                                                    5175
```

<210> SEQ ID NO 6
<211> LENGTH: 893
<212> TYPE: PRT
<213> ORGANISM: Homo sapiens

```
<400> SEQUENCE: 6

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Met
        35                  40                  45

Arg Met Val Thr Val Pro Pro Arg His Tyr Cys Thr Val Ala Asn Pro
    50                  55                  60

Val Ser Arg Asp Ala Gln Gly Leu Val Leu Phe Asp Val Thr Gly Gln
65                  70                  75                  80

Val Arg Leu Arg His Ala Asp Leu Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asp Gly Asp Lys Val Val Ala Gly Asp Glu Trp Leu
    130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                165                 170                 175

Arg Ala Arg Lys Glu Cys Trp Asp Arg Asp Gly Lys Glu Arg Val Thr
            180                 185                 190

Gly Glu Glu Trp Leu Val Thr Thr Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Arg Arg Asn Phe Arg Asp Phe Arg Gly
225                 230                 235                 240

Val Ser Arg Arg Thr Gly Glu Glu Trp Leu Val Thr Val Gln Asp Thr
                245                 250                 255

Glu Ala His Val Pro Asp Val His Glu Val Leu Gly Val Val Pro
            260                 265                 270

Ile Thr Thr Leu Gly Pro His Asn Tyr Cys Val Ile Leu Asp Pro Val
        275                 280                 285

Gly Pro Asp Gly Lys Asn Gln Leu Gly Gln Lys Arg Val Val Lys Gly
    290                 295                 300

Glu Lys Ser Phe Phe Leu Gln Pro Gly Glu Gln Leu Glu Gln Gly Ile
305                 310                 315                 320

Gln Asp Val Tyr Val Leu Ser Glu Gln Gln Gly Leu Leu Leu Arg Ala
                325                 330                 335

Leu Gln Pro Leu Glu Glu Gly Glu Asp Glu Glu Lys Val Ser His Gln
            340                 345                 350

Ala Gly Asp His Trp Leu Ile Arg Gly Pro Leu Glu Tyr Val Pro Ser
        355                 360                 365

Ala Lys Val Glu Val Val Glu Glu Arg Gln Ala Ile Pro Leu Asp Glu
    370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415
```

```
Lys Glu Leu Pro Pro Gly Val Glu Leu Leu Asn Lys Gly Gln Asp
            420                 425                 430

Pro Leu Ala Asp Arg Gly Glu Lys Asp Thr Ala Lys Ser Leu Gln Pro
        435                 440                 445

Leu Ala Pro Arg Asn Lys Thr Arg Val Val Ser Tyr Arg Val Pro His
    450                 455                 460

Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Thr Ala Val Phe Gly Phe Glu Thr
        595                 600                 605

Ser Glu Ala Lys Gly Pro Asp Gly Met Ala Leu Pro Arg Pro Arg Asp
610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
        675                 680                 685

Glu Arg Gln Lys Ile Leu Asp Gln Ser Glu Ala Glu Lys Ala Arg Lys
    690                 695                 700

Glu Leu Leu Glu Leu Glu Ala Leu Ser Met Ala Val Glu Ser Thr Gly
705                 710                 715                 720

Thr Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Gln Arg Val Gln Lys Val Arg Glu Leu
        755                 760                 765

Glu Leu Val Tyr Ala Arg Ala Gln Leu Glu Leu Glu Val Ser Lys Ala
    770                 775                 780

Gln Gln Leu Ala Glu Val Glu Val Lys Lys Phe Lys Gln Met Thr Glu
785                 790                 795                 800

Ala Ile Gly Pro Ser Thr Ile Arg Asp Leu Ala Val Ala Gly Pro Glu
                805                 810                 815

Met Gln Val Lys Leu Leu Gln Ser Leu Gly Leu Lys Ser Thr Leu Ile
            820                 825                 830

Thr Asp Gly Ser Thr Pro Ile Asn Leu Phe Asn Thr Ala Phe Gly Leu
        835                 840                 845
```

```
Leu Gly Met Gly Pro Glu Gly Gln Pro Leu Gly Arg Arg Val Ala Ser
    850                 855                 860
Gly Pro Ser Pro Gly Glu Gly Ile Ser Pro Gln Ser Ala Gln Ala Pro
865                 870                 875                 880
Gln Ala Pro Gly Asp Asn His Val Val Pro Val Leu Arg
                885                 890

<210> SEQ ID NO 7
<211> LENGTH: 2682
<212> TYPE: DNA
<213> ORGANISM: Homo sapiens

<400> SEQUENCE: 7
atggcaactg aagagttcat catccgcatc cccccatacc actatatcca tgtgctggac      60
cagaacagca acgtgtcccg tgtggaggtc gggccaaaga cctacatccg gcaggacaat     120
gagagggtac tgtttgcccc catgcgcatg gtgaccgtcc cccacgtca ctactgcaca      180 gtggccaacc ctgtgtctcg ggatgccag ggcttggtgc tgtttgatgt cacagggcaa      240
gttcggcttc gccacgctga cctcgagatc cggctggccc aggaccccctt ccccctgtac     300 ccaggggagt gctggaaaaa ggacatcaca ccccctgcagg tggttctgcc caacactgcc     360
ctccatctaa aggcgctgct tgattttgag gataaagatg agacaaggt ggtggcagga      420 gatgagtggc ttttcgaggg acctggcacg tacatccccc ggaaggaagt ggaggtcgtg     480
gagatcattc aggccaccat catcaggcag aaccaggctc tgcggctcag ggcccgcaag     540
gagtgctggg accgggacgg caaggagagg gtgacagggg aagaatggct ggtcaccaca     600 gtagggggcgt acctcccagc ggtgtttgag gaggttctgg atttggtgga cgccgtcatc     660
cttacgaaaa agacagccct gcacctccgg gctcggcgga acttccggga cttcaggggga    720 gtgtcccgcc gcactgggga ggagtggctg gtaacagtgc aggacacaga ggcccacgtg     780
ccagatgtcc acgaggaggt gctgggggtt gtgcccatca ccaccctggg ccccacaac      840 tactgcgtga ttctcgaccc tgtcggaccg gatggcaaga tcagctggg gcagaagcgc      900 gtggtcaagg gagagaagtc ttttttcctc cagccaggag agcagctgga caaggcatc      960 caggatgtgt atgtgctgtc ggagcagcag ggctgctgc tgagggcccct gcagcccctg    1020 gaggagggggg aggatgagga gaaggtctca caccaggctg ggaccactg gctcatccgc    1080 ggaccctgg agtatgtgcc atctgccaaa gtggaggtgg tggaggagcg ccaggccatc    1140
cctctagacg agaacgaggg catctatgtg caggatgtca agaccggaaa ggtgcgcgct    1200
gtgattggaa gcacctacat gctgacccag gacgaagtcc tgtgggagaa agagctgcct    1260 cccgggtgg aggagctgct gaacaagggg caggaccctc tggcagacag ggtgagaag    1320 gacacagcta agagcctcca gcccttggcg ccccggaaca agaccgtgt ggtcagctac    1380 cgcgtgcccc acaacgctgc ggtgcaggtg tacgactacc gagagaagcg agcccgcgtg    1440
gtcttcgggc ctgagctggt gtcgctgggt cctgaggagc agttcacagt gttgtccctc    1500
tcagctgggc ggcccaagcg tccccatgcc cgccgtgcgc tctgcctgct gctggggcct    1560
gacttcttca gacgtcat caccatcgaa acgcgggatc atgccaggct gcaactgcag    1620
ctggcctaca actggcactt tgaggtgaat gaccggaagg accccaaga gacggccaag    1680 ctcttttcag tgccagactt tgtaggtgat gcctgcaaag ccatcgcatc ccgggtgcgg    1740
ggggccgtgg cctctgtcac tttcgatgac ttccataaga actcagcccg catcattcgc    1800
actgctgtct ttggctttga gacctcggaa gcgaagggcc ccgatggcat ggccctgccc    1860
```

```
aggcccccggg accaggctgt cttcccccaa acgggctgg tggtcagcag tgtggacgtg    1920
cagtcagtgg agcctgtgga tcagaggacc cgggacgccc tgcaacgcag cgtccagctg    1980
gccatcgaga tcaccaccaa ctcccaggaa gcggcggcca agcatgaggc tcagagactg    2040
gagcaggaag cccgcggccg gcttgagcgg cagaagatcc tggaccagtc agaagccgag    2100
aaagctcgca aggaactttt ggagctggag gctctgagca tggccgtgga gagcaccggg    2160
actgccaagg cggaggccga gtcccgtgcg gaggcagccc ggattgaggg agaagggtcc    2220
gtgctgcagg ccaagctaaa agcacaggcc ttggccattg aaacggaggc tgagctccag    2280
agggtccaga aggtccgaga gctggaactg gtctatgccc gggcccagct ggagctggag    2340
gtgagcaagg ctcagcagct ggctgaggtg gaggtgaaga agttcaagca gatgacagag    2400
gccataggcc ccagcaccat cagggacctt gctgtggctg ggcctgagat gcaggtaaaa    2460
ctgctccagt ccctgggcct gaaatcaacc ctcatcaccg atggctccac tcccatcaac    2520
ctcttcaaca cagcctttgg gctgctgggg atggggcccg agggtcagcc cctgggcaga    2580
agggtggcca gtgggcccag ccctgggag gggatatccc cccagtctgc tcaggcccct    2640
caagctcctg gagacaacca cgtggtgcct gtactgcgct aa                       2682
```

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ala Gly Cys Gly Cys Pro Cys Gly Cys Gly Ala
1               5                   10

<210> SEQ ID NO 9
<211> LENGTH: 905
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Gly Cys Gly Cys Pro Cys Gly Cys Gly Ala Met Ala Thr Glu
1               5                   10                  15

Glu Phe Ile Ile Arg Ile Pro Pro Tyr His Tyr Ile His Val Leu Asp
                20                  25                  30

Gln Asn Ser Asn Val Ser Arg Val Glu Val Gly Pro Lys Thr Tyr Ile
            35                  40                  45

Arg Gln Asp Asn Glu Arg Val Leu Phe Ala Pro Met Arg Met Val Thr
        50                  55                  60

Val Pro Pro Arg His Tyr Cys Thr Val Ala Asn Pro Val Ser Arg Asp
65                  70                  75                  80

Ala Gln Gly Leu Val Leu Phe Asp Val Thr Gly Gln Val Arg Leu Arg
                85                  90                  95

His Ala Asp Leu Glu Ile Arg Leu Ala Gln Asp Pro Phe Pro Leu Tyr
                100                 105                 110

Pro Gly Glu Val Leu Glu Lys Asp Ile Thr Pro Leu Gln Val Val Leu
            115                 120                 125

Pro Asn Thr Ala Leu His Leu Lys Ala Leu Leu Asp Phe Glu Asp Lys
        130                 135                 140

```
Asp Gly Asp Lys Val Val Ala Gly Asp Glu Trp Leu Phe Glu Gly Pro
145                 150                 155                 160

Gly Thr Tyr Ile Pro Arg Lys Glu Val Glu Val Val Glu Ile Ile Gln
            165                 170                 175

Ala Thr Ile Ile Arg Gln Asn Gln Ala Leu Arg Leu Arg Ala Arg Lys
        180                 185                 190

Glu Cys Trp Asp Arg Asp Gly Lys Glu Arg Val Thr Gly Glu Glu Trp
    195                 200                 205

Leu Val Thr Thr Val Gly Ala Tyr Leu Pro Ala Val Phe Glu Glu Val
        210                 215                 220

Leu Asp Leu Val Asp Ala Val Ile Leu Thr Glu Lys Thr Ala Leu His
225                 230                 235                 240

Leu Arg Ala Arg Arg Asn Phe Arg Asp Phe Arg Gly Val Ser Arg Arg
            245                 250                 255

Thr Gly Glu Glu Trp Leu Val Thr Val Gln Asp Thr Glu Ala His Val
            260                 265                 270

Pro Asp Val His Glu Glu Val Leu Gly Val Val Pro Ile Thr Thr Leu
        275                 280                 285

Gly Pro His Asn Tyr Cys Val Ile Leu Asp Pro Val Gly Pro Asp Gly
290                 295                 300

Lys Asn Gln Leu Gly Gln Lys Arg Val Val Lys Gly Glu Lys Ser Phe
305                 310                 315                 320

Phe Leu Gln Pro Gly Glu Gln Leu Glu Gln Gly Ile Gln Asp Val Tyr
            325                 330                 335

Val Leu Ser Glu Gln Gln Gly Leu Leu Leu Arg Ala Leu Gln Pro Leu
            340                 345                 350

Glu Glu Gly Glu Asp Glu Glu Lys Val Ser His Gln Ala Gly Asp His
            355                 360                 365

Trp Leu Ile Arg Gly Pro Leu Glu Tyr Val Pro Ser Ala Lys Val Glu
        370                 375                 380

Val Val Glu Glu Arg Gln Ala Ile Pro Leu Asp Glu Asn Glu Gly Ile
385                 390                 395                 400

Tyr Val Gln Asp Val Lys Thr Gly Lys Val Arg Ala Val Ile Gly Ser
            405                 410                 415

Thr Tyr Met Leu Thr Gln Asp Glu Val Leu Trp Glu Lys Glu Leu Pro
            420                 425                 430

Pro Gly Val Glu Glu Leu Leu Asn Lys Gly Gln Asp Pro Leu Ala Asp
            435                 440                 445

Arg Gly Glu Lys Asp Thr Ala Lys Ser Leu Gln Pro Leu Ala Pro Arg
450                 455                 460

Asn Lys Thr Arg Val Val Ser Tyr Arg Val Pro His Asn Ala Ala Val
465                 470                 475                 480

Gln Val Tyr Asp Tyr Arg Glu Lys Arg Ala Arg Val Val Phe Gly Pro
            485                 490                 495

Glu Leu Val Ser Leu Gly Pro Glu Glu Gln Phe Thr Val Leu Ser Leu
            500                 505                 510

Ser Ala Gly Arg Pro Lys Arg Pro His Ala Arg Arg Ala Leu Cys Leu
            515                 520                 525

Leu Leu Gly Pro Asp Phe Phe Thr Asp Val Ile Thr Ile Glu Thr Ala
            530                 535                 540

Asp His Ala Arg Leu Gln Leu Gln Leu Ala Tyr Asn Trp His Phe Glu
545                 550                 555                 560
```

```
Val Asn Asp Arg Lys Asp Pro Gln Glu Thr Ala Lys Leu Phe Ser Val
            565                 570                 575

Pro Asp Phe Val Gly Asp Ala Cys Lys Ala Ile Ala Ser Arg Val Arg
        580                 585                 590

Gly Ala Val Ala Ser Val Thr Phe Asp Asp Phe His Lys Asn Ser Ala
    595                 600                 605

Arg Ile Ile Arg Thr Ala Val Phe Gly Phe Glu Thr Ser Glu Ala Lys
610                 615                 620

Gly Pro Asp Gly Met Ala Leu Pro Arg Pro Asp Gln Ala Val Phe
625                 630                 635                 640

Pro Gln Asn Gly Leu Val Val Ser Ser Val Asp Val Gln Ser Val Glu
            645                 650                 655

Pro Val Asp Gln Arg Thr Arg Asp Ala Leu Gln Arg Ser Val Gln Leu
        660                 665                 670

Ala Ile Glu Ile Thr Thr Asn Ser Gln Glu Ala Ala Lys His Glu
    675                 680                 685

Ala Gln Arg Leu Glu Gln Glu Ala Arg Gly Arg Leu Glu Arg Gln Lys
    690                 695                 700

Ile Leu Asp Gln Ser Glu Ala Glu Lys Ala Arg Lys Glu Leu Leu Glu
705                 710                 715                 720

Leu Glu Ala Leu Ser Met Ala Val Glu Ser Thr Gly Thr Ala Lys Ala
            725                 730                 735

Glu Ala Glu Ser Arg Ala Glu Ala Arg Ile Glu Gly Glu Gly Ser
        740                 745                 750

Val Leu Gln Ala Lys Leu Lys Ala Gln Ala Leu Ala Ile Glu Thr Glu
            755                 760                 765

Ala Glu Leu Gln Arg Val Gln Lys Val Arg Glu Leu Glu Leu Val Tyr
    770                 775                 780

Ala Arg Ala Gln Leu Glu Leu Glu Val Ser Lys Ala Gln Gln Leu Ala
785                 790                 795                 800

Glu Val Glu Val Lys Lys Phe Lys Gln Met Thr Glu Ala Ile Gly Pro
            805                 810                 815

Ser Thr Ile Arg Asp Leu Ala Val Ala Gly Pro Glu Met Gln Val Lys
        820                 825                 830

Leu Leu Gln Ser Leu Gly Leu Lys Ser Thr Leu Ile Thr Asp Gly Ser
    835                 840                 845

Thr Pro Ile Asn Leu Phe Asn Thr Ala Phe Gly Leu Leu Gly Met Gly
850                 855                 860

Pro Glu Gly Gln Pro Leu Gly Arg Arg Val Ala Ser Gly Pro Ser Pro
865                 870                 875                 880

Gly Glu Gly Ile Ser Pro Ser Ala Gln Ala Pro Gln Ala Pro Gly
            885                 890                 895

Asp Asn His Val Val Pro Val Leu Arg
            900                 905

<210> SEQ ID NO 10
<211> LENGTH: 2718
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 10

```
atggcaggct gcggttgtcc atgcggttgt ggcgccatgg caactgaaga gttcatcatc      60
cgcatccccc cataccacta tatccatgtg ctggaccaga acagcaacgt gtcccgtgtg     120
gaggtcgggc caaagaccta catccggcag gacaatgaga gggtactgtt tgcccccatg     180
cgcatggtga ccgtcccccc acgtcactac tgcacagtgg ccaaccctgt gtctcgggat     240
gcccagggct tggtgctgtt tgatgtcaca gggcaagttc ggcttcgcca cgctgacctc     300
gagatccggc tggcccagga ccccttcccc ctgtacccag gggaggtgct ggaaaaggac     360
atcacacccc tgcaggtggt tctgcccaac actgccctcc atctaaaggc gctgcttgat     420
tttgaggata aagatggaga caaggtggtg gcaggagatg agtggctttt cgagggacct     480
ggcacgtaca tcccccggaa ggaagtggag gtcgtggaga tcattcaggc caccatcatc     540
aggcagaacc aggctctgcg gctcagggcc cgcaaggagt gctgggaccg ggacggcaag     600
gagagggtga caggggaaga atggctggtc accacagtag gggcgtacct cccagcggtg     660
tttgaggagg ttctggattt ggtggacgcc gtcatcctta cggaaaagac agccctgcac     720
ctccgggctc ggcggaactt ccgggacttc aggggagtgt cccgccgcac tggggaggag     780
tggctggtaa cagtgcagga cacagaggcc cacgtgccag atgtccacga ggaggtgctg     840
ggggttgtgc ccatcaccac cctgggcccc cacaactact gcgtgattct cgaccctgtc     900
ggaccggatg caagaatca gctggggcag aagcgcgtgg tcaagggaga agtctctttt     960
ttcctccagc caggagagca gctggaacaa ggcatccagg atgtgtatgt gctgtcggag    1020
cagcaggggc tgctgctgag ggccctgcag cccctggagg aggggagga tgaggagaag    1080
gtctcacacc aggctgggga ccactggctc atccgcggac ccctggagta tgtgccatct    1140
gccaaagtgg aggtggtgga ggagcgccag gccatccctc tagacgagaa cgagggcatc    1200
tatgtgcagg atgtcaagac cggaaaggtg cgcgctgtga ttggaagcac ctacatgctg    1260
acccaggacc aagtcctgtg ggagaaagag ctgcctcccg gggtggagga gctgctgaac    1320
aaggggcagg accctctggc agacaggggt gagaaggaca cagctaagag cctccagccc    1380
ttggcgcccc ggaacaagac ccgtgtggtc agctaccgcg tgccccacaa cgctgcggtg    1440
caggtgtacg actaccgaga gaagcgagcc cgcgtggtct cgggcctga gctggtgtcg    1500
ctgggtcctg aggagcagtt cacagtgttg tccctctcag ctgggcggcc caagcgtccc    1560
catgcccgcc gtgcgctctg cctgctgctg gggcctgact tcttcacaga cgtcatcacc    1620
atcgaaacgg cggatcatgc caggctgcaa ctgcagctgg cctacaactg gcactttgag    1680
gtgaatgacc ggaaggaccc ccaagagacg gccaagctct tttcagtgcc agactttgta    1740
ggtgatgcct gcaaagccat cgcatcccgg gtgcgggggg ccgtggcctc tgtcactttc    1800
gatgacttcc ataagaactc agcccgcatc attcgcactg ctgtctttgg ctttgagacc    1860
tcggaagcga agggcccga tggcatggcc ctgcccaggc cccgggacca ggctgtcttc    1920
ccccaaaacg ggctggtggt cagcagtgtg gacgtgcagt cagtggagcc tgtggatcag    1980
aggacccggg acgccctgca acgcagcgtc cagctggcca tcgagatcac caccaactcc    2040
caggaagcgc cggccaagca tgaggctcag agactggagc aggaagcccg cggccggctt    2100
gagcggcaga agatcctgga ccagtcagaa gccgagaaag ctcgcaagga acttttggag    2160
ctggaggctc tgagcatggc cgtggagagc accgggactg ccaaggcgga ggccgagtcc    2220
cgtgcggagg cagcccggat tgaggagaa gggtccgtgc tgcaggccaa gctaaaagca    2280
caggccttgg ccattgaaac ggaggctgag ctccagaggg tccagaaggt ccgagagctg    2340
```

```
gaactggtct atgcccgggc ccagctggag ctggaggtga gcaaggctca gcagctggct    2400
gaggtggagg tgaagaagtt caagcagatg acagaggcca taggccccag caccatcagg    2460
gaccttgctg tggctgggcc tgagatgcag gtaaaactgc tccagtccct gggcctgaaa    2520
tcaaccctca tcaccgatgg ctccactccc atcaacctct tcaacacagc ctttgggctg    2580
ctggggatgg ggcccgaggg tcagcccctg gcagaaggg tggccagtgg gcccagccct    2640
ggggagggga tatccccca gtctgctcag gcccctcaag ctcctggaga caaccacgtg    2700
gtgcctgtac tgcgctaa                                                  2718

<210> SEQ ID NO 11
<211> LENGTH: 2627
<212> TYPE: PRT
<213> ORGANISM: Homo sapiens

<400> SEQUENCE: 11

Met Glu Lys Leu His Gly His Val Ser Ala His Pro Asp Ile Leu Ser
1               5                   10                  15

Leu Glu Asn Arg Cys Leu Ala Met Leu Pro Asp Leu Gln Pro Leu Glu
                20                  25                  30

Lys Leu His Gln His Val Ser Thr His Ser Asp Ile Leu Ser Leu Lys
            35                  40                  45

Asn Gln Cys Leu Ala Thr Leu Pro Asp Leu Lys Thr Met Glu Lys Pro
        50                  55                  60

His Gly Tyr Val Ser Ala His Pro Asp Ile Leu Ser Leu Glu Asn Gln
65                  70                  75                  80

Cys Leu Ala Thr Leu Ser Asp Leu Lys Thr Met Glu Lys Pro His Gly
                85                  90                  95

His Val Ser Ala His Pro Asp Ile Leu Ser Leu Glu Asn Arg Cys Leu
            100                 105                 110

Ala Thr Leu Pro Ser Leu Lys Ser Thr Val Ser Ala Ser Pro Leu Phe
        115                 120                 125

Gln Ser Leu Gln Ile Ser His Met Thr Gln Ala Asp Leu Tyr Arg Val
    130                 135                 140

Asn Asn Ser Asn Cys Leu Leu Ser Glu Pro Pro Ser Trp Arg Ala Gln
145                 150                 155                 160

His Phe Ser Lys Gly Leu Asp Leu Ser Thr Cys Pro Ile Ala Leu Lys
                165                 170                 175

Ser Ile Ser Ala Thr Glu Thr Ala Gln Glu Ala Thr Leu Gly Arg Trp
            180                 185                 190

Phe Asp Ser Glu Glu Lys Lys Gly Ala Glu Thr Gln Met Pro Ser Tyr
        195                 200                 205

Ser Leu Ser Leu Gly Glu Glu Glu Val Glu Asp Leu Ala Val Lys
    210                 215                 220

Leu Thr Ser Gly Asp Ser Glu Ser His Pro Glu Pro Thr Asp His Val
225                 230                 235                 240

Leu Gln Glu Lys Lys Met Ala Leu Leu Ser Leu Leu Cys Ser Thr Leu
                245                 250                 255

Val Ser Glu Val Asn Met Asn Asn Thr Ser Asp Pro Thr Leu Ala Ala
            260                 265                 270

Ile Phe Glu Ile Cys Arg Glu Leu Ala Leu Leu Glu Pro Glu Phe Ile
        275                 280                 285

Leu Lys Ala Ser Leu Tyr Ala Arg Gln Gln Leu Asn Val Arg Asn Val
    290                 295                 300
```

```
Ala Asn Asn Ile Leu Ala Ile Ala Ala Phe Leu Pro Ala Cys Arg Pro
305                 310                 315                 320

His Leu Arg Arg Tyr Phe Cys Ala Ile Val Gln Leu Pro Ser Asp Trp
            325                 330                 335

Ile Gln Val Ala Glu Leu Tyr Gln Ser Leu Ala Glu Gly Asp Lys Asn
        340                 345                 350

Lys Leu Val Pro Leu Pro Ala Cys Leu Arg Thr Ala Met Thr Asp Lys
            355                 360                 365

Phe Ala Gln Phe Asp Glu Tyr Gln Leu Ala Lys Tyr Asn Pro Arg Lys
370                 375                 380

His Arg Ala Lys Arg His Pro Arg Arg Pro Arg Ser Pro Gly Met
385                 390                 395                 400

Glu Pro Pro Phe Ser His Arg Cys Phe Pro Arg Tyr Ile Gly Phe Leu
            405                 410                 415

Arg Glu Glu Gln Arg Lys Phe Glu Lys Ala Gly Asp Thr Val Ser Glu
        420                 425                 430

Lys Lys Asn Pro Pro Arg Phe Thr Leu Lys Lys Leu Val Gln Arg Leu
            435                 440                 445

His Ile His Lys Pro Ala Gln His Val Gln Ala Leu Leu Gly Tyr Arg
450                 455                 460

Tyr Pro Ser Asn Leu Gln Leu Phe Ser Arg Ser Arg Leu Pro Gly Pro
465                 470                 475                 480

Trp Asp Ser Ser Arg Ala Gly Lys Arg Met Lys Leu Ser Arg Pro Glu
            485                 490                 495

Thr Trp Glu Arg Glu Leu Ser Leu Arg Gly Asn Lys Ala Ser Val Trp
        500                 505                 510

Glu Glu Leu Ile Glu Asn Gly Lys Leu Pro Phe Met Ala Met Leu Arg
            515                 520                 525

Asn Leu Cys Asn Leu Leu Arg Val Gly Ile Ser Ser Arg His His Glu
530                 535                 540

Leu Ile Leu Gln Arg Leu Gln His Gly Lys Ser Val Ile His Ser Arg
545                 550                 555                 560

Gln Phe Pro Phe Arg Phe Leu Asn Ala His Asp Ala Ile Asp Ala Leu
            565                 570                 575

Glu Ala Gln Leu Arg Asn Gln Ala Leu Pro Phe Pro Ser Asn Ile Thr
        580                 585                 590

Leu Met Arg Arg Ile Leu Thr Arg Asn Glu Lys Asn Arg Pro Arg Arg
            595                 600                 605

Arg Phe Leu Cys His Leu Ser Arg Gln Gln Leu Arg Met Ala Met Arg
610                 615                 620

Ile Pro Val Leu Tyr Glu Gln Leu Lys Arg Glu Lys Leu Arg Val His
625                 630                 635                 640

Lys Ala Arg Gln Trp Lys Tyr Asp Gly Glu Met Leu Asn Arg Tyr Arg
            645                 650                 655

Gln Ala Leu Glu Thr Ala Val Asn Leu Ser Val Lys His Ser Leu Pro
        660                 665                 670

Leu Leu Pro Gly Arg Thr Val Leu Val Tyr Leu Thr Asp Ala Asn Ala
            675                 680                 685

Asp Arg Leu Cys Pro Lys Ser Asn Pro Gln Gly Pro Pro Leu Asn Tyr
690                 695                 700

Ala Leu Leu Leu Ile Gly Met Met Ile Thr Arg Ala Glu Gln Val Asp
705                 710                 715                 720
```

-continued

Val Val Leu Cys Gly Gly Asp Thr Leu Lys Thr Ala Val Leu Lys Ala
              725                 730                 735

Glu Glu Gly Ile Leu Lys Thr Ala Ile Lys Leu Gln Ala Gln Val Gln
              740                 745                 750

Glu Phe Asp Glu Asn Asp Gly Trp Ser Leu Asn Thr Phe Gly Lys Tyr
              755                 760                 765

Leu Leu Ser Leu Ala Gly Gln Arg Val Pro Val Asp Arg Val Ile Leu
      770                 775                 780

Leu Gly Gln Ser Met Asp Gly Met Ile Asn Val Ala Lys Gln Leu
785                 790                 795                 800

Tyr Trp Gln Arg Val Asn Ser Lys Cys Leu Phe Val Gly Ile Leu Leu
                  805                 810                 815

Arg Arg Val Gln Tyr Leu Ser Thr Asp Leu Asn Pro Asn Asp Val Thr
                  820                 825                 830

Leu Ser Gly Cys Thr Asp Ala Ile Leu Lys Phe Ile Ala Glu His Gly
          835                 840                 845

Ala Ser His Leu Leu Glu His Val Gly Gln Met Asp Lys Ile Phe Lys
      850                 855                 860

Ile Pro Pro Pro Pro Gly Lys Thr Gly Val Gln Ser Leu Arg Pro Leu
865                 870                 875                 880

Glu Glu Asp Thr Pro Ser Pro Leu Ala Pro Val Ser Gln Gln Gly Trp
                  885                 890                 895

Arg Ser Ile Arg Leu Phe Ile Ser Ser Thr Phe Arg Asp Met His Gly
                  900                 905                 910

Glu Arg Asp Leu Leu Leu Arg Ser Val Leu Pro Ala Leu Gln Ala Arg
              915                 920                 925

Ala Ala Pro His Arg Ile Ser Leu His Gly Ile Asp Leu Arg Trp Gly
      930                 935                 940

Val Thr Glu Glu Glu Thr Arg Arg Asn Arg Gln Leu Glu Val Cys Leu
945                 950                 955                 960

Gly Glu Val Glu Asn Ala Gln Leu Phe Val Gly Ile Leu Gly Ser Arg
                  965                 970                 975

Tyr Gly Tyr Ile Pro Pro Ser Tyr Asn Leu Pro Asp His Pro His Phe
              980                 985                 990

His Trp Ala Gln Gln Tyr Pro Ser Gly Arg Ser Val Thr Glu Met Glu
      995                 1000                1005

Val Met Gln Phe Leu Asn Arg Asn Gln Arg Leu Gln Pro Ser Ala
      1010                1015                1020

Gln Ala Leu Ile Tyr Phe Arg Asp Ser Ser Phe Leu Ser Ser Val
      1025                1030                1035

Pro Asp Ala Trp Lys Ser Asp Phe Val Ser Glu Ser Glu Glu Ala
      1040                1045                1050

Ala Cys Arg Ile Ser Glu Leu Lys Ser Tyr Leu Ser Arg Gln Lys
      1055                1060                1065

Gly Ile Thr Cys Arg Arg Tyr Pro Cys Glu Trp Gly Gly Val Ala
      1070                1075                1080

Ala Gly Arg Pro Tyr Val Gly Gly Leu Glu Glu Phe Gly Gln Leu
      1085                1090                1095

Val Leu Gln Asp Val Trp Asn Met Ile Gln Lys Leu Tyr Leu Gln
      1100                1105                1110

Pro Gly Ala Leu Leu Glu Gln Pro Val Ser Ile Pro Asp Asp Asp
      1115                1120                1125

```
Leu Val Gln Ala Thr Phe Gln Gln Leu Gln Lys Pro Pro Ser Pro
1130                1135                1140

Ala Arg Pro Arg Leu Leu Gln Asp Thr Val Gln Gln Leu Met Leu
1145                1150                1155

Pro His Gly Arg Leu Ser Leu Val Thr Gly Gln Ser Gly Gln Gly
1160                1165                1170

Lys Thr Ala Phe Leu Ala Ser Leu Val Ser Ala Leu Gln Ala Pro
1175                1180                1185

Asp Gly Ala Lys Val Ala Pro Leu Val Phe Phe His Phe Ser Gly
1190                1195                1200

Ala Arg Pro Asp Gln Gly Leu Ala Leu Thr Leu Leu Arg Arg Leu
1205                1210                1215

Cys Thr Tyr Leu Arg Gly Gln Leu Lys Glu Pro Gly Ala Leu Pro
1220                1225                1230

Ser Thr Tyr Arg Ser Leu Val Trp Glu Leu Gln Gln Arg Leu Leu
1235                1240                1245

Pro Lys Ser Ala Glu Ser Leu His Pro Gly Gln Thr Gln Val Leu
1250                1255                1260

Ile Ile Asp Gly Ala Asp Arg Leu Val Asp Gln Asn Gly Gln Leu
1265                1270                1275

Ile Ser Asp Trp Ile Pro Lys Lys Leu Pro Arg Cys Val His Leu
1280                1285                1290

Val Leu Ser Val Ser Ser Asp Ala Gly Leu Gly Glu Thr Leu Glu
1295                1300                1305

Gln Ser Gln Gly Ala His Val Leu Ala Leu Gly Pro Leu Glu Ala
1310                1315                1320

Ser Ala Arg Ala Arg Leu Val Arg Glu Glu Leu Ala Leu Tyr Gly
1325                1330                1335

Lys Arg Leu Glu Glu Ser Pro Phe Asn Asn Gln Met Arg Leu Leu
1340                1345                1350

Leu Val Lys Arg Glu Ser Gly Arg Pro Leu Tyr Leu Arg Leu Val
1355                1360                1365

Thr Asp His Leu Arg Leu Phe Thr Leu Tyr Glu Gln Val Ser Glu
1370                1375                1380

Arg Leu Arg Thr Leu Pro Ala Thr Val Pro Leu Leu Leu Gln His
1385                1390                1395

Ile Leu Ser Thr Leu Glu Lys Glu His Gly Pro Asp Val Leu Pro
1400                1405                1410

Gln Ala Leu Thr Ala Leu Glu Val Thr Arg Ser Gly Leu Thr Val
1415                1420                1425

Asp Gln Leu His Gly Val Leu Ser Val Trp Arg Thr Leu Pro Lys
1430                1435                1440

Gly Thr Lys Ser Trp Glu Glu Ala Val Ala Ala Gly Asn Ser Gly
1445                1450                1455

Asp Pro Tyr Pro Met Gly Pro Phe Ala Cys Leu Val Gln Ser Leu
1460                1465                1470

Arg Ser Leu Leu Gly Glu Gly Pro Leu Glu Arg Pro Gly Ala Arg
1475                1480                1485

Leu Cys Leu Pro Asp Gly Pro Leu Arg Thr Ala Ala Lys Arg Cys
1490                1495                1500

Tyr Gly Lys Arg Pro Gly Leu Glu Asp Thr Ala His Ile Leu Ile
1505                1510                1515
```

```
Ala Ala Gln Leu Trp Lys Thr Cys Asp Ala Asp Ala Ser Gly Thr
    1520                1525                1530

Phe Arg Ser Cys Pro Pro Glu Ala Leu Gly Asp Leu Pro Tyr His
    1535                1540                1545

Leu Leu Gln Ser Gly Asn Arg Gly Leu Leu Ser Lys Phe Leu Thr
    1550                1555                1560

Asn Leu His Val Val Ala Ala His Leu Glu Leu Gly Leu Val Ser
    1565                1570                1575

Arg Leu Leu Glu Ala His Ala Leu Tyr Ala Ser Ser Val Pro Lys
    1580                1585                1590

Glu Glu Gln Lys Leu Pro Glu Ala Asp Val Ala Val Phe Arg Thr
    1595                1600                1605

Phe Leu Arg Gln Gln Ala Ser Ile Leu Ser Gln Tyr Pro Arg Leu
    1610                1615                1620

Leu Pro Gln Gln Ala Ala Asn Gln Pro Leu Asp Ser Pro Leu Cys
    1625                1630                1635

His Gln Ala Ser Leu Leu Ser Arg Arg Trp His Leu Gln His Thr
    1640                1645                1650

Leu Arg Trp Leu Asn Lys Pro Arg Thr Met Lys Asn Gln Gln Ser
    1655                1660                1665

Ser Ser Leu Ser Leu Ala Val Ser Ser Ser Pro Thr Ala Val Ala
    1670                1675                1680

Phe Ser Thr Asn Gly Gln Arg Ala Ala Val Gly Thr Ala Asn Gly
    1685                1690                1695

Thr Val Tyr Leu Leu Asp Leu Arg Thr Trp Gln Glu Glu Lys Ser
    1700                1705                1710

Val Val Ser Gly Cys Asp Gly Ile Ser Ala Cys Leu Phe Leu Ser
    1715                1720                1725

Asp Asp Thr Leu Phe Leu Thr Ala Phe Asp Gly Leu Leu Glu Leu
    1730                1735                1740

Trp Asp Leu Gln His Gly Cys Arg Val Leu Gln Thr Lys Ala His
    1745                1750                1755

Gln Tyr Gln Ile Thr Gly Cys Cys Leu Ser Pro Asp Cys Arg Leu
    1760                1765                1770

Leu Ala Thr Val Cys Leu Gly Gly Cys Leu Lys Leu Trp Asp Thr
    1775                1780                1785

Val Arg Gly Gln Leu Ala Phe Gln His Thr Tyr Pro Lys Ser Leu
    1790                1795                1800

Asn Cys Val Ala Phe His Pro Glu Gly Gln Val Ile Ala Thr Gly
    1805                1810                1815

Ser Trp Ala Gly Ser Ile Ser Phe Phe Gln Val Asp Gly Leu Lys
    1820                1825                1830

Val Thr Lys Asp Leu Gly Ala Pro Gly Ala Ser Ile Arg Thr Leu
    1835                1840                1845

Ala Phe Asn Val Pro Gly Gly Val Val Ala Val Gly Arg Leu Asp
    1850                1855                1860

Ser Met Val Glu Leu Trp Ala Trp Arg Glu Gly Ala Arg Leu Ala
    1865                1870                1875

Ala Phe Pro Ala His His Gly Phe Val Ala Ala Leu Phe Leu
    1880                1885                1890

His Ala Gly Cys Gln Leu Leu Thr Ala Gly Glu Asp Gly Lys Val
    1895                1900                1905
```

```
Gln Val Trp Ser Gly Ser Leu Gly Arg Pro Arg Gly His Leu Gly
1910                1915                1920

Ser Leu Ser Leu Ser Pro Ala Leu Ser Val Ala Leu Ser Pro Asp
    1925                1930                1935

Gly Asp Arg Val Ala Val Gly Tyr Arg Ala Asp Gly Ile Arg Ile
1940                1945                1950

Tyr Lys Ile Ser Ser Gly Ser Gln Gly Ala Gln Gly Gln Ala Leu
    1955                1960                1965

Asp Val Ala Val Ser Ala Leu Ala Trp Leu Ser Pro Lys Val Leu
1970                1975                1980

Val Ser Gly Ala Glu Asp Gly Ser Leu Gln Gly Trp Ala Leu Lys
    1985                1990                1995

Glu Cys Ser Leu Gln Ser Leu Trp Leu Leu Ser Arg Phe Gln Lys
2000                2005                2010

Pro Val Leu Gly Leu Ala Thr Ser Gln Glu Leu Leu Ala Ser Ala
    2015                2020                2025

Ser Glu Asp Phe Thr Val Gln Leu Trp Pro Arg Gln Leu Leu Thr
2030                2035                2040

Arg Pro His Lys Ala Glu Asp Phe Pro Cys Gly Thr Glu Leu Arg
    2045                2050                2055

Gly His Glu Gly Pro Val Ser Cys Cys Ser Phe Ser Thr Asp Gly
2060                2065                2070

Gly Ser Leu Ala Thr Gly Gly Arg Asp Arg Ser Leu Leu Cys Trp
    2075                2080                2085

Asp Val Arg Thr Pro Lys Thr Pro Val Leu Ile His Ser Phe Pro
2090                2095                2100

Ala Cys His Arg Asp Trp Val Thr Gly Cys Ala Trp Thr Lys Asp
    2105                2110                2115

Asn Leu Leu Ile Ser Cys Ser Ser Asp Gly Ser Val Gly Leu Trp
2120                2125                2130

Asp Pro Glu Ser Gly Gln Arg Leu Gly Gln Phe Leu Gly His Gln
    2135                2140                2145

Ser Ala Val Ser Ala Val Ala Val Glu Glu His Val Val Ser
2150                2155                2160

Val Ser Arg Asp Gly Thr Leu Lys Val Trp Asp His Gln Gly Val
    2165                2170                2175

Glu Leu Thr Ser Ile Pro Ala His Ser Gly Pro Ile Ser His Cys
2180                2185                2190

Ala Ala Ala Met Glu Pro Arg Ala Ala Gly Gln Pro Gly Ser Glu
    2195                2200                2205

Leu Leu Val Val Thr Val Gly Leu Asp Gly Ala Thr Arg Leu Trp
2210                2215                2220

His Pro Leu Leu Val Cys Gln Thr His Thr Leu Leu Gly His Ser
    2225                2230                2235

Gly Pro Val Arg Ala Ala Val Ser Glu Thr Ser Gly Leu Met
2240                2245                2250

Leu Thr Ala Ser Glu Asp Gly Ser Val Arg Leu Trp Gln Val Pro
    2255                2260                2265

Lys Glu Ala Asp Asp Thr Cys Ile Pro Arg Ser Ser Ala Ala Val
2270                2275                2280

Thr Ala Val Ala Trp Ala Pro Asp Gly Ser Met Ala Val Ser Gly
    2285                2290                2295
```

| Asn | Gln | Ala | Gly | Glu | Leu | Ile | Leu | Trp | Gln | Glu | Ala | Lys | Ala | Val |
| 2300 | | | | | 2305 | | | | | 2310 | | | | |

| Ala | Thr | Ala | Gln | Ala | Pro | Gly | His | Ile | Gly | Ala | Leu | Ile | Trp | Ser |
| 2315 | | | | | 2320 | | | | | 2325 | | | | |

| Ser | Ala | His | Thr | Phe | Phe | Val | Leu | Ser | Ala | Asp | Glu | Lys | Ile | Ser |
| 2330 | | | | | 2335 | | | | | 2340 | | | | |

| Glu | Trp | Gln | Val | Lys | Leu | Arg | Lys | Gly | Ser | Ala | Pro | Gly | Asn | Leu |
| 2345 | | | | | 2350 | | | | | 2355 | | | | |

| Ser | Leu | His | Leu | Asn | Arg | Ile | Leu | Gln | Glu | Asp | Leu | Gly | Val | Leu |
| 2360 | | | | | 2365 | | | | | 2370 | | | | |

| Thr | Ser | Leu | Asp | Trp | Ala | Pro | Asp | Gly | His | Phe | Leu | Ile | Leu | Ala |
| 2375 | | | | | 2380 | | | | | 2385 | | | | |

| Lys | Ala | Asp | Leu | Lys | Leu | Leu | Cys | Met | Lys | Pro | Gly | Asp | Ala | Pro |
| 2390 | | | | | 2395 | | | | | 2400 | | | | |

| Ser | Glu | Ile | Trp | Ser | Ser | Tyr | Thr | Glu | Asn | Pro | Met | Ile | Leu | Ser |
| 2405 | | | | | 2410 | | | | | 2415 | | | | |

| Thr | His | Lys | Glu | Tyr | Gly | Ile | Phe | Val | Leu | Gln | Pro | Lys | Asp | Pro |
| 2420 | | | | | 2425 | | | | | 2430 | | | | |

| Gly | Val | Leu | Ser | Phe | Leu | Arg | Gln | Lys | Glu | Ser | Gly | Glu | Phe | Glu |
| 2435 | | | | | 2440 | | | | | 2445 | | | | |

| Glu | Arg | Leu | Asn | Phe | Asp | Ile | Asn | Leu | Glu | Asn | Pro | Ser | Arg | Thr |
| 2450 | | | | | 2455 | | | | | 2460 | | | | |

| Leu | Ile | Ser | Ile | Thr | Gln | Ala | Lys | Pro | Glu | Ser | Glu | Ser | Ser | Phe |
| 2465 | | | | | 2470 | | | | | 2475 | | | | |

| Leu | Cys | Ala | Ser | Ser | Asp | Gly | Ile | Leu | Trp | Asn | Leu | Ala | Lys | Cys |
| 2480 | | | | | 2485 | | | | | 2490 | | | | |

| Ser | Pro | Glu | Gly | Glu | Trp | Thr | Thr | Gly | Asn | Met | Trp | Gln | Lys | Lys |
| 2495 | | | | | 2500 | | | | | 2505 | | | | |

| Ala | Asn | Thr | Pro | Glu | Thr | Gln | Thr | Pro | Gly | Thr | Asp | Pro | Ser | Thr |
| 2510 | | | | | 2515 | | | | | 2520 | | | | |

| Cys | Arg | Glu | Ser | Asp | Ala | Ser | Met | Asp | Ser | Asp | Ala | Ser | Met | Asp |
| 2525 | | | | | 2530 | | | | | 2535 | | | | |

| Ser | Glu | Pro | Thr | Pro | His | Leu | Lys | Thr | Arg | Gln | Arg | Arg | Lys | Ile |
| 2540 | | | | | 2545 | | | | | 2550 | | | | |

| His | Ser | Gly | Ser | Val | Thr | Ala | Leu | His | Val | Leu | Pro | Glu | Leu | Leu |
| 2555 | | | | | 2560 | | | | | 2565 | | | | |

| Val | Thr | Ala | Ser | Lys | Asp | Arg | Asp | Val | Lys | Leu | Trp | Glu | Arg | Pro |
| 2570 | | | | | 2575 | | | | | 2580 | | | | |

| Ser | Met | Gln | Leu | Leu | Gly | Leu | Phe | Arg | Cys | Glu | Gly | Ser | Val | Ser |
| 2585 | | | | | 2590 | | | | | 2595 | | | | |

| Cys | Leu | Glu | Pro | Trp | Leu | Gly | Ala | Asn | Ser | Thr | Leu | Gln | Leu | Ala |
| 2600 | | | | | 2605 | | | | | 2610 | | | | |

| Val | Gly | Asp | Val | Gln | Gly | Asn | Val | Tyr | Phe | Leu | Asn | Trp | Glu | |
| 2615 | | | | | 2620 | | | | | 2625 | | | | |

<210> SEQ ID NO 12
<211> LENGTH: 7884
<212> TYPE: DNA
<213> ORGANISM: Homo sapiens

<400> SEQUENCE: 12

```
atggaaaaac tccatgggca tgtgtctgcc catccagaca tcctctcctt ggagaaccgg      60
tgcctggcta tgctccctga cttacagccc ttggagaaac tacatcagca tgtatctacc     120
cactcagata tcctctcctt gaagaaccag tgcctagcca cgcttcctga cctgaagacc     180
```

```
atggaaaaac cacatggata tgtgtctgcc cacccagaca tcctctcctt ggagaaccag    240
tgcctggcca cactttctga cctgaagacc atggagaaac cacatggaca tgtttctgcc    300
cacccagaca tcctctcctt ggagaaccgg tgcctggcca ccctccctag tctaaagagc    360
actgtgtctg ccagccccttgttccagagt ctacagatat ctcacatgac gcaagctgat     420
ttgtaccgtg tgaacaacag caattgcctg ctctctgagc ctccaagttg gagggctcag    480
catttctcta agggactaga cctttcaacc tgcccctatag ccctgaaatc catctctgcc    540
acagagacag ctcaggaagc aactttgggt cgttggtttg attcagaaga gaagaagggg    600
gcagagaccc aaatgccttc ttatagtctg agcttgggag aggaggagga ggtgaggat     660 ctggccgtga agctcacctc tggagactct gaatctcatc cagagcctac tgaccatgtc    720
cttcaggaaa agaagatggc tctactgagc ttgctgtgct ctactctggt ctcagaagta    780
aacatgaaca atacatctga ccccaccctg gctgccattt ttgaaatctg tcgtgaactt    840
gccctcctgg agcctgagtt tatcctcaag gcatctttgt atgccaggca gcagctgaac    900
gtccggaatg tggccaataa catcttggcc attgctgctt tcttgccggc gtgtcgcccc    960
cacctgcgac gatatttctg tgccattgtc cagctgcctt ctgactggat ccaggtggct   1020
gagctttacc agagcctggc tgagggagat aagaataagc tggtgcccct gccgcctgt    1080 ctccgtactg ccatgacgga caaatttgcc cagtttgacg agtaccagct ggctaagtac   1140
aaccctcgga agcaccgggc caagagacac ccccgccggc caccccgctc tccagggatg   1200
gagcctccat tttctcacag atgttttcca aggtacatag ggtttctcag agaagagcag   1260
agaaagtttg agaaggccgg tgatacagtg tcagagaaaa agaatcctcc aaggttcacc   1320
ctgaagaagc tggttcagcg actgcacatc cacaagcctg cccagcacgt tcaagccctg   1380
ctgggttaca gataccccc caacctacag ctcttttctc gaagtcgcct tcctgggcct    1440
tgggattcta gcagagctgg gaagaggatg aagctgtcta ggccagagac ctgggagcgg   1500
gagctgagcc tacgggggaa caaagcgtcg gtctgggagg aactcattga aaatgggaag   1560
cttcccttca tggccatgct tcggaacctg tgcaacctgc tgcgggttgg aatcagttcc   1620
cgccaccatg agctcattct ccagagactc cagcatggga agtcggtgat ccacagtcgg   1680
cagtttccat tcagatttct taacgcccat gatgccattg atgccctcga ggctcaactc   1740
agaaatcaag cattgccctt ccttcgaat ataacactga tgaggcggat actaactaga    1800
aatgaaaaga accgtcccag gcggaggttt ctttgccacc taagccgtca gcagcttcgt   1860
atggcaatga ggatacctgt gttgtatgag cagctcaaga gggagaagct gagagtacac   1920
aaggccagac agtggaaata tgatggtgag atgctgaaca ggtaccgaca ggccctagag   1980
acagctgtga acctctctgt gaagcacagc ctgcccctgc tgccaggccg cactgtcttg   2040
gtctatctga cagatgctaa tgcagacagg ctctgtccaa agagcaaccc acaagggccc   2100
ccgctgaact atgcactgct gttgattggg atgatgatca cgagggcgga gcaggtggac   2160
gtcgtgctgt gtggaggtga cactctgaag actgcagtgc ttaaggcaga agaaggcatc   2220
ctgaagactg ccatcaagct ccaggctcaa gtccaggagt ttgatgaaaa tgatggatgg   2280
tccctgaata cttttgggaa ataccctgctg tctctggctg gccaaagggt tcctgtggac   2340
agggtcatcc tccttggcca agcatggat gatggaatga taaatgtggc caaacagctt   2400
tactggcagc gtgtgaattc caagtgcctc tttgttggta tcctcctaag aagggtacaa   2460
tacctgtcaa cagatttgaa tcccaatgat gtgacactct caggctgtac tgatgcgata   2520
ctgaagttca ttgcagagca tgggcctcc catcttctgg aacatgtggg ccaaatggac   2580
```

```
aaaatattca agattccacc accccccagga aagacagggg tccagtctct ccggccactg    2640
gaagaggaca ctccaagccc cttggctcct gtttcccagc aaggatggcg cagcatccgg    2700
cttttcattt catccacttt ccgagacatg cacggggagc gggacctgct gctgaggtct    2760
gtgctgccag cactgcaggc ccgagcggcc cctcaccgta tcagccttca cggaatcgac    2820
ctccgctggg gcgtcactga ggaggagacc cgtaggaaca gacaactgga agtgtgcctt    2880
ggggaggtgg agaacgcaca gctgtttgtg gggattctgg gctcccgtta tggatacatt    2940
cccccccagct acaaccttcc tgaccatcca cacttccact gggcccagca gtacccttca    3000
gggcgtctg tgacagagat ggaggtgatg cagttcctga accggaacca acgtctgcag     3060
ccctctgccc aagctctcat ctacttccgg gattccagct cctcagctc tgtgccagat     3120
gcctggaaat ctgactttgt ttctgagtct gaagaggccg catgtcggat ctcagaactg    3180
aagagctacc taagcagaca gaaagggata acctgccgca gataccctg tgagtggggg     3240
ggtgtggcag ctggccggcc ctatgttggc gggctggagg agtttgggca gttggttctg    3300
caggatgtat ggaatatgat ccagaagctc tacctgcagc ctggggccct gctggagcag    3360
ccagtgtcca tcccagacga tgacttggtc caggccacct tccagcagct gcagaagcca    3420
ccgagtcctg cccggccacg ccttcttcag gacacagtgc aacagctgat gctgccccac    3480
ggaaggctga gcctggtgac ggggcagtca ggacagggca agacagcctt cctggcatct    3540
cttgtgtcag ccctgcaggc tcctgatggg gccaaggtgg caccattagt cttcttccac    3600
ttttctgggg ctcgtcctga ccagggtctt gccctcactc tgctcagacg cctctgtacc    3660
tatctgcgtg ccaactaaa agagccaggt gccctccca gcacctaccg aagcctggtg      3720
tgggagctgc agcagaggct gctgcccaag tctgctgagt ccctgcatcc tggccagacc    3780
caggtcctga tcatcgatgg ggctgatagg ttagtggacc agaatgggca gctgatttca    3840
gactggatcc caaagaagct tccccggtgt gtacacctgg tgctgagtgt gtctagtgat    3900
gcaggcctag gggagaccct tgagcagagc cagggtgccc acgtgctggc cttggggcct    3960
ctggaggcct ctgctcgggc ccggctggtg agagaggagc tggccctgta cgggaagcgg    4020
ctggaggagt caccatttaa caaccagatg cgactgctgc tggtgaagcg ggaatcaggc    4080
cggccgctct acctgcgctt ggtcaccgat cacctgaggc tcttcacgct gtatgagcag    4140
gtgtctgaga gactccggac cctgcctgcc actgtccccc tgctgctgca gcacatcctg    4200
agcacactgg agaaggagca cgggcctgat gtccttcccc aggccttgac tgccctagaa    4260
gtcacacgga gtggttttga ctgtggaccag ctgcacggag tgctgagtgt gtggcggaca    4320
ctaccgaagg ggactaagag ctgggaagaa gcagtggctg ctggtaacag tggagacccc    4380
tacccccatgg gcccgtttgc ctgcctcgtc cagagtctgc gcagtttgct aggggagggc    4440
cctctggagc gccctggtgc ccggctgtgc ctccctgatg ggcccctgag aacagcagct    4500
aaacgttgct atgggaagag gccagggcta gaggacacgg cacacatcct cattgcagct    4560
cagctctgga agacatgtga cgctgatgcc tcaggcacct tccgaagttg ccctcctgag    4620
gctctgggag acctgcctta ccacctgctc cagagcggga accgtggact tctttcgaag    4680
ttccttacca acctccatgt ggtggctgca cacttggaat tgggtctggt ctctcggctc    4740
ttggaggccc atgccctcta tgcttcttca gtccccaaag aggaacaaaa gctcccgag    4800
gctgacgttg cagtgtttcg caccttcctg aggcagcagg cttcaatcct cagccagtac    4860
ccccggctcc tgccccagca ggcagccaac cagcccctgg actcacctct ttgccaccaa    4920
gcctcgctgc tctcccggag atggcacctc caacacacac tacgatggct taataaaccc    4980
```

```
cggaccatga aaaatcagca aagctccagc ctgtctctgg cagtttcctc atcccctact    5040
gctgtggcct tctccaccaa tgggcaaaga gcagctgtgg gcactgccaa tgggacagtt    5100
tacctgttgg acctgagaac ttggcaggag gagaagtctg tggtgagtgg ctgtgatgga    5160
atctctgctt gtttgttcct ctccgatgat acactctttc ttactgcctt cgacgggctc    5220
ctggagctct gggacctgca gcatggttgt cgggtgctgc agactaaggc tcaccagtac    5280
caaatcactg gctgctgcct gagcccagac tgccggctgc tagccaccgt gtgcttggga    5340
ggatgcctaa agctgtggga cacagtccgt gggcagctgg ccttccagca cacctacccc    5400
aagtccctga actgtgttgc cttccaccca gaggggcagg taatagccac aggcagctgg    5460
gctggcagca tcagcttctt ccaggtggat gggctcaaag tcaccaagga cctggggca    5520 cccggagcct ctatccgtac cttggccttc aatgtgcctg ggggggttgt ggctgtgggc    5580
cggctggaca gtatggtgga gctgtgggcc tggcgagaag gggcacggct ggctgccttc    5640
cctgcccacc atggctttgt tgctgctgcg ctttcctgc atgcgggttg ccagttactg    5700
acggctggag aggatggcaa ggttcaggtg tggtcagggt ctctgggtcg gccccgtggg    5760
cacctgggtt cccttctct ctctcctgcc ctctctgtgg cactcagccc agatggtgat    5820
cgggtggctg ttggatatcg agcggatggc attaggatct acaaaatctc ttcaggttcc    5880 caggggctc agggtcaggc actggatgtg gcagtgtccg ccctggcctg gctaagcccc    5940
aaggtattgg tgagtggtgc agaagatggg tccttgcagg gctgggcact caaggaatgc    6000
tcccttcagt ccctctggct cctgtccaga ttccagaagc ctgtgctagg actggccact    6060
tcccaggagc tcttggcttc tgcctcagag gatttcacag tgcagctgtg gccaaggcag    6120
ctgctgacgc ggccacacaa ggcagaagac tttccctgtg gcactgagct gcggggacat    6180
gagggccctg tgagctgctg tagtttcagc actgatggag gcagcctggc caccgggggc    6240
cgggatcgga gtctcctctg ctgggacgtg aggacaccca aaacccctgt tttgatccac    6300
tccttccctg cctgtcaccg tgactgggtc actggctgtg cctggaccaa agataaccta    6360
ctgatatcct gctccagtga tggctctgtg gggctctggg acccagagtc aggacagcgg    6420
cttggtcagt tcctgggtca tcagagtgct gtgagcgctg tggcagctgt ggaggagcac    6480
gtggtgtctg tgagccggga tgggaccttg aaagtgtggg accatcaagg cgtggagctg    6540
accagcatcc ctgctcactc aggacccatt agccactgtg cagctgccat ggagccccgt    6600
gcagctggac agcctgggtc agagcttctg gtggtaaccg tcgggctaga tggggccaca    6660
cggttatggc atccactctt ggtgtgccaa acccacaccc tcctgggaca cagcggccca    6720
gtccgtgctg ctgctgtttc agaaacctca ggcctcatgc tgaccgcctc tgaggatggt    6780
tctgtacggc tctggcaggt tcctaaggaa gcagatgaca catgtatacc aaggagttct    6840
gcagccgtca ctgctgtggc ttgggcacca gatggttcca tggcagtatc tggaaatcaa    6900
gctggggaac taatcttgtg gcaggaagct aaggctgtgg ccacagcaca ggctccaggc    6960
cacattggtg ctctgatctg gtcctcggca cacaccttt ttgtcctcag tgctgatgag    7020
aaaatcagcg agtggcaagt gaaactgcgg aagggttcgg caccccggaaa tttgagtctt    7080 cacctgaacc gaattctaca ggaggactta ggggtgctga caagtctgga ttgggctcct    7140
gatggtcact ttctcatctt ggccaaagca gatttgaagt tactttgcat gaagccaggg    7200
gatgctccat ctgaaatctg gagcagctat acagaaaatc ctatgatatt gtccacccac    7260
aaggagtatg gcatatttgt cctgcagccc aaggatcctg gagttctttc tttcttgagg    7320
caaaaggaat caggagagtt tgaagagagg ctgaactttg atataaactt agagaatcct    7380
```

```
agtaggaccc taatatcgat aactcaagcc aaacctgaat ctgagtcctc attttttgtgt      7440 gccagctctg atgggatcct atggaacctg gccaaatgca gcccagaagg agaatggacc      7500
acaggtaaca tgtggcagaa aaaagcaaac actccagaaa cccaaactcc agggacagac      7560
ccatctacct gcagggaatc tgatgccagc atggatagtg atgccagcat ggatagtgag      7620
ccaacaccac atctaaagac acggcagcgt agaaagattc actcgggctc tgtcacagcc      7680
ctccatgtgc tacctgagtt gctggtgaca gcttcgaagg acagagatgt taagctatgg      7740
gagagaccca gtatgcagct gctgggcctg ttccgatgcg aagggtcagt gagctgcctg      7800
gaaccttggc tgggcgctaa ctccacccctg cagcttgccg tgggagacgt gcagggcaat      7860
gtgtactttc tgaattggga atga                                              7884
```

<210> SEQ ID NO 13
<211> LENGTH: 98
<212> TYPE: RNA
<213> ORGANISM: Homo sapiens
<400> SEQUENCE: 13

```
ggcuggcuuu agcucagcgg uuacuucgac aguucuuuaa uugaaacaag caaccugucu      60
ggguuguucg agacccgcgg gcgcucucca guccuuuu                               98
```

<210> SEQ ID NO 14
<211> LENGTH: 88
<212> TYPE: RNA
<213> ORGANISM: Homo sapiens
<400> SEQUENCE: 14

```
ggcuggcuuu agcucagcgg uuacuucgag uacauuguaa ccaccucucu gggugguucg      60
agacccgcgg gugcuuucca gcucuuuu                                          88
```

<210> SEQ ID NO 15
<211> LENGTH: 88
<212> TYPE: RNA
<213> ORGANISM: Homo sapiens
<400> SEQUENCE: 15

```
ggcuggcuuu agcucagcgg uuacuucgcg ugucaucaaa ccaccucucu ggguuguucg      60
agacccgcgg gcgcucucca gcccucuu                                          88
```

<210> SEQ ID NO 16
<211> LENGTH: 252
<212> TYPE: PRT
<213> ORGANISM: Homo sapiens
<400> SEQUENCE: 16

```
Ala Asn Leu Arg Leu Pro Met Ala Ser Ala Leu Pro Glu Ala Leu Cys
1               5                   10                  15

Ser Gln Ser Arg Thr Thr Pro Val Asp Leu Cys Leu Leu Glu Glu Ser
            20                  25                  30

Val Gly Ser Leu Glu Gly Ser Arg Cys Pro Val Phe Ala Phe Gln Ser
        35                  40                  45

Ser Asp Thr Glu Ser Asp Glu Leu Ser Glu Val Leu Gln Asp Ser Cys
    50                  55                  60

Phe Leu Gln Ile Lys Cys Asp Thr Lys Asp Asp Ser Ile Pro Cys Phe
65                  70                  75                  80

Leu Glu Leu Lys Glu Glu Asp Glu Ile Val Cys Thr Gln His Trp Gln
                85                  90                  95
```

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

Val Lys Gly Arg Glu Cys Leu Leu Asp Leu Ile Ala Thr Met Leu Val
145                 150                 155                 160

Leu Gln Phe Ile Arg Thr Arg Leu Glu Lys Gly Ile Val Phe Lys
                165                 170                 175

Ser Leu Met Lys Met Asp Asp Pro Ser Ile Ser Arg Asn Ile Pro Trp
            180                 185                 190

Ala Phe Glu Ala Ile Lys Gln Ala Ser Glu Trp Val Arg Arg Thr Glu
        195                 200                 205

Gly Gln Tyr Pro Ser Ile Cys Pro Arg Leu Glu Leu Gly Asn Asp Trp
    210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ile Ile Asn Phe Glu Lys Leu
1               5

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Glu Trp Thr Ser Ser Asn Val Met Glu Glu Arg Lys Ile Lys Val
1               5                   10                  15

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccccactagt ccatgggctc catcgg                                         26

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

```
-continued

<400> SEQUENCE: 20
tcctgccagt gttgtgtgca gctagcaggg gaaacacatc tgcc          44

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttggcagatg tgtttcccct gctagctgca cacaacactg gcagga        46

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gggctcgagt tagccttgac tgtaatggag                          30
```